US008242080B2

(12) United States Patent
Kuriyan et al.

(10) Patent No.: US 8,242,080 B2
(45) Date of Patent: Aug. 14, 2012

(54) INHIBITORS OF THE EGFR KINASE TARGETING THE ASYMMETRIC ACTIVATING DIMER INTERFACE

(75) Inventors: John Kuriyan, Berkeley, CA (US); Xuewu Zhang, Berkeley, CA (US); Philip Cole, Baltimore, MD (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/444,914

(22) PCT Filed: Oct. 15, 2007

(86) PCT No.: PCT/US2007/081431
§ 371 (c)(1),
(2), (4) Date: May 13, 2009

(87) PCT Pub. No.: WO2008/046107
PCT Pub. Date: Apr. 17, 2008

(65) Prior Publication Data
US 2010/0120678 A1     May 13, 2010

Related U.S. Application Data

(60) Provisional application No. 60/851,668, filed on Oct. 13, 2006, provisional application No. 60/851,921, filed on Oct. 13, 2006.

(51) Int. Cl.
*A61K 38/17* (2006.01)
*C07K 14/435* (2006.01)
(52) U.S. Cl. .................. 514/21.3; 514/21.4; 530/300
(58) Field of Classification Search .................. None
See application file for complete search history.

(56) References Cited

U.S. PATENT DOCUMENTS

| | | | | |
|---|---|---|---|---|
| 5,532,167 A | * | 7/1996 | Cantley et al. | 436/89 |
| 5,985,553 A | * | 11/1999 | King et al. | 435/6 |
| 6,340,583 B1 | | 1/2002 | Yan et al. | |
| 6,673,549 B1 | | 1/2004 | Furness et al. | |
| 2003/0157104 A1 | | 8/2003 | Waksal | |
| 2006/0003970 A1 | | 1/2006 | Jean-Claude et al. | |

FOREIGN PATENT DOCUMENTS

| | | | |
|---|---|---|---|
| EP | 1236474 | | 9/2002 |
| EP | 1236474 A1 | * | 9/2002 |
| WO | WO 94/07913 | * | 4/1994 |
| WO | WO 2008/046107 | | 4/2008 |

OTHER PUBLICATIONS

Azzariti et al., "Prolonged exposure of colon cancer cells to the epidermal growth factor receptor inhibitor gefitinib (Iressa(TM)) and to the antiangiogenic agent ZD6474: Cytotoxic and biomolecular effects." *World Journal of Gastroenterol*, (2006) vol. 12(32): 5140-7.
Bezjak et al., "Symptom improvement in lung cancer patients treated with erlotinib: quality of life analysis of the National Cancer Institute of Canada Clinical Trials Group Study BR.21." *Journal of Clinical Oncology*, (2006) vol. 24(24): 3831-7.
Bulgaru et al., "Erlotinib (Tarceva): a promising drug targeting epidermal growth factor receptor tyrosine kinase." *Expert Review on Anticancer Therapy*, (2003) vol. 3(3): 269-79.
Chan et al., "Mutational analysis of the nucleotide binding site of the epidermal growth factor receptor and v-Src protein-tyrosine kinases." *Journal of Biological Chemistry*, (1996) vol. 27(37): 22619-23.
Ciardiello et al., "Antitumor effect and potentiation of cytotoxic drugs activity in human cancer cells by ZD-1839 (Iressa), an epidermal growth factor receptor-selective tyrosine kinase inhibitor." *Clinical Cancer Research*, (2000) vol. 6:2053-63.
Cunningham et al., "Responses of human colorectal tumor cells to treatment with the anti-epidermal growth factor receptor monoclonal antibody ICR62 used alone and in combination with the EGFR tyrosine kinase inhibitor gefitinib." *Cancer Research*, (2006) vol. 15: 7708-15.
Dancey and Sausville, "Issues and progress with protein kinase inhibitors for cancer treatment." *Nature Reviews. Drug Discovery*, (2003) vol. 2: 296-313.
de Bono and Rowinsky, "The ErbB receptor family: a therapeutic target for cancer." *Trends in Molecular Medicine*, (2002) vol. 8 (4 Suppl): S19-26.
Dusso et al., "Pathogenic mechanisms for parathyroid hyperplasia." *Kidney International Supplement*, (2006) vol. 102: S8-11.
Grunwald and Hidalgo, "Developing inhibitors of the epidermal growth factor receptor for cancer treatment." *Journal of the National Cancer Institute*, (2003) vol. 95: 851-67.
Haber, "Molecular targeted therapy of lung cancer: EGFR mutations and response to EGFR inhibitors." *Cold Spring Harbor Symposia Quantitative Biology*, (2005) vol. 70: 419-26.
Herbst et al., "IMC-C225, an anti-epidermal growth factor receptor monoclonal antibody, for treatment of head and neck cancer." *Expert Opinion on Biological Therapy*, (2002) vol. 1(4): 719-32.
Johnston et al., "Lapatinib: a novel EGFR/HER2 tyrosine kinase inhibitor for cancer." *Drugs of Today*, (2006) vol. 42(7): 441-53.
Khalil et al., "Targeting epidermal growth factor receptor: novel therapeutics in the management of cancer." *Expert Review on anticancer Therapy*, (2003) vol. 3(3): 367-80.
Krishnan et al., "Combination of epidermal growth factor receptor targeted therapy with radiation therapy for malignant gliomas." *Frontiers in Bioscience*, (2003) vol. 8: e1-13.
Lenz, "Anti-EGFR mechanism of action: antitumor effect and underlying cause of adverse events." *Oncology*. Williston Park, NY, (2006) vol. 20, (5 Suppl. 2): 5-13.
Park et al., "Ionizing radiation enhances matrix metalloproteinase-2 secretion and invasion of glioma cells through Src/epidermal growth factor receptor-mediated p38/Akt and phosphatidylinositol 3-kinase/Akt signaling pathways." *Cancer Research*, (2006) vol. 66(17): 8511-19.
Rojo et al., "Pharmacodynamic studies of gefitinib in tumor biopsy specimens from patients with advanced gastric carcinoma." *Journal of Clinical Oncology*, (2006) vol. 24(26): 4309-16.

(Continued)

*Primary Examiner* — Marianne P Allen
(74) *Attorney, Agent, or Firm* — Morgan, Lewis & Bockius LLP; Jeffry S. Mann; Gargi Talukder

(57) ABSTRACT

The invention provides methods and compositions for the modulation of EGFR activity. In particular, inhibition of EGFR activation through an allosteric mechanism is discloses, as is a method for targeted drug discovery and design based on models of the three dimensional structure of the kinase domains of the protein dimers.

2 Claims, 27 Drawing Sheets

OTHER PUBLICATIONS

Seymour "Epidermal growth factor receptor inhibitors: an update on their development as cancer therapeutics." *Current Opinion in Investigational Drugs*, (2003) vol. 4(6): 658-66.

Solomon et al., "EGFR blockade with ZD1839 ("Iressa") potentiates the antitumor effects of single and multiple fractions of ionizing radiation in human A431 squamous cell carcinoma. Epidermal growth factor receptor." *International Journal Radiology, Oncology, Biology, Physics*, (2003) vol. 57(1): 713-23.

Stamos et al., "Structure of the epidermal growth factor receptor kinase domain alone and in complex with a 4-anilinoquinazoline inhibitor." *The Journal of Biological Chemistry*, (2002) vol. 277-(48): 46265-72.

Wiedmann et al., "Novel targeted approaches to treating biliary tract cancer: the dual epidermal growth factor receptor and ErbB-2 tyrosine kinase inhibitor NVP-AEE788 is more efficient than the epidermal growth factor receptor inhibitors gefitinib and erlotinib." *Anticancer Drugs*, (2006) vol. 17(7): 783-95.

Zhang et al., "An allosteric mechanism for activation of the kinase domain of epidermal growth factor receptor." *Cell*, (Jun. 15, 2006) 125: 1137-1149.

Brünger et al., "Crystallography & NMR System: A New Software Suite for Macromolecular Structure Determination." *Acta Crystallaogrphica*, (1998) D54: 905-921.

Zhang et al., "Inhibition of the EGF receptor by binding of MIG6 to an activating kinase domain interface." *Nature*, (2007) vol. 450:741.

Liao, J. et al., "Targeting protein multiple conformations: a structure-based strategy for kinase drug design", *Current Topics in Medicinal Chemistry*, vol. 7, No. 14, pp. 1394-1407 (2007).

Noble, M. et al., "Protein Kinase Inhibitors: Insights into Drug Design from Structure", *Science*, vol. 303, No. 5665, pp. 1800-1805 (2004).

Thaimattam, R. et al., "Protein kinase inhibitors: structural insights into selectivity", *Current Pharmaceutical Design*, vol. 13, No. 27, pp. 2751-2765 (2007).

* cited by examiner

FIG. 1

A. MIG-6 FRAGMENT USED IN 3.5 ANGSTROM RESOLUTION STRUCTURE

SEQ ID NO: 1
$^{313}$EDRPPKVPPREPLSPSNSRTPSPKSLPSYLNGVMPPTQSFAPDPKYVSSKALQRQ$^{372}$

B. MINIMUM FULL EPITOPE IN MIG-6

SEQ ID NO: 2
$^{336}$KSLPSYLNGVMPPTQSFAPDPKYVSS$^{361}$

C. 40-MER PEPTIDE

SEQ ID NO: 3
$^{336}$KSLPSYLNGVMPPTQSFAPDPKYVSS$^{361}$

D. 25-MER PEPTIDE

SEQ ID NO: 4
SYLNGVMPPTQSFAPDPKYVSSKAL

E. 16-MER PEPTIDE

SEQ ID NO: 5
$^{346}$MPPTQSFAPDPKYVSS$^{361}$

F. HUMAN EGFR KINASE DOMAIN

SEQ ID NO: 6
GEAPNQALLRILKETEFKKIKVLGSGAFGTVYKGLWIPEGEKVKIPVAIKELREATSP
KANKEILDEAYVMASVDNPHVCRLLGICLTSTVQLITQLMPFGCLLDYVREHKDNIG
SQYLLNWCVQIAKGMNYLEDRRLVHRDLAARNVLVKTPQHVKITDFGLAKLLGAE
EKEYHAEGGKVPIKWMALESILHRIYTHQSDVWSYGVTVWELMTFGSKPYDGIPAS
EISSILEKGERLPQPPICTIDVYMIMVKCWMIDADSRPKFRELIIEFSKMARDPQRYLVI
QGDERMHLPSPTDSNFYRALMDEEDMDDVVDADEYLIPQQG

G. SUBSTRATE PEPTIDE FOR VESICLE ASSAY

SEQ ID NO: 7
TAENAEYLRVAPQ

H. SUBSTRATE PEPTIDE FOR CRYSTALLIZATION

SEQ ID NO: 8
ENAEYLRVAPQK

I  Src SUBSTRATE PEPTIDE FOR CRYSTALLIZATION

SEQ ID NO: 9
AEEEIYGEFEAKK

FIG. 3

NUCLEOTIDE SEQUENCE OF KINASE DOMAIN EXPRESSION VECTOR CONSTRUCT

GACGCGCCCTGTAGCGGCGCATTAAGCGCGGCGGGTGTGGTGGTTACGCGCAGC
GTGACCGCTACACTTGCCAGCGCCCTAGCGCCCGCTCCTTTCGCTTTCTTCCCTT
CCTTTCTCGCCACGTTCGCCGGCTTTCCCCGTCAAGCTCTAAATCGGGGGCTCCC
TTTAGGGTTCCGATTTAGTGCTTTACGGCACCTCGACCCCAAAAAACTTGATTA
GGGTGATGGTTCACGTAGTGGGCCATCGCCCTGATAGACGGTTTTTCGCCCTTT
GACGTTGGAGTCCACGTTCTTTAATAGTGGACTCTTGTTCCAAACTGGAACAAC
ACTCAACCCTATCTCGGTCTATTCTTTTGATTTATAAGGGATTTTGCCGATTTC
GGCCTATTGGTTAAAAAATGAGCTGATTTAACAAAAATTTAACGCGAATTTTA
ACAAAATATTAACGTTTACAATTTCAGGTGGCACTTTTCGGGGAAATGTGCGC
GGAACCCCTATTTGTTTATTTTTCTAAATACATTCAAATATGTATCCGCTCATG
AGACAATAACCCTGATAAATGCTTCAATAATATTGAAAAAGGAAGAGTATGA
GTATTCAACATTTCCGTGTCGCCCTTATTCCCTTTTTTGCGGCATTTTGCCTTCC
TGTTTTTGCTCACCCAGAAACGCTGGTGAAAGTAAAAGATGCTGAAGATCAGT
TGGGTGCACGAGTGGGTTACATCGAACTGGATCTCAACAGCGGTAAGATCCTTG
AGAGTTTTCGCCCCGAAGAACGTTTTCCAATGATGAGCACTTTTAAAGTTCTGC
TATGTGGCGCGGTATTATCCCGTATTGACGCCGGGCAAGAGCAACTCGGTCGCC
GCATACACTATTCTCAGAATGACTTGGTTGAGTACTCACCAGTCACAGAAAAG
CATCTTACGGATGGCATGACAGTAAGAGAATTATGCAGTGCTGCCATAACCAT
GAGTGATAACACTGCGGCCAACTTACTTCTGACAACGATCGGAGGACCGAAGG
AGCTAACCGCTTTTTTGCACAACATGGGGGATCATGTAACTCGCCTTGATCGTT
GGGAACCGGAGCTGAATGAAGCCATACCAAACGACGAGCGTGACACCACGATG
CCTGTAGCAATGGCAACAACGTTGCGCAAACTATTAACTGGCGAACTACTTAC
TCTAGCTTCCCGGCAACAATTAATAGACTGGATGGAGGCGGATAAAGTTGCAG
GACCACTTCTGCGCTCGGCCCTTCCGGCTGGCTGGTTTATTGCTGATAAATCTG
GAGCCGGTGAGCGTGGGTCTCGCGGTATCATTGCAGCACTGGGGCCAGATGGTA
AGCCCTCCCGTATCGTAGTTATCTACACGACGGGGAGTCAGGCAACTATGGATG
AACGAAATAGACAGATCGCTGAGATAGGTGCCTCACTGATTAAGCATTGGTAA
CTGTCAGACCAAGTTTACTCATATATACTTTAGATTGATTTAAAACTTCATTTT
TAATTTAAAAGGATCTAGGTGAAGATCCTTTTTGATAATCTCATGACCAAAAT
CCCTTAACGTGAGTTTTCGTTCCACTGAGCGTCAGACCCCGTAGAAAAGATCAA
AGGATCTTCTTGAGATCCTTTTTTTCTGCGCGTAATCTGCTGCTTGCAAACAAA
AAAACCACCGCTACCAGCGGTGGTTTGTTTGCCGGATCAAGAGCTACCAACTCT
TTTTCCGAAGGTAACTGGCTTCAGCAGAGCGCAGATACCAAATACTGTCCTTCT
AGTGTAGCCGTAGTTAGGCCACCACTTCAAGAACTCTGTAGCACCGCCTACATA
CCTCGCTCTGCTAATCCTGTTACCAGTGGCTGCTGCCAGTGGCGATAAGTCGTG
TCTTACCGGGTTGGACTCAAGACGATAGTTACCGGATAAGGCGCAGCGGTCGGG
CTGAACGGGGGGTTCGTGCACACAGCCCAGCTTGGAGCGAACGACCTACACCG
AACTGAGATACCTACAGCGTGAGCATTGAGAAAGCGCCACGCTTCCCGAAGGG
AGAAAGGCGGACAGGTATCCGGTAAGCGGCAGGGTCGGAACAGGAGAGCGCAC
GAGGGAGCTTCCAGGGGGAAACGCCTGGTATCTTTATAGTCCTGTCGGGTTTCG
CCACCTCTGACTTGAGCGTCGATTTTTGTGATGCTCGTCAGGGGGCGGAGCCT
ATGGAAAAACGCCAGCAACGCGGCCTTTTTACGGTTCCTGGCCTTTTGCTGGCC
TTTTGCTCACATGTTCTTTCCTGCGTTATCCCCTGATTCTGTGGATAACCGTATT

FIG. 3 CONTINUED

```
ACCGCCTTTGAGTGAGCTGATACCGCTCGCCGCAGCCGAACGACCGAGCGCAGC
GAGTCAGTGAGCGAGGAAGCGGAAGAGCGCCTGATGCGGTATTTTCTCCTTACG
CATCTGTGCGGTATTTCACACCGCAGACCAGCCGCGTAACCTGGCAAAATCGGT
TACGGTTGAGTAATAAATGGATGCCCTGCGTAAGCGGGTGTGGGCGGACAATA
AAGTCTTAAACTGAACAAAATAGATCTAAACTATGACAATAAAGTCTTAAACT
AGACAGAATAGTTGTAAACTGAAATCAGTCCAGTTATGCTGTGAAAAAGCATA
CTGGACTTTTGTTATGGCTAAAGCAAACTCTTCATTTTCTGAAGTGCAAATTGC
CCGTCGTATTAAAGAGGGGCGTGGCCAAGGGCATGGTAAAGACTATATTCGCG
GCGTTGTGACAATTTACCGAACAACTCCGCGGCCGGGAAGCCGATCTCGGCTTG
AACGAATTGTTAGGTGGCGGTACTTGGGTCGATATCAAAGTGCATCACTTCTTC
CCGTATGCCCAACTTTGTATAGAGAGCCACTGCGGGATCGTCACCGTAATCTGC
TTGCACGTAGATCACATAAGCACCAAGCGCGTTGGCCTCATGCTTGAGGAGATT
GATGAGCGCGGTGGCAATGCCCTGCCTCCGGTGCTCGCCGGAGACTGCGAGATC
ATAGATATAGATCTCACTACGCGGCTGCTCAAACCTGGGCAGAACGTAAGCCG
CGAGAGCGCCAACAACCGCTTCTTGGTCGAAGGCAGCAAGCGCGATGAATGTC
TTACTACGGAGCAAGTTCCCGAGGTAATCGGAGTCCGGCTGATGTTGGGAGTAG
GTGGCTACGTCTCCGAACTCACGACCGAAAAGATCAAGAGCAGCCCGCATGGA
TTTGACTTGGTCAGGGCCGAGCCTACATGTGCGAATGATGCCCATACTTGAGCC
ACCTAACTTTGTTTTAGGGCGACTGCCCTGCTGCGTAACATCGTTGCTGCTGCG
TAACATCGTTGCTGCTCCATAACATCAAACATCGACCCACGGCGTAACGCGCTT
GCTGCTTGGATGCCCGAGGCATAGACTGTACAAAAAAACAGTCATAACAAGCC
ATGAAAACCGCCACTGCGCCGTTACCACCGCTGCGTTCGGTCAAGGTTCTGGAC
CAGTTGCGTGAGCGCATACGCTACTTGCATTACAGTTTACGAACCGAACAGGCT
TATGTCAACTGGGTTCGTGCCTTCATCCGTTTCCACGGTGTGCGTCACCCGGCA
ACCTTGGGCAGCAGCGAAGTCGAGGCATTTCTGTCCTGGCTGGCGAACGAGCGC
AAGGTTTCGGTCTCCACGCATCGTCAGGCATTGGCGGCCTTGCTGTTCTTCTAC
GGCAAGGTGCTGTGCACGGATCTGCCCTGGCTTCAGGAGATCGGAAGACCTCGG
CCGTCGCGGCGCTTGCCGGTGGTGCTGACCCCGGATGAAGTGGTTCGCATCCTC
GGTTTTCTGGAAGGCGAGCATCGTTTGTTCGCCCAGGACTCTAGCTATAGTTCT
AGTGGTTGGCTACGTATACTCCGGAATATTAATAGATCATGGAGATAATTAAA
ATGATAACCATCTCGCAAATAAATAAGTATTTTACTGTTTTCGTAACAGTTTTG
TAATAAAAAAACCTATAAATATTCCGGATTATTCATACCGTCCCACCATCGGG
CGCGGATCTCGGTCCGAAACCATGTCGTACTACCATCACCATCACCATCACGAT
TACGATATCCCAACGACCGAAAACCTGTATTTTCAGGGCGCCATGGGAGAAGC
TCCCAACCAAGCTCTCTTGAGGATCTTGAAGGAAACTGAATTCAAAAAGATCA
AAGTGCTGGGCTCCGGTGCGTTCGGCACGGTGTATAAGGGACTCTGGATCCCAG
AAGGTGAGAAAGTTAAAATTCCCGTCGCTATCAAGGAATTAAGAGAAGCAACA
TCTCCGAAAGCCAACAAGGAAATCCTCGATGAAGCCTACGTGATGGCCAGCGT
GGACAACCCCCACGTGTGCCGCCTGCTGGGCATCTGCCTCACCTCCACCGTGCA
ACTCATCACGCAGCTCATGCCCTTCGGCTGCCTCCTGGACTATGTCCGGGAACA
CAAAGACAATATTGGCTCCCAGTACCTGCTCAACTGGTGTGTGCAGATCGCAA
AGGGCATGAACTACTTGGAGGACCGTCGCTTGGTGCACCGCGACCTGGCAGCCA
GGAACGTACTGGTGAAAACACCGCAGCATGTCAAGATCACAGATTTTGGGCTG
```

FIG. 3 CONTINUED

```
GCCAAACTGCTGGGTGCGGAAGAGAAAGAATACCATGCAGAAGGAGGCAAAGT
GCCTATCAAGTGGATGGCATTGGAATCAATTTTACACAGAATCTATACCCACC
AGAGTGATGTCTGGAGCTACGGGGTGACCGTTTGGGAGTTGATGACCTTTGGAT
CCAAGCCATATGACGGAATCCCTGCCAGCGAGATCTCCTCCATCCTGGAGAAA
GGAGAACGCCTCCCTCAGCCACCCATATGTACCATCGATGTCTACATGATCATG
GTCAAGTGCTGGATGATAGACGCAGATAGTCGCCCAAAGTTCCGTGAGTTGATC
ATCGAATTCTCCAAAATGGCCCGAGACCCCCAGCGCTACCTTGTCATTCAGGGG
GATGAAAGAATGCATTTGCCAAGTCCTACAGACTCCAACTTCTACCGTGCCCTG
ATGGATGAAGAAGACATGGACGACGTGGTGGATGCCGACGAGTACCTCATCCC
ACAGCAGGGTTAGAAGCTTGTCGAGAAGTACTAGAGGATCATAATCAGCCATA
CCACATTTGTAGAGGTTTTACTTGCTTTAAAAAACCTCCCACACCTCCCCCTGA
ACCTGAAACATAAAATGAATGCAATTGTTGTTGTTAACTTGTTTATTGCAGCTT
ATAATGGTTACAAATAAAGCAATAGCATCACAAATTTCACAAATAAAGCATTT
TTTTCACTGCATTCTAGTTGTGGTTTGTCCAAACTCATCAATGTATCTTATCAT
GTCTGGATCTGATCACTGCTTGAGCCTAGGAGATCCGAACCAGATAAGTGAAA
TCTAGTTCCAAACTATTTTGTCATTTTTAATTTTCGTATTAGCTTACGACGCTA
CACCCAGTTCCCATCTATTTTGTCACTCTTCCCTAAATAATCCTTAAAAACTCC
ATTTCCACCCCTCCCAGTTCCCAACTATTTTGTCCGCCCACAGCGGGGCATTTT
TCTTCCTGTTATGTTTTAATCAAACATCCTGCCAACTCCATGTGACAAACCGT
CATCTTCGGCTACTTTTTCTCTGTCACAGAATGAAAATTTTTCTGTCATCTCTT
CGTTATTAATGTTTGTAATTGACTGAATATCAACGCTTATTTGCAGCCTGAATG
                        GCGAATGG
```

SEQ ID NO: 10

FIG. 6
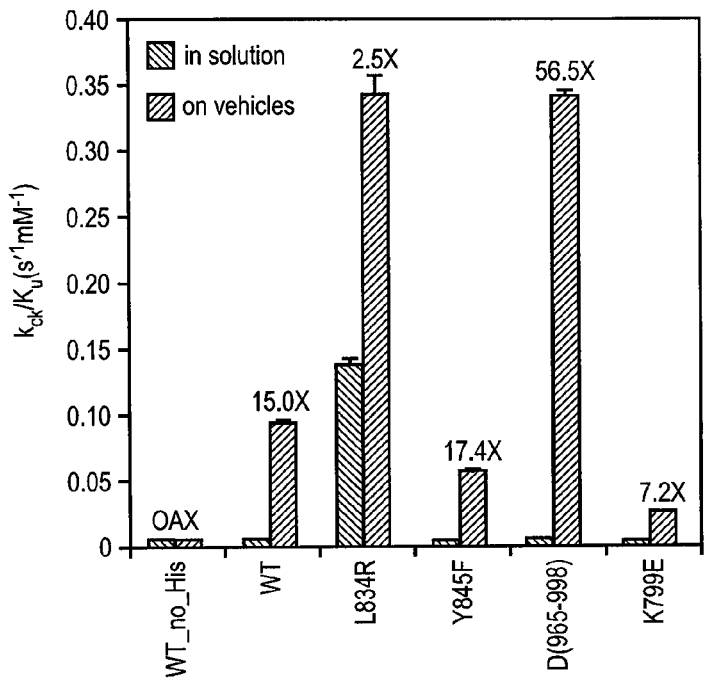
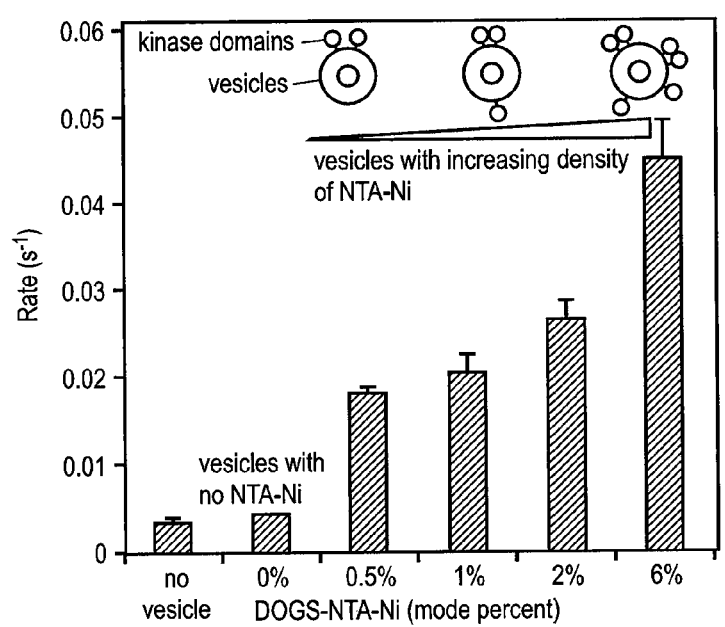

FIG. 15
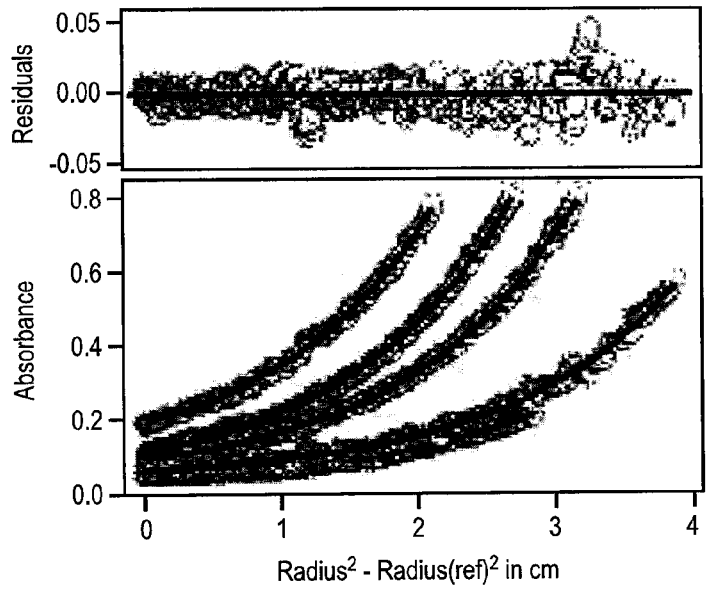
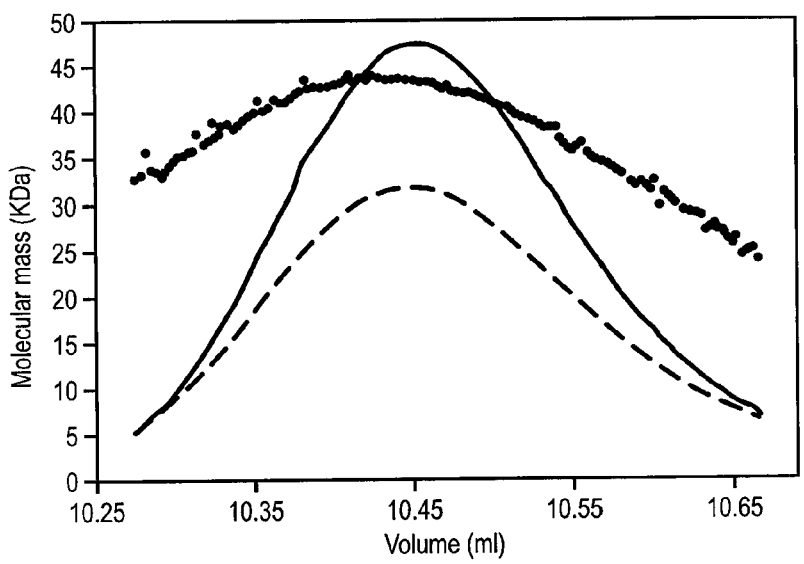

FIG. 17
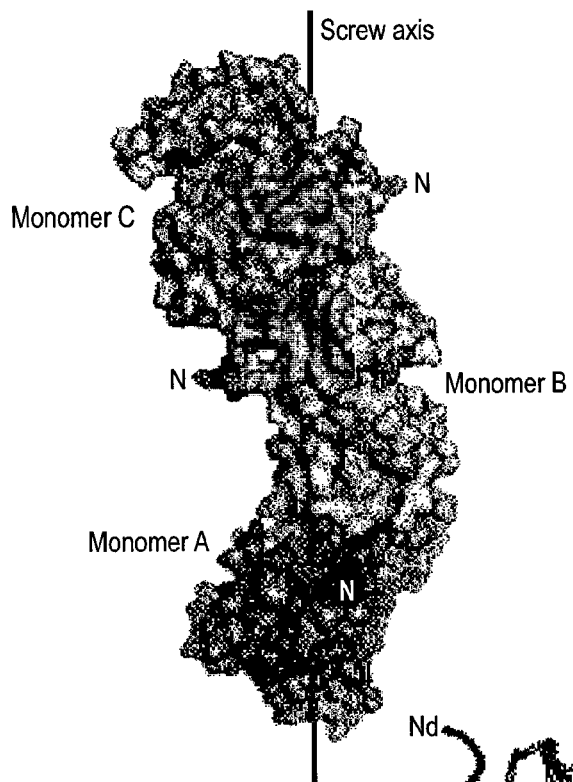
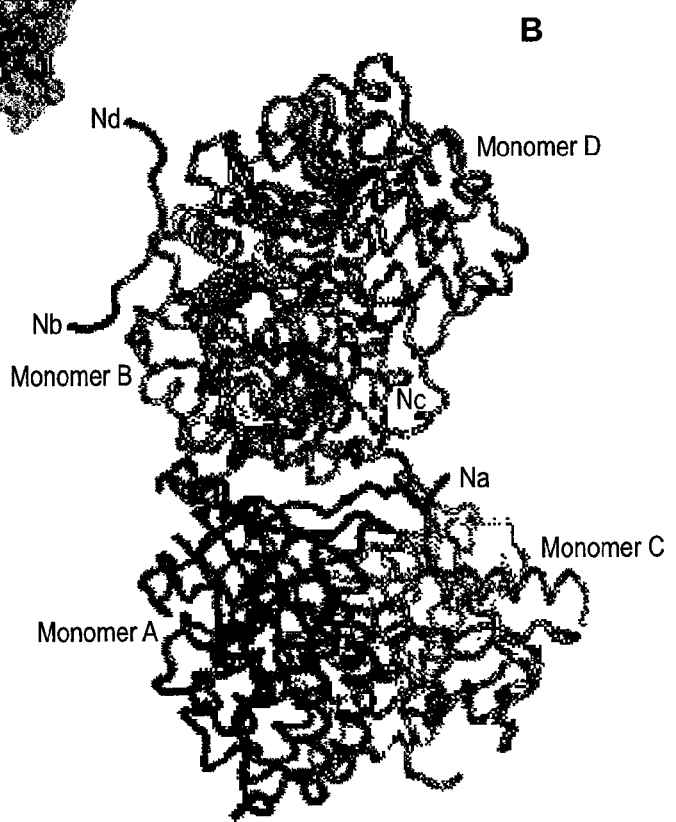

FIG. 18
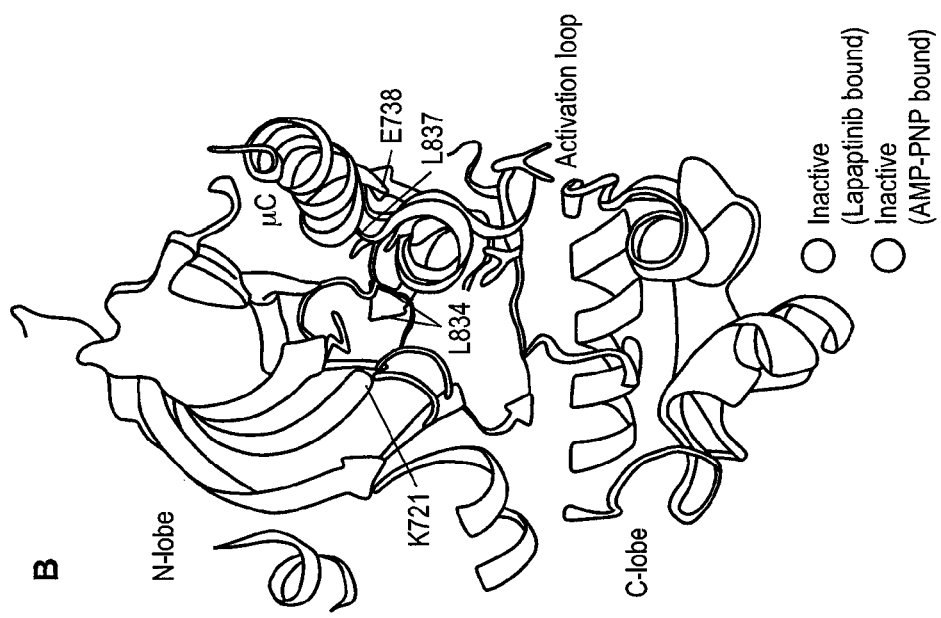
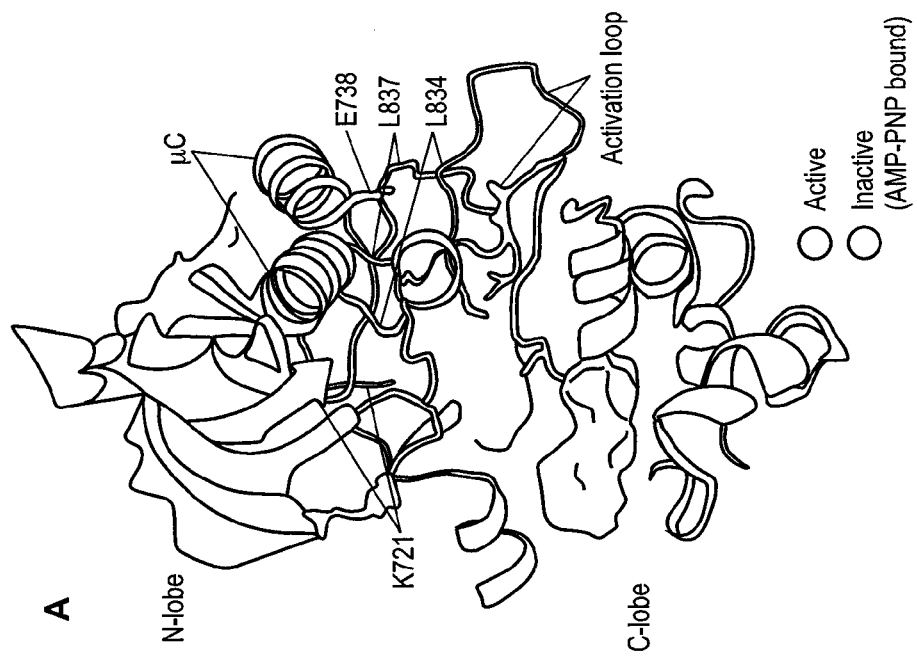

FIG. 22

EXPRESSION VECTOR OF MIG-6 PEPTIDE

ACGTTATCGACTGCACGGTGCACCAATGCTTCTGGCGTCAGGCAGCCATCGGA
AGCTGTGGTATGGCTGTGCAGGTCGTAAATCACTGCATAATTCGTGTCGCTCAA
GGCGCACTCCCGTTCTGGATAATGTTTTTTGCGCCGACATCATAACGGTTCTGG
CAAATATTCTGAAATGAGCTGTTGACAATTAATCATCGGCTCGTATAATGTGT
GGAATTGTGAGCGGATAACAATTTCACACAGGAAACAGTATTCATGTCCCCTA
TACTAGGTTATTGGAAAATTAAGGGCCTTGTGCAACCCACTCGACTTCTTTTGG
AATATCTTGAAGAAAATATGAAGAGCATTTGTATGAGCGCGATGAAGGTGAT
AAATGGCGAAACAAAAGTTTGAATTGGGTTTGGAGTTTCCCAATCTTCCTTA
TTATATTGATGGTGATGTTAAATTAACACAGTCTATGGCCATCATACGTTATA
TAGCTGACAAGCACAACATGTTGGGTGGTTGTCCAAAAGAGCGTGCAGAGATT
TCAATGCTTGAAGGAGCGGTTTTGGATATTAGATACGGTGTTTCGAGAATTGC
ATATAGTAAAGACTTTGAAACTCTCAAAGTTGATTTTCTTAGCAAGCTACCTG
AAATGCTGAAAATGTTCGAAGATCGTTTATGTCATAAAACATATTTAAATGGT
GATCATGTAACCCATCCTGACTTCATGTTGTATGACGCTCTTGATGTTGTTTTA
TACATGGACCCAATGTGCCTGGATGCGTTCCCAAAATTAGTTTGTTTTAAAAA
ACGTATTGAAGCTATCCCACAAATTGATAAGTACTTGAAATCCAGCAAGTATA
TAGCATGGCCTTTGCAGGGCTGGCAAGCCACGTTTGGTGGTGGCGACCATCCTC
CAAAATCGGATCTGGAAGTTCTGTTCCAGGGGCCCCTGGGATCCaggcctcccaaa
gtaccgccaagagaacctttgtcaccgagtaactcgcgcacaccgagtcccaaaagccttccgtctt
acctcaatggggtcatgcccccgacacagagctttgcccctgatcccaagtatgtcagcagcaaag
cactgcaaagacagaacagcgaaggatctgccagttagCTCGAGCGGCCGCATCGTGACT
GACTGACGATCTGCCTCGCGCGTTTCGGTGATGACGGTGAAAACCTCTGACAC
ATGCAGCTCCCGGAGACGGTCACAGCTTGTCTGTAAGCGGATGCCGGGAGCAG
ACAAGCCCGTCAGGGCGCGTCAGCGGGTGTTGGCGGGTGTCGGGGCGCAGCCAT
GACCCAGTCACGTAGCGATAGCGGAGTGTATAATTCTTGAAGACGAAAGGGCC
TCGTGATACGCCTATTTTTATAGGTTAATGTCATGATAATAATGGTTTCTTAG
ACGTCAGGTGGCACTTTTCGGGGAAATGTGCGCGGAACCCCTATTTGTTTATTT
TTCTAAATACATTCAAATATGTATCCGCTCATGAGACAATAACCCTGATAAAT
GCTTCAATAATATTGAAAAAGGAAGAGTATGAGTATTCAACATTTCCGTGTCG
CCCTTATTCCCTTTTTTGCGGCATTTTGCCTTCCTGTTTTTGCTCACCCAGAAAC
GCTGGTGAAAGTAAAAGATGCTGAAGATCAGTTGGGTGCACGAGTGGGTTACA
TCGAACTGGATCTCAACAGCGGTAAGATCCTTGAGAGTTTTCGCCCCGAAGAA
CGTTTTCCAATGATGAGCACTTTTAAAGTTCTGCTATGTGGCGCGGTATTATCC
CGTGTTGACGCCGGGCAAGAGCAACTCGGTCGCCGCATACACTATTCTCAGAA
TGACTTGGTTGAGTACTCACCAGTCACAGAAAAGCATCTTACGGATGGCATGA
CAGTAAGAGAATTATGCAGTGCTGCCATAACCATGAGTGATAACACTGCGGCC
AACTTACTTCTGACAACGATCGGAGGACCGAAGGAGCTAACCGCTTTTTTGCA
CAACATGGGGGATCATGTAACTCGCCTTGATCGTTGGGAACCGGAGCTGAATG
AAGCCATACCAAACGACGAGCGTGACACCACGATGCCTGCAGCAATGGCAACA
ACGTTGCGCAAACTATTAACTGGCGAACTACTTACTCTAGCTTCCCGGCAACA
ATTAATAGACTGGATGGAGGCGGATAAAGTTGCAGGACCACTTCTGCGCTCGG
CCCTTCCGGCTGGCTGGTTTATTGCTGATAAATCTGGAGCCGGTGAGCGTGGGT
CTCGCGGTATCATTGCAGCACTGGGGCCAGATGGTAAGCCCTCCCGTATCGTAG

FIG. 22 CONTINUED

TTATCTACACGACGGGGAGTCAGGCAACTATGGATGAACGAAATAGACAGATC
GCTGAGATAGGTGCCTCACTGATTAAGCATTGGTAACTGTCAGACCAAGTTTA
CTCATATATACTTTAGATTGATTTAAAACTTCATTTTTAATTTAAAAGGATCT
AGGTGAAGATCCTTTTTGATAATCTCATGACCAAAATCCCTTAACGTGAGTTT
TCGTTCCACTGAGCGTCAGACCCCGTAGAAAAGATCAAAGGATCTTCTTGAGA
TCCTTTTTTTCTGCGCGTAATCTGCTGCTTGCAAACAAAAAAACCACCGCTACC
AGCGGTGGTTTGTTTGCCGGATCAAGAGCTACCAACTCTTTTTCCGAAGGTAAC
TGGCTTCAGCAGAGCGCAGATACCAAATACTGTCCTTCTAGTGTAGCCGTAGT
TAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTG
GACTCAAGACGATAGTTACCGGATAAGGCGCAGCGGTCGGGCTGAACGGGGGG
TTCGTGCACACAGCCCAGCTTGGAGCGAACGACCTACACCGAACTGAGATACC
TACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACT
TGAGCGTCGATTTTTGTGATGCTCGTCAGGGGGGCGGAGCCTATGGAAAAACG
CCAGCAACGCGGCCTTTTACGGTTCCTGGCCTTTTGCTGGCCTTTTGCTCACA
TGTTCTTTCCTGCGTTATCCCCTGATTCTGTGGATAACCGTATTACCGCCTTTG
AGTGAGCTGATACCGCTCGCCGCAGCCGAACGACCGAGCGCAGCGAGTCAGTG
AGCGAGGAAGCGGAAGAGCGCCTGATGCGGTATTTTCTCCTTACGCATCTGTGC
GGTATTTCACACCGCATAAATTCCGACACCATCGAATGGTGCAAAACCTTTCG
CGGTATGGCATGATAGCGCCCGGAAGAGAGTCAATTCAGGGTGGTGAATGTGA
AACCAGTAACGTTATACGATGTCGCAGAGTATGCCGGTGTCTCTTATCAGACC
GTTTCCCGCGTGGTGAACCGGCCAGCCACGTTTCTGCGAAAACGCGGGAAAAA
GTGGAAGCGGCGATGCGGAGCTGAATTACATTCCCAACCGCGTGGCACAACA
ACTGGCGGGCAAACAGTCGTTGCTGATTGGCGTTGCCACCTCCAGTCTGGCCCT
GCACGCGCCGTCGCAAATTGTCGCGGCGATTAAATCTCGCGCCGATCAACTGGG
TGCCAGCGTGGTGGTGTCGATGGTAGAACGAAGCGGCGTCGAAGCCTGTAAAG
CGGCGGTGCACAATCTTCTCGCGCAACGCGTCAGTGGGCTGATCATTAACTATC
CGCTGGATGACCAGGATGCCATTGCTGTGGAAGCTGCCTGCACTAATGTTCCGG
CGTTATTTCTTGATGTCTCTGACCAGACACCCATCAACAGTATTATTTTCTCCC
ATGAAGACGGTACGCGACTGGGCGTGGAGCATCTGGTCGCATTGGGTCACCAG
CAAATCGCGCTGTTAGCGGGCCCATTAAGTTCTGTCTCGGCGCGTCTGCGTCTG
GCTGGCTGGCATAAATATCTCACTCGCAATCAAATTCAGCCGATAGCGGAACG
GGAAGGCGACTGGAGTGCCATGTCCGGTTTTCAACAAACCATGCAAATGCTGA
ATGAGGGCATCGTTCCCACTGCGATGCTGGTTGCCAACGATCAGATGGCGCTGG
GCGCAATGCGCGCCATTACCGAGTCCGGGCTGCGCGTTGGTGCGGATATCTCGG
TAGTGGGATACGACGATACCGAAGACAGCTCATGTTATATCCCGCCGTCAACC
ACCATCAAACAGGATTTTCGCCTGCTGGGGCAAACCAGCGTGGACCGCTTGCT
GCAACTCTCTCAGGGCCAGGCGGTGAAGGGCAATCAGCTGTTGCCCGTCTCACT
GGTGAAAAGAAAAACCACCCTGGCGCCCAATACGCAAACCGCCTCTCCCCGCG
CGTTGGCCGATTCATTAATGCAGCTGGCACGACAGGTTTCCCGACTGGAAAGC
GGGCAGTGAGCGCAACGCAATTAATGTGAGTTAGCTCACTCATTAGGCACCCC

FIG. 22 CONTINUED

```
AGGCTTTACACTTTATGCTTCCGGCTCGTATGTTGTGTGGAATTGTGAGCGGAT
AACAATTTCACACAGGAAACAGCTATGACCATGATTACGGATTCACTGGCCGT
CGTTTTACAACGTCGTGACTGGGAAAACCCTGGCGTTACCCAACTTAATCGCCT
TGCAGCACATCCCCCTTTCGCCAGCTGGCGTAATAGCGAAGAGGCCCGCACCG
ATCGCCCTTCCCAACAGTTGCGCAGCCTGAATGGCGAATGGCGCTTTGCCTGGT
TTCCGGCACCAGAAGCGGTGCCGGAAAGCTGGCTGGAGTGCGATCTTCCTGAG
GCCGATACTGTCGTCGTCCCCTCAAACTGGCAGATGCACGGTTACGATGCGCCC
ATCTACACCAACGTAACCTATCCCATTACGGTCAATCCGCCGTTTGTTCCCACG
GAGAATCCGACGGGTTGTTACTCGCTCACATTTAATGTTGATGAAAGCTGGCT
     ACAGGAAGGCCAGACGCGAATTATTTTTGATGGCGTTGGAATT
```

SEQ ID NO: 11

INHIBITORS OF THE EGFR KINASE TARGETING THE ASYMMETRIC ACTIVATING DIMER INTERFACE

CROSS-REFERENCE TO RELATED APPLICATIONS

The present application claims the benefit of the filing dates of U.S. Provisional Patent Application No. 60/851,668, filed Oct. 13, 2006, and of U.S. Provisional Patent Application No. 60/851,921, filed Oct. 13, 2006, which are both incorporated by reference in their entirety for all purposes.

STATEMENT AS TO RIGHTS TO INVENTIONS MADE UNDER FEDERALLY SPONSORED RESEARCH OR DEVELOPMENT

This invention was made with Government support under Grant No. CA096504 awarded by the National Institutes of Health. The Government has certain rights in this invention.

FIELD OF THE INVENTION

The invention relates generally to the field of molecular biology, biochemistry, and cell biology of the Epidermal Growth Factor Receptor (EGFR). In particular, the instant invention provides methods and compositions for the modulation of EGFR. EGFR receptors play critical roles in regulating cell proliferation, differentiation, and migration, and their abnormal activation is associated with a variety of human cancers, including lung, breast, pancreatic, ovarian and prostate cancer. Compositions and methods of the invention can be used to prevent, cure, treat, or ameliorate these cancers as well as other diseases associated with EGFRs.

BACKGROUND INFORMATION

The following is provided as background information only and should not be taken as an admission that any subject matter discussed or that any reference mentioned is prior art to the instant invention. All publications and patent applications herein are incorporated by reference to the same extent as if each individual publication or patent application was specifically and individually indicated to be incorporated by reference.

In multi-cellular organisms, communication between individual cells is essential for the regulation of complex biological processes such as growth, differentiation, motility and survival. Receptor tyrosine kinases are among the primary mediators of signals between the surface of the cell to target proteins in cytoplasmic compartments and in the nucleus. One family of receptor tyrosine kinases, the epidermal growth factor receptors (EGFRs), has been shown to have a critical role in these signal transduction processes.

Members of the epidermal growth factor receptor family (EGFR/ErbB1/HER1, ErbB2/HER2, ErbB3/HER3, and ErbB4/HER4) are transmembrane tyrosine kinases that are activated by ligand-induced dimerization. (Schreiber et al., (1983) *Journal of Biological Chemistry* 258(2):846-53.; Ushiro and Cohen, (1980) *Journal of Biological Chemistry* 255(18):8363-5.). These receptors regulate cell proliferation, differentiation, and migration, and their abnormal activation is associated with a variety of human cancers. (Yarden and Sliwkowski, (2001) *Nature Reviews Molecular Cellular Biology* 2(2):127-37). Several cancer drugs (for example, Erlotinib) interact with the ATP-binding site of the EGFR kinase to halt tumor growth and increase apoptosis in cancer cells.

It is known that the EGFR kinase domain is activated after ligand-induced dimerization of the extracellular region of the receptor, although the underlying mechanism has remained elusive. Studies have shown that mutations in the catalytic domain of EGFR can interfere with the kinase activity of these proteins. (Chan et al., (1996) *Journal of Biological Chemistry, Vol.* 27(37): 22619-23.).

The development of compounds that directly inhibit the kinase activity of the EGFR, as well as antibodies that reduce EGFR kinase activity by blocking EGFR activation, are areas of intense research effort (de Bono and Rowinsky, (2002) *Trends in Molecular Medicine*, Vol. 8 (4 Suppl): S19-26; Dancey and Sausville, (2003) *Nature Reviews. Drug Discovery*, Vol. 2: 296-313.). Several studies have demonstrated or suggested that some EGFR kinase inhibitors might improve tumor cell or neoplasia killing when used in combination with certain other anti-cancer or chemotherapeutic agents or treatments (e.g. Herbst et al., (2002) *Expert Opinion on Biological Therapy*, Vol. 1(4): 719-32; Solomon et al., (2003) *International Journal Radiology, Oncology, Biology, Physics*, Vol. 57(1): 713-23; Krishnan et al., (2003) *Frontiers in Bioscience*, Vol. 8: e1-13; Grunwald and Hidalgo, (2003) *Journal of the National Cancer Institute*, Vol. 95: 851-67; Seymour, (2003) *Current Opinion in Investigational Drugs*, Vol. 4(6): 658-66; Khalil et al., (2003) *Expert Review on Anticancer Therapy*, Vol. 3(3): 367-80; Bulgaru et al., (2003) *Expert Review on Anticancer Therapy*, Vol. 3(3): 269-79; Ciardiello et al., (2000) *Clinical Cancer Research*, Vol. 6: 2053-63; and Patent Publication No: US 2003/0157104).

The Mig-6 protein has been shown to be a negative modulator of EGFR activity. Ullrich et al (WO 02/067975) described using the protein to inhibit EGFR activity in rat fibroblasts. The interaction between EGFR and Mig-6 was determined using a yeast two hybrid screen. A similar method was used to screen for other potential modulators of EGFR. However, the high rate of false negatives inherent to a yeast two hybrid screen makes such a process inefficient for most drug discovery uses.

Drugs targeting EGFR that are currently in use inhibit EGFR through interaction with the active site, but such pharmaceuticals are not effective for many EGFR-related illnesses.

A need exists, therefore, for methods and compositions capable of modulating the activation of EGFR at sites other than the active site.

SUMMARY OF THE INVENTION

Accordingly, the present invention provides methods and compositions for modulating EGFR activation. Preferred compositions of the invention include inhibitors of EGFR activation which act upon an asymmetric dimer interface between EGFR homodimers and heterodimers. The invention also provides functional assay systems for screening for allosteric inhibitors of EGFR activation and methods for targeted drug discovery based on structural analysis of the EGFR protein.

In a preferred aspect, the invention provides an isolated polypeptide that interacts with an EGFR peptide and allosterically inhibits activation of said EGFR polypeptide. In one embodiment, the isolated polypeptide allosterically inhibits EGFR activation by preventing formation of an asymmetric dimer interface between EGFR molecules. In such an embodiment, the asymmetric dimer interface is an interface between kinase domains of the EGFR molecules.

In one aspect, the invention provides a method for inhibiting EGFR activation. This method includes the step of contacting an EGFR kinase domain with a test molecule that interacts with said EGFR kinase domain. This contacting between the EGFR kinase domain and the test molecule can prevent formation of an asymmetric dimer interface between the EGFR molecule and a kinase domain of a second EGFR molecule. In a preferred embodiment, the test molecule includes an isolated polypeptide with an amino acid sequence selected from: SEQ ID NOs: 1-9.

In another aspect, the invention provides a method for screening for potential inhibitors of EGFR activation. This method includes the steps of: (a) attaching an isolated polypeptide corresponding to an EGFR kinase domain to a lipid vesicle surface to form a conjugated polypeptide; (b) determining activity of the conjugated polypeptide; and (c) contacting the conjugated polypeptide with a test compound; (d) comparing the activity of step (b) with the activity of (c). In a preferred embodiment, following step (c), the invention provides a step in which the activity of the conjugated polypeptide is determined. In a still further preferred embodiment, if the activity determined in (c) is less than the activity determined in (b), the comparing step in (d) identifies the test compound as an inhibitor of EGFR activation.

In another aspect, the invention provides a method for screening for inhibitors of EGFR activation using a vesicle assay system. In this method, an isolated polypeptide corresponding to an EGFR kinase domain is attached to a vesicle (e.g., a lipid vesicle) surface, thus forming a conjugated polypeptide, and the activity of the conjugated polypeptide is determined. The conjugated polypeptide is then contacted with a test compound. Following contact with the test compound, activity of the conjugated polypeptide is measured and compared to its activity prior to contact with the test compound. If the activity of the conjugated polypeptide is lower after contact with the test compound than the measured activity before contact, then the test compound is identified as an inhibitor of EGFR activation.

In one aspect, the invention provides a method of screening for compounds which bind to kinase domain of EGFR, and this method includes a step of determining whether a potential binding agent can compete with a polypeptide comprising an amino acid sequence selected from SEQ ID NOs: 1-9.

In another aspect, the invention provides a method of targeted drug discovery which includes the following steps: (a) determining structural information of an EGFR kinase domain co-crystallized with a control molecule; (b) identifying residues of the EGFR kinase domain which interact with said the molecule; (c) comparing information from (a) and (b) to a database of potential therapeutics; and (d) selecting potential therapeutics from the database that are most likely to interact with the EGFR kinase domain in a manner similar to the control molecule. In a preferred embodiment, the information from (a) and (b) is used to narrow search parameters based on amino acid sequence and predicted structure.

In one aspect, the invention provides a pharmaceutical composition which includes one or more isolated polypeptides with amino acid sequence selected from SEQ ID NOs: 1-9. In a preferred aspect, the one or more polypeptides are combined with at least one pharmaceutically acceptable carrier.

In another aspect, the invention provides a vesicle assay system that includes a polypeptide conjugated to a lipid vesicle surface, where that polypeptide includes an EGFR kinase domain; and a means of detecting if the polypeptide forms dimers in the presence of a test compound. In a preferred aspect, an inhibition of dimer formation identifies the polypeptide as an inhibitor of EGFR kinase activity.

In another aspect, the invention provides a method for identifying compounds that modulate activation of EGFR. This method uses an X-ray crystal structure of an EGFR kinase domain and an X-ray crystal structure of an EGFR kinase domain co-crystallized with a control compound to predict the ability of a test compound to modulate activation of EGFR.

Other objects, aspects and advantages of the instant invention are set forth in the detailed description which follows.

BRIEF DESCRIPTION OF THE DRAWINGS

FIG. 1A-I shows the sequences of the identified regions of the Mig-6 peptide or the EGFR kinase domain.

FIG. 3 is the nucleotide sequence of the expression vector construct for the EGFR kinase domain.

FIG. 6 shows data from a vesicle assay system. FIG. 6A shows catalytic activity of the wildtype and mutant EGFR kinase domains in solution and attached to vesicles. FIG. 6B shows the concentration-dependent activation of the wild-type kinase domain upon attachment to lipid vesicles.

FIG. 7C shows the crystal structure of an inactive Src kinase in complex with AMP-PNP.

FIG. 8A shows the asymmetric dimer (left panel) in comparison to a CDK2/cyclin A complex (right panel). FIG. 8B shows detailed views of the asymmetric dimer interface.

FIG. 9A shows the residues involved in the symmetric dimer interface. FIG. 9B shows the results of a phosphorylation assay for the wildtype interface and various mutants.

FIG. 15 displays data regarding an EGFR kinase domain monomer. FIG. 15A shows data from an ultracentrifugation experiment of an EGFR kinase domain monomer in solution. The lower panel shows the fit of the data (circles) to a single species ideal model (solid curve), which yielded a molecular weight of 37890 Da. Residuals of the fitting (circles) are plotted in the upper panel. FIG. 15B shows the results of a dynamic light scattering experiment for an EGFR kinase domain monomer in solution.

FIG. 17 shows higher order oligomers based on the CDK/cyclin-like asymmetric dimer (A) and a comparison of the asymmetric and symmetric dimers (B).

FIG. 18 is a comparison of the active and inactive conformations of the EGFR kinase domain. 18A is a superimposition of the active (ATP analog-peptide conjugate bound) and inactive (AMP-PNP bound V924R mutant) structures. 18B is a superimposition of the structures of the AMP-PNP bound V924R mutant and the Lapatinib-bound wild type EGFR kinase domain.

FIG. 22 shows the nucleotide sequence of the Mig-6 expression vector construct. SEQ ID NO: 11.

DETAILED DESCRIPTION OF THE INVENTION

Introduction

Figure 2:
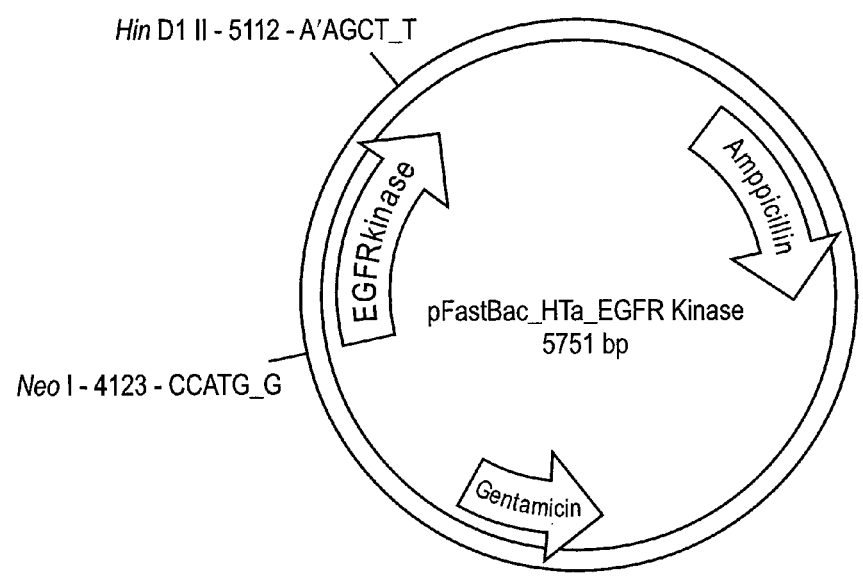
FIG. 2 shows the vector map of the construct used to express the human EGFR kinase domain in Sf9.

The present invention relates to compounds which inhibit, regulate and/or modulate epidermal growth factor receptor (EGFR) activation, as well as compositions which contain these compounds. The invention also provides methods of using the compounds of the instant invention to treat EGFR-activation-dependent diseases and conditions, such as angiogenesis, cancer, tumor growth, atherosclerosis, age related macular degeneration, diabetic retinopathy, and inflammatory diseases. Also included in the present invention are methods for screening for modulators of EGFR activity.

DEFINITIONS

"EGFR" refers to Epidermal Growth Factor Receptor. EGFR is a receptor protein tyrosine kinase belonging to the ErbB receptor family, which includes EGFR (HER1), ErbB2 (HER2), ErbB3 and ErbB4 receptors and other members of this family to be identified in the future. The EGFR receptor will generally comprise an extracellular domain, which may bind an EGFR ligand; a lipophilic transmembrane domain; a conserved intracellular tyrosine kinase domain; and a carboxyl-terminal signaling domain harboring several tyrosine residues which can be phosphorylated. EGFR may be a "native sequence" EGFR or an "amino acid sequence variant" thereof.

A "native sequence" is a sequence of amino acid residues as it is found in nature, without modification by artificial means.

An "amino acid sequence variant" is a naturally occurring or artificially mutated or altered version of a native amino acid sequence.

"EGFR" includes naturally occurring mutant forms, e.g., additions, substitutions and deletions, as well as recombinant forms generated using molecular biology techniques.

An "EGFR molecule" encompasses the amino acid sequence encoding for EGFR. The term also encompasses less than complete fragments of the amino acid sequence, as well as proteins, polypeptides and polypeptide fragments derived from a full-length EGFR protein.

An "EGFR encoding nucleic acid" encompasses the nucleotide sequence encoding for EGFR. The term also encompasses less than full-length nucleotide sequences, as well sequences which have been altered, e.g., mutated with insertions, deletions, and substitutions, and sequences which have been inserted into delivery vehicles, such as recombinant expression vectors.

The "activity" of a polypeptide or protein refers to a functional property associated with that molecule. For example, "EGFR activity" can refer to the tyrosine kinase activity of the molecule as well as the process of dimerization upon binding a ligand. The specific activity associated with a polypeptide or protein can also be identified through a description of a functional process, e.g., phosphorylation.

The terms "EGFR protein" and "EGFR polypeptide" are used interchangeably and encompass full length, wildtype, fragment, variant and mutant EGFR molecules. The terms encompass polypeptides having an amino acid sequence which substantially corresponds to at least one 10 to 50 residue (e.g., 10, 20, 25 30, 35, 40, 45, 50) amino acid fragment and/or a sequence homologous to a known EGFR or group of EGFRs, wherein the EGFR polypeptide has homology of at least 80%, such as at least 81, 82, 83, 84, 85, 86, 87, 88, 89, 90, 91, 92 93, 94, 95, 96, 97, 98, 99 or 100% homology, to the sequence of said known EGFR or group of EGFRs, and exhibits EGFR activity. Encompassed in the present invention is an EGFR polypeptide which is not naturally occurring or is naturally occurring but is in a purified or isolated form which does not occur in nature.

An amino acid or nucleic acid is "homologous" to another if there is some degree of sequence identity between the two. Preferably, a homologous sequence will have at least about 85% sequence identity to the reference sequence, preferably with at least about 90% to 100% sequence identity, more preferably with at least about 91% sequence identity, with at least about 92% sequence identity, with at least about 93% sequence identity, with at least about 94% sequence identity, more preferably still with at least about 95% to 99% sequence identity, preferably with at least about 96% sequence identity, with at least about 97% sequence identity, with at least about 98% sequence identity, still more preferably with at least about 99% sequence identity, and about 100% sequence identity to the reference amino acid or nucleotide sequence.

A "kinase domain" is a region of a polypeptide or protein that shows kinase activity. A kinase domain may be defined in structural terms with reference to an amino acid sequence or to a crystallographic structure.

"EGFR kinase domain molecule" encompasses amino acid sequences corresponding to an EGFR kinase domain. The EGFR kinase domain is a tyrosine kinase domain and in the wildtype human protein is located from amino acid residues 672 to 998. The terms "EGFR kinase domain" and "EGFR kinase domain molecule" are interchangeable and encompass the full wildtype domain, fragments of the domain, as well as mutants and variations of the domain.

A "dimer" is a molecule that comprises two simpler, often identical molecules. When both components (also called "subunits") of a dimer are identical to each other, the dimer can also be referred to as a "homodimer", while a dimer comprising non-identical subunits can be referred to as a "heterodimer". An "EGFR dimer" is a dimer in which at least one subunit corresponds to a member of the ErbB receptor family. "EGFR dimer", "EGFR molecule" and "EGFR protein" can be used interchangeably.

"Dimer formation" encompasses the joining of two subunits to form a dimer. Dimer formation can occur between full-length proteins as well as polypeptides corresponding to a specific epitope or domain of a protein, such as a kinase domain of an EGFR molecule. "Dimer formation" and "dimerization" can be used interchangeably and encompass the activation of an EGFR molecule as well as the coming together and joining of two subunits of an EGFR molecule.

An "asymmetric dimer interface" refers to the region of an EGFR dimer in which the C-lobe of a kinase domain of one subunit is juxtaposed against the N-lobe of a kinase domain of the other subunit.

The term "mutant EGFR" encompasses naturally occurring mutants and mutants created chemically and/or using recombinant DNA techniques. "Mutant EGFR" and "mutant EGFR molecules" can be used interchangeably.

"C-terminal lobe" and "C-lobe" can be used interchangeably and refer to the C-terminal region of an EGFR monomer composed mainly of helical domains (see, e.g. Zhang et al., Cell 125 1137-1149 Jun. 15, 2006).

The term "distal" refers to a location that is a distance away from a reference point. Thus, a residue located "distal from the catalytic domain" is a residue located outside of the defined catalytic domain.

"Modulation" of a protein encompasses changes to either the structure of a protein or to the functional activity of a protein.

A "vesicle assay system" comprises vesicles used to measure a functional activity of a molecule. An exemplary "vesicle" is a closed shell, generally derived from a lipid (e.g., a membrane) by a physiological process or through mechanical means. Preferably, a vesicle comprises one or more types of lipids and has a diameter from about 100 nm to about 200 nm.

"Localizing" and "to localize" (as in "localizing a kinase domain molecule to surface of lipid vesicle") refers to a process of delivering an entity to a specified location, wherein that location is described generally (e.g. "a surface") or specifically (e.g. "to amino acid residue 273").

To be "conjugated" refers to the process or characteristic of being joined. For example, a protein conjugated to a lipid vesicle is joined to that vesicle by means of some kind of interaction, such as a covalent or hydrophobic bond.

A "therapeutic" is a drug or pharmaceutical composition provided to prevent, to alleviate the symptoms of or to cure an illness or disease. An "effective" therapeutic is one which is able to create these effects at a particular concentration.

A "functional assay" is an assay of a functional property of a molecule. For example, a functional assay of a tyrosine kinase may measure the level of phosphorylation upon application of that molecule to a sample. Similarly, "functional effects" refers to changes in a molecule or an action upon a molecule that somehow changes the functional properties of that molecule.

A "tag molecule" (e.g., a "histidine tag") is a molecule added to another molecule to act as an identifier or to modulate a certain property of the attached molecule, such as the ability to bind to yet another molecule. Tag molecules can also be used in methods for purifying or immobilizing the attached molecules.

The "catalytic activity" of a molecule, particularly a protein, refers to the ability of that molecule to increase the rate of a reaction without becoming consumed.

A "hexa-histidine tag" is an epitope tag comprising six histidine amino acid residues in sequence that can serve as a tag without affecting functional properties of the protein to which it is attached.

The term "structural analysis" encompasses techniques used to model the three-dimensional features of a protein, including without limitation X-ray crystallography, computer modeling predictions based on amino acid sequence, and biochemical analysis of protein domain interaction.

"Mig-6", "Mig-6 polypeptide" "Mig-6 protein" can be used interchangeably and encompass the molecule (also known as Gene 33 and RALT) which is known to negatively regulate EGFR activity. Mutation of Mig-6 expression is implicated in EGFR activation-associated cancers (Anastasi et al., 2003; Ferby et al., 2006, Zhang et al., 2006). These terms also encompass fragments of Mig-6.

An "isolated" molecule, such as an isolated polypeptide or isolated nucleic acid, is one which has been identified and separated and/or recovered from a component of its natural environment. The identification, separation and/or recovery are accomplished through techniques known in the art, or readily available modifications thereof.

An "allosteric" mechanism refers to a mechanism of action in which a molecule combines with a site on the protein other than the active site. In an exemplary embodiment, the combination results in a change in the protein's conformation, e.g., at or proximate to the active site.

The term "therapeutically effective amount" refers to an amount of a drug effective to treat, cure, prevent or ameliorate a disease or disorder in a mammal. In the case of cancer, the therapeutically effective amount of the drug may reduce the number of cancer cells; reduce the tumor size, inhibit (i.e., slow to some extent and preferably stop) cancer cell infiltration into peripheral organs, inhibit (i.e., slow to some extent and preferably stop) tumor metastasis, inhibit, to some extent, tumor growth, and/or relieve to some extent one or more of the symptoms associated with the cancer.

"Polypeptide" refers to a polymer in which the monomers are amino acids and are joined together through amide bonds, alternatively referred to as a peptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

As used herein, "amino acid" refers to a group of water-soluble compounds that possess both a carboxyl and an amino group attached to the same carbon atom Amino acids can be represented by the general formula $NH_2$—CHR—COOH where R may be hydrogen or an organic group, which may be nonpolar, basic acidic, or polar. As used herein, "amino acid" refers to both the amino acid radical and the non-radical free amino acid.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A cancer "characterized by excessive activation" of EGFR is one in which the extent of EGFR activation in cancer cells significantly exceeds the level of activation of that receptor in non-cancerous cells of the same tissue type. Such excessive activation may result from overexpression of EGFR and/or greater than normal levels of an EGFR ligand available for activating the EGFR receptor in the cancer cells. Overexpression of EGFR may refer to greater than normal levels of EGFR protein or mRNA. Excessive activation of EGFR may cause and/or be caused by the malignant state of a cancer cell.

Inhibition of EGFR

In one aspect, the present invention provides compositions and method for the modulation of EGFR activation.

In another aspect, the invention provides novel inhibitors of EGFR. In a further aspect, the invention provides inhibitors which act by preventing activation of EGFR. In a still further aspect, the inhibitors prevent formation of an asymmetric dimer interface between EGFR monomers. In such a mechanism of inhibition, the EGFR molecule retains a basal level of activity but is inhibited from activating, i.e. is prevented from prompting the signal transduction cascade that would normally develop upon binding of a ligand to the extracellular activation loop of EGFR (also referred to herein as the "ligand binding region of EGFR"). In one embodiment, the present invention provides inhibitors which bind to the kinase domain of the EGFR molecule, thereby preventing formation of the asymmetric dimer interface, which in turn prevents activation of EGFR.

In a preferred aspect, the invention provides compositions for the inhibition of EGFR, wherein those compositions comprise molecules which prevent formation of an asymmetric dimer interface between EGFR monomers. Such molecules include polypeptides, small molecules, peptidomimetics, and other molecules and compositions which are able to prevent formation of the asymmetric dimer interface. In a further embodiment, the inhibitors of the invention comprise isolated polypeptides. In a still further embodiment, the isolated polypeptides comprise the Mig-6 protein and/or fragments of Mig-6, as is discussed more fully below.

In a preferred aspect, the invention provides a pharmaceutical composition comprising one or more isolated polypeptides with an amino acid sequence selected from SEQ ID NOs: 1-9, wherein said one or more polypeptides are combined with at least one pharmaceutically acceptable carrier. In one embodiment, the isolated polypeptides are inhibitors of EGFR. In a further embodiment, the pharmaceutical composition is administered to patients diagnosed with illnesses associated with EGFR. Administration of such a pharmaceutical composition is accomplished using techniques known in the art and those described herein.

Mig-6

Mig-6, which is also identified as Gene 33 and RALT, is known to negatively regulate EGFR activity and mutation or loss of Mig-6 expression is implicated in EGFR activation-associated cancers. There is evidence to suggest that Mig-6 inhibits EGFR via an allosteric mechanism. (Zhang et al., (2006) *Cell*, Vol. 125: 1137-49). The present invention thus provides novel inhibitors of EGFR activation which are derived from the Mig-6 protein.

In a preferred aspect of the invention, Mig-6, or fragments of Mig-6, are expressed in and purified from *E. coli*. A minimum epitope for EGFR binding has a sequence which comprises SEQ ID NO: 2. In one embodiment, the invention provides an allosteric inhibitor of EGFR activation, where the inhibitor is an isolated polypeptide comprising an amino acid sequence selected from SEQ ID NOs 1-9.

In another aspect of the invention, a 25-mer peptide corresponding to residues 340-364 in Mig-6 (SEQ ID NO: 4) is synthesized. Such a peptide can inhibit activated EGFR kinase at an IC50 of ~100 µM, suggesting that the 25-mer peptide does not comprise the entire binding epitope. A crystal structure of the 25-mer peptide crystallized with the EGFR kinase domain identifies the region of the peptide bound to the kinase as containing 16 residues: MPPTQSFAPDPKYVSS (SEQ. ID NO: 5).

Figure 5:
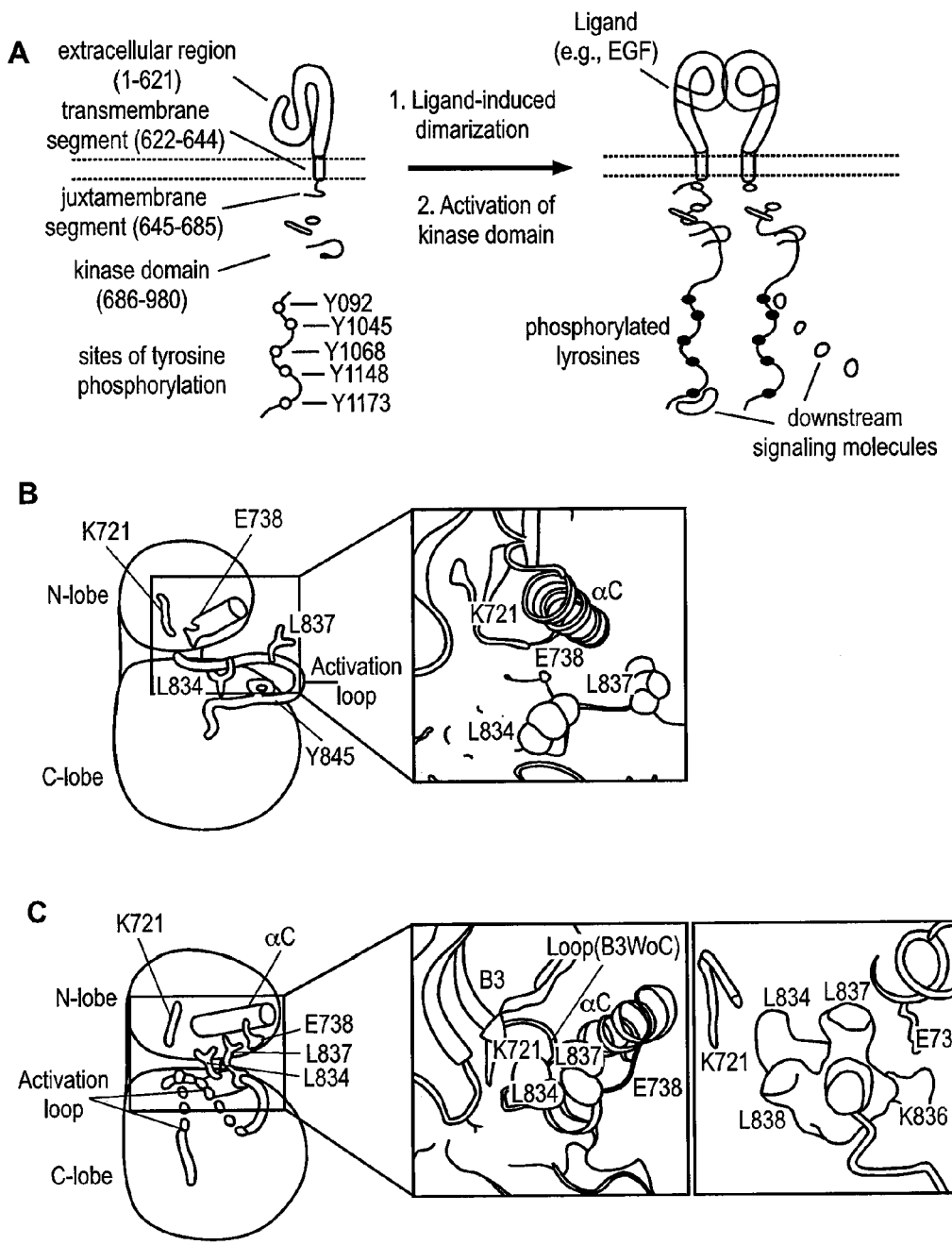
FIG. 5 shows a general view of ligand-induced dimerization and activation of EGFR (A), and a detailed view of the catalytic site of EGFR kinase domain in the active (B) and inactive (C) conformation.

In another aspect of the invention, a 40-mer peptide comprising amino acid sequence SEQ ID NO: 3 is synthesized. The 40-mer peptide is much more potent than the 25-mer peptide in inhibiting the activated EGFR kinase, with an IC50~10 µM. A crystal structure of the complex of the EGFR kinase domain and the 40-mer peptide has improved resolution (~2.9 Å) and can be used, similar to the description above for the 25-mer peptide, to identify residues of interaction between the peptide and the kinase domain. (FIG. 5).

Figure 4:
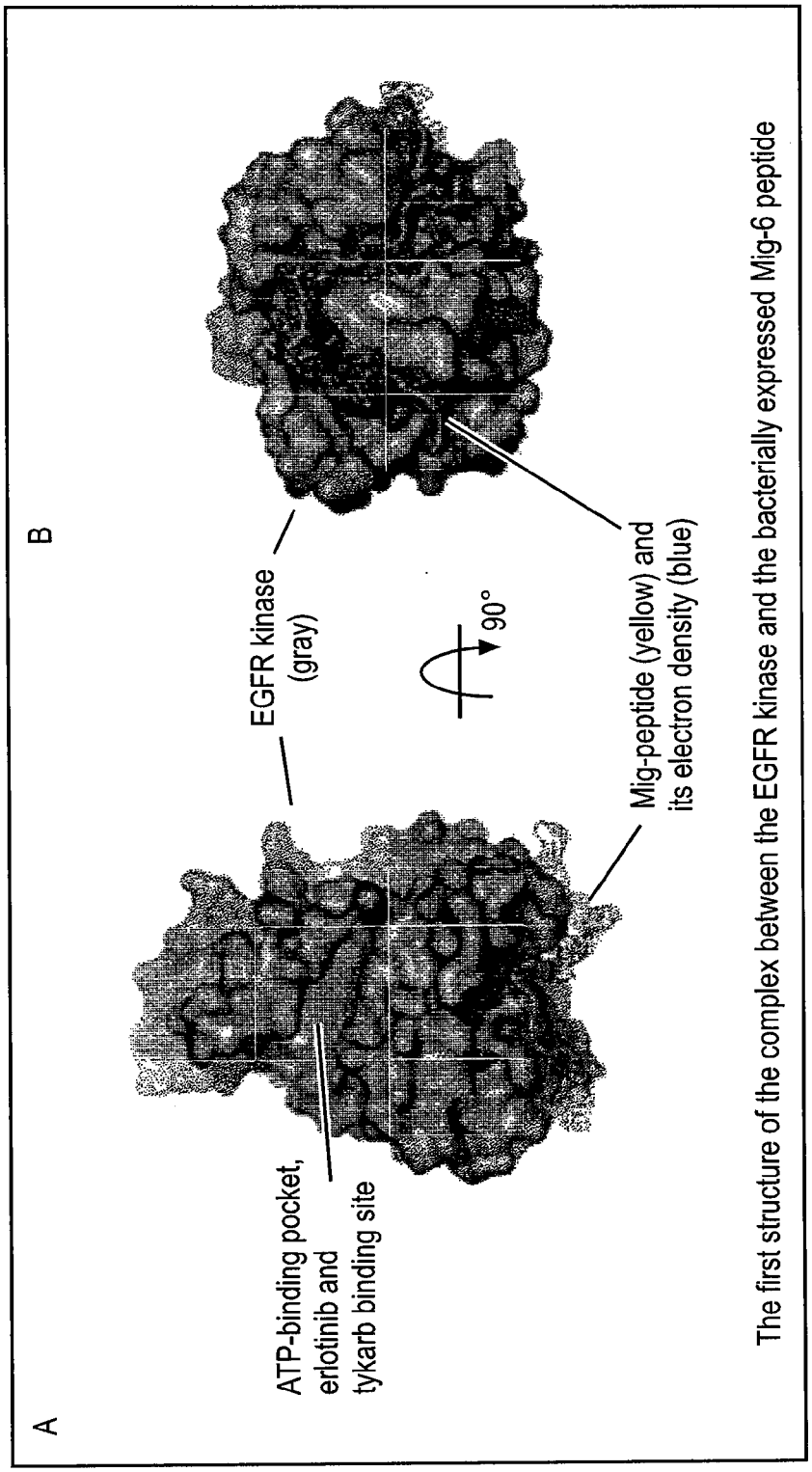
FIG. 4 A-B is a crystal structure of a complex between EGFR kinase domain and the bacterially expressed Mig-6 peptide.

The Mig-6 peptide binds the EGFR kinase domain by wrapping around a shallow groove on the surface of the base of the kinase domain (FIG. 4). At this face of the kinase domain, a number of conserved nonpolar residues form a hydrophobic surface which interacts specifically with the N-lobe of the other kinase upon the formation of the asymmetric activating kinase dimer. Several hydrophobic residues in the Mig-6 peptide pack tightly against this hydrophobic surface in the C-lobe of the kinase, preventing the formation of the asymmetric dimer and thus inhibiting EGFR kinase activation.

In one aspect of the invention, the binding affinity of a peptide to the EGFR kinase domain is improved by modifying the peptide sequence to more tightly interact with the hydrophobic surface in the C-lobe of the kinase domain. In one embodiment, the peptide sequence is modified with reference to the residues of interaction between the EGFR kinase domain and a Mig-6 polypeptide comprising an amino acid sequence comprising SEQ ID NOs: 1-5.

In another aspect of the invention, small molecule mimics of the Mig-6 peptide are designed which bind to the kinase at the same structural features shown in the crystal structures. Such peptides and small molecules can be developed into new classes of EGFR-antagonizing drugs for cancer therapy in accordance with the present invention.

Mig-6 and EGFR kinase domains are expressed and purified according to techniques known in the art and as described herein (see Example I).

In another aspect, the invention provides a method of treatment for cancer, where the treatment involves (1) determining the types of EGFR molecules expressed in tumor cells associated with the cancer, and (2) administering one or more inhibitors that are able to interact with the types of EGFR molecules identified in step (1). In one embodiment, the inhibitors are peptides, peptidomimetics, small molecules, and other molecules and compositions which are able to prevent formation of the asymmetric dimer interface between EGFR monomers. In a preferred embodiment, the EGFR inhibitors are isolated polypeptides which are able to bind to the kinase domain of the identified EGFR molecules, thereby preventing formation of the asymmetric dimer interface. In a further embodiment, the isolated polypeptides comprise D-, L-, and unnatural isomers of amino acids. In a still further embodiment, the isolated polypeptides have at least 70% sequence identity to SEQ ID NOs: 1-9.

In a further aspect, methods for treating cancer with EGFR inhibitors are provided, wherein the treatment prevents the excessive or uncontrolled cell growth that can lead to the development of tumors. Tumors suitable for treatment within the context of this invention include, but are not limited to, breast tumors, gliomas, melanomas, prostate cancer, hepatomas, sarcomas, lymphomas, leukemias, ovarian tumors, thymomas, nephromas, pancreatic cancer, colon cancer, head and neck cancer, stomach cancer, lung cancer, mesotheliomas, myeloma, neuroblastoma, retinoblastoma, cervical cancer, uterine cancer, and squamous cell carcinoma of skin. Many known cell surface receptors are generally preferentially expressed in tumors, and ligands for these receptors can be used to inhibit the progression and development of tumor cells. Such ligands can include known ligands for the receptors, molecules and compounds that are identified using methods of the invention as being able to interact with such receptors, as well as ligands specifically designed and developed for particular receptors—such as by raising antibodies to the receptors and by designing novel molecules with structures that allow interaction with particular receptors.

Through delivery of the compositions of the present invention, unwanted growth of cells may be slowed or halted, thus ameliorating the disease. This treatment is suitable for warm-blooded animals: mammals, including, but not limited to, humans, horses, dogs, and cats, and for non-mammals, such as avian species. Methods of treating such animals with compositions of the present invention are provided herein.

EGFR and Disease

The compounds of the present invention are in one aspect provided for the treatment of disorders in which aberrant expression ligand/receptor interactions or activation or signaling events related to EGFR are involved. Such disorders may include those of neuronal, glial, astrocytal, hypothalamic, and other glandular, macrophagal, epithelial, stromal, and blastocoelic nature in which aberrant function, expression, activation or signaling of EGFR is involved. In an additional aspect, the compounds of the present invention may have therapeutic utility in inflammatory, angiogenic and immunologic disorders involving both identified and as yet unidentified EGFRs and other tyrosine kinases that are inhibited by the compounds of the present invention.

In one aspect, the invention provides a method for the treatment of abnormal cell growth in a mammal which comprises administering to said mammal an amount of a compound or composition, or a pharmaceutically acceptable salt, solvate or prodrug thereof, that is effective in treating abnormal cell growth. This treatment can in an exemplary embodiment be administered in combination with another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. In one embodiment, the invention provides a pharmaceutical composition for treating abnormal cell growth wherein the composition includes a compound which inhibits EGFR activation, or a pharmaceutically acceptable salt, solvate or prodrug thereof, that is effective in treating abnormal cell growth, and another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

EGFR is frequently overexpressed in cancer. (Mendelsohn et al., (2006) Semin Oncol. 33(4):369-85). Arthritis, hypersecretory respiratory diseases, and skin conditions such as psoriasis are also associated with EGFR overexpression and activation. Accordingly, a preferred aspect of the instant invention provides methods and compositions for the inhibition of EGFR, wherein said inhibition serves as a treatment for EGFR-associated diseases such as cancer and arthritis. In a particularly preferred embodiment, the invention provides methods and compositions for the inhibition of EGFR in which said methods and compositions prevent the formation of an asymmetric dimer interface.

With regard to cancer, two of the major hypotheses advanced to explain the excessive cellular proliferation that drives tumor development relate to functions known to be kinase regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include growth factor receptors such as EGFR. It is thus a preferred aspect of the present invention to provide a cancer treatment in which a composition of the invention that is able to prevent the cell division and/or differentiation processes that lead to malignant cell growth of cancer. Such a cancer treatment, in a preferred embodiment, halts or slows down cell division and/or differentiation by preventing formation of the EGFR asymmetric dimer interface, thereby preventing the intracellular second messenger cascade that takes place upon activation of an EGFR dimer by intermolecular interaction or by activation upon binding of an extracellular ligand.

For patients with lung cancer, the EGFR inhibitor Erlotinib increases survival times by several months (Bezjak et al., (2006) Journal of Clinical Oncology, Vol. 24(24): 3831-7). In vitro studies have shown that another EGFR inhibitor, the drug gefitinib (marketed as Iressa), is able to halt the growth of cancer cells in colon cancer (Azzariti et al., (2006) World Journal of Gastroenterol, Vol. 12(32): 5140-7 Wiedmann et al., (2006) Anticancer Drugs, Vol. 17(7): 783-95.), and biliary tract cancer (Wiedmann et al., (2006) Anticancer Drugs, Vol. 17(7): 783-95). Gefitinib has also been shown to increase apoptosis of gastric cancer cells (Rojo et al., (2006) Journal of Clinical Oncology, Vol. 24(26): 4309-16). Erlotinib and gefitinib have both been shown to be effective as part of combination therapies, in which the synergistic effects of the EGFR inhibitors combined with radiotherapy significantly improved outcomes over those seen with radiotherapy alone (Park et al., (2006) Cancer Research, Vol. 66(17): 8511-19). Lapatinib, another EGFR inhibitor, is currently in Phase III clinical trials for treatment of breast cancer (Johnston et al., (2006) Drugs of Today, Vol. 42(7): 441-53). Studies have also shown that EGFR inhibitors can be used to treat, ameliorate and prevent illnesses not associated with cancer. For example, EGFR inhibitors have been shown to prevent parathyroid hyperplasia, which is the cause of parathyroid gland enlargement in kidney disease (Dusso et al., (2006) Kidney International Supplement, Vol. 102: S8-11).

Other pathogenic conditions which have been associated with tyrosine kinases such as EGFR include, without limitation, psoriasis, hepatic cirrhosis, diabetes, angiogenesis, restenosis, ocular diseases, rheumatoid arthritis and other inflammatory disorders, immunological disorders such as autoimmune disease, cardiovascular disease such as atherosclerosis and a variety of renal disorders. Thus, in a preferred aspect of the invention, compositions and methods are provided for the treatment of these EGFR-associated diseases, in which one exemplary embodiment of the invention treats, prevents, ameliorates, or cures the disease by preventing uncontrolled cell differentiation and proliferation.

In another aspect of the invention, compositions and methods are provided for the treatment, amelioration, and prevention of angiogenesis-dependent diseases. In these diseases, vascular growth is excessive or allows unwanted growth of other tissues by providing blood supply. These diseases include angiofibroma, arteriovenous malformations, arthritis, atherosclerotic plaques, corneal graft neovascularization, delayed wound healing, diabetic retinopathy, granulations due to bums, hemangiomas, hemophilic joints, hypertrophic scars, neovascular glaucoma, nonunion fractures, Osler-weber syndrome, psoriasis, pyogenic granuloma, retrolental fibroplasia, scleroderma, solid tumors, trachoma, and vascular adhesions.

By inhibiting vessel formation (angiogenesis), unwanted growth may be slowed or halted, thus ameliorating the disease. In a normal vessel, a single layer of endothelial cells lines the lumen. Growth of a vessel requires proliferation of endothelial cells and smooth muscle cells, which is often dependent on EGFR activation. As such, the present invention provides compositions and methods for the inhibition of EGFR activation.

In a further embodiment, the present invention provides compounds for the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse. Chemoprevention may be accomplished in accordance with the present invention by administering compositions described herein to a patient using methods and techniques known in the art and as described herein. In a still further embodiment, chemoprevention is accomplished using the compositions of the present invention alone, in a pharmaceutical formulation or salt, and in combination with one or more other anti-cancer and/or anti-tumor agents.

Formulations and Administration

The compositions of the present invention may in an exemplary embodiment be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

A compound of the present invention or a physiologically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

As used herein, "administer" or "administration" refers to the delivery of a compound or salt of the present invention or of a pharmaceutical composition containing a compound or salt of this invention to an organism for the purpose of prevention or treatment of an EGFR-related disorder.

Suitable routes of administration may include, in an exemplary embodiment without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration are oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping, lyophilizing processes or spray drying.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such buffers with or without a low concentration of surfactant or co-solvent, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores.

Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

In one embodiment, the invention provides dragee cores with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono- di- or triglycerides. Stabilizers may be added in these formulations, also.

For administration by inhalation, compounds for use according to the present invention may in an exemplary embodiment be conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g. by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water with or without additional surfactants or cosolvents such as POLYSORBATE 80, Cremophor, cyclodextrin sulfobutylethyl, propylene glycol, or polyethylene glycol e.g., PEG-300 or PEG 400, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the EGFR modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, citrate, mesylate, lactate, tartrate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide ($Ca(OH)_2$), etc.).

It is also an aspect of this invention that a compound described herein, or its salt, is combined with other chemotherapeutic agents for the treatment of the diseases and disorders discussed above. In an exemplary embodiment, a compound or salt of this invention is combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

In a further embodiment, a compound or salt of this invention is provided in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

In another embodiment, a compound or salt of this invention is provided in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound or salt of this invention may in an exemplary embodiment be used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors (such as anastrozole).

In another embodiment, a combination of a compound of this invention is provided in combination with Camptosar™, Gleevec™, Herceptin™, Endostatin™, Cox-2 inhibitors, Mitoxantrone™ or Paclitaxel™ for the treatment of solid tumor cancers or leukemias such as, without limitation, acute myelogenous (non-lymphocytic) leukemia.

Dosage

Pharmaceutical compositions suitable for use in the present invention include compositions wherein the active ingredients are contained in an amount sufficient to achieve the intended purpose, i.e., the modulation of EGFR activity or the treatment, amelioration or prevention of an EGFR-related disorder, such as cancer.

More specifically, a therapeutically effective amount means an amount of compound effective to prevent, alleviate or ameliorate symptoms of disease or prolong the survival of the subject being treated. For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of EGFR activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See, e.g., Fingl, et al., (1975), *The Pharmacological Basis of Therapeutics*, Ch. 1 p. 1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50 to 90% inhibition of a kinase may be ascertained using the assays described herein. Preferably, the dosages necessary to achieve the MEC will depend on individual characteristics and route of administration. HPLC assays or bioassays can be used to determine plasma concentrations.

Dosage intervals can also be determined using MEC values. Compounds can in an exemplary embodiment be administered using a regimen that maintains plasma levels above the MEC for 10 to 90% of the time, preferably between 30 to 90% and most preferably between 50 to 90%. In cases of local administration or selective uptake, the effective local concentration of the drug may not be related to plasma concentration and other procedures known in the art may be employed to determine the correct dosage amount and interval.

The amount of a composition administered will, of course, depend on the subject being treated, the severity of the affliction, the manner of administration, the judgment of the prescribing physician, etc.

Mechanisms of Action

Inhibition of EGFR can occur through a variety of mechanisms. For example, many of the traditionally used anti-EGFR agents exert their effects on EGFR either by binding to the ATP site of the EGFR kinase domain or by down-regulating expression of EGFR to reduce the level of proteins present in cell membranes (Cunningham et al., (2006) *Cancer Research*, Vol. 15: 7708-15).

The present invention provides novel methods and compositions for inhibition of EGFR, wherein that inhibition occurs by an allosteric mechanism. In contrast to the compositions and methods of the current invention, most currently used therapeutics, such as Erlotinib and Lapatinib, bind directly to the active (ATP-binding) site of the EGFR protein or interfere with the extracellular ligand binding domain. (Lenz, (2006) *Oncology*. Williston Park, N.Y., Vol. 20, (5 Suppl. 2): 5-13). The present invention relates to compositions and methods in which EGFR activation is modulated through an allosteric mechanism, preferably by preventing the formation of an asymmetric dimer interface between the monomers forming the EGFR dimer.

In one embodiment, the invention provides one or more isolated polypeptides which bind to a kinase domain of an EGFR molecule. In a preferred embodiment, the isolated polypeptides inhibit EGFR activation by preventing the formation of an asymmetric dimer interface between EGFR molecules.

The cytoplasmic EGFR kinase domain corresponds to amino acid residues 672-998 of the human EGFR polypeptide. Studies of EGFR mutants in which the kinase domain has been altered indicates that the kinase domain is an important factor in the survival of cancer cells. (Haber, (2005) *Cold Spring Harbor Symposia Quantitative Biology*, Vol. 70: 419-26).

Figure 8:
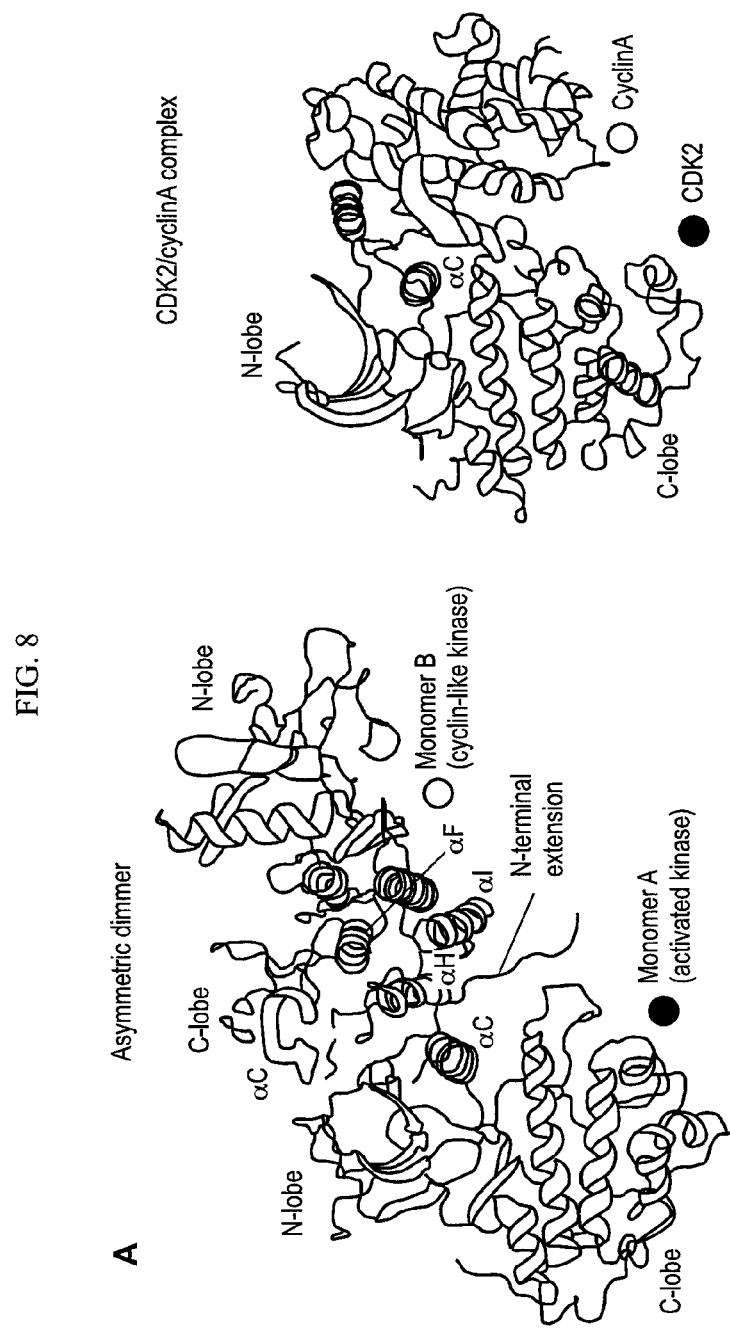
FIG. 8 shows a crystal structure of the asymmetric dimer interface of the EGFR kinase domain.
Figure 8:
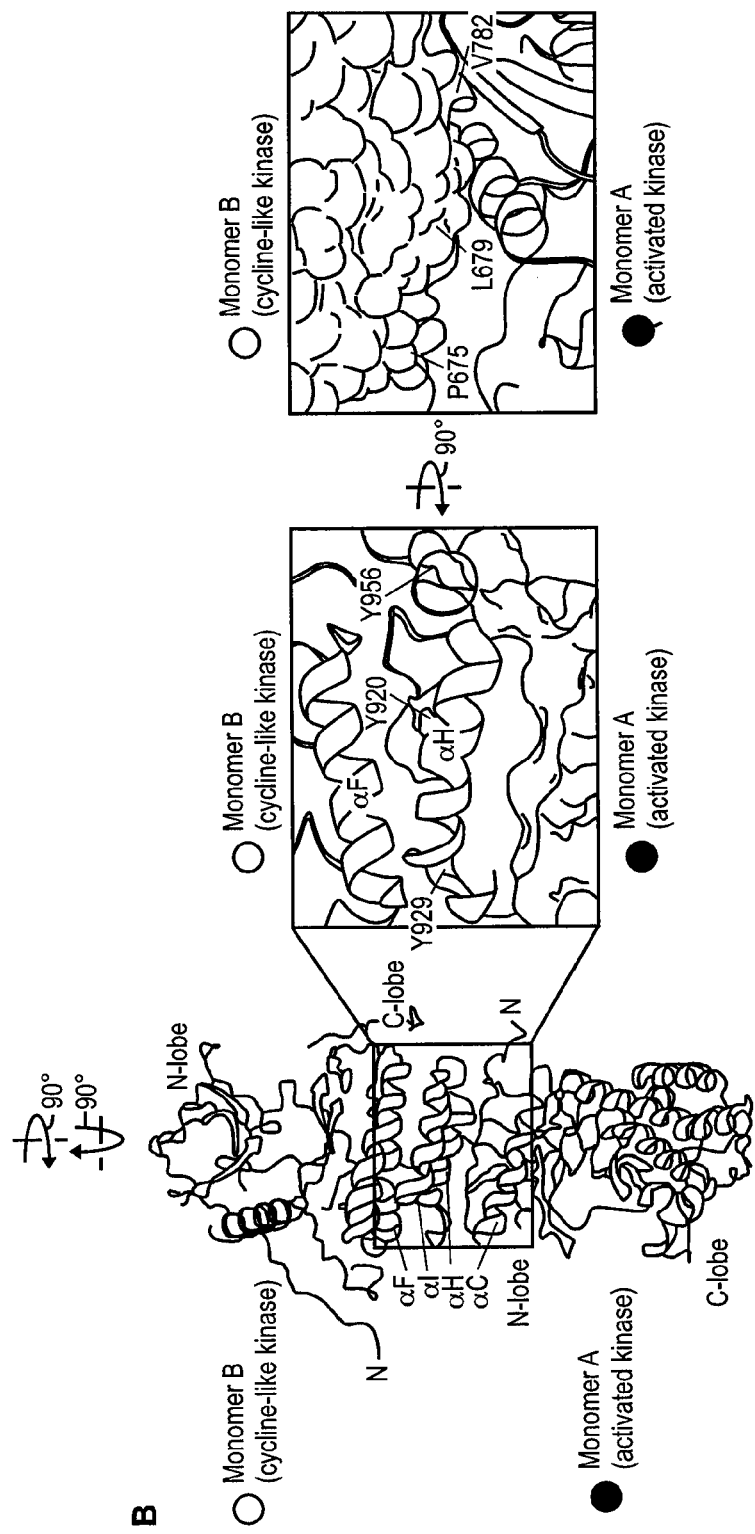

The asymmetric dimer interface is formed by the N-terminal extension (residues 672-685), the C helix, and the loop between strands β4 and β5 of monomer A (the activated kinase domain) and the loop between helices αG and αH, helix αH, and the end of helix αI from monomer B, burying ~2019 Å$^2$ of surface area between them (FIG. 8).

Figure 9:
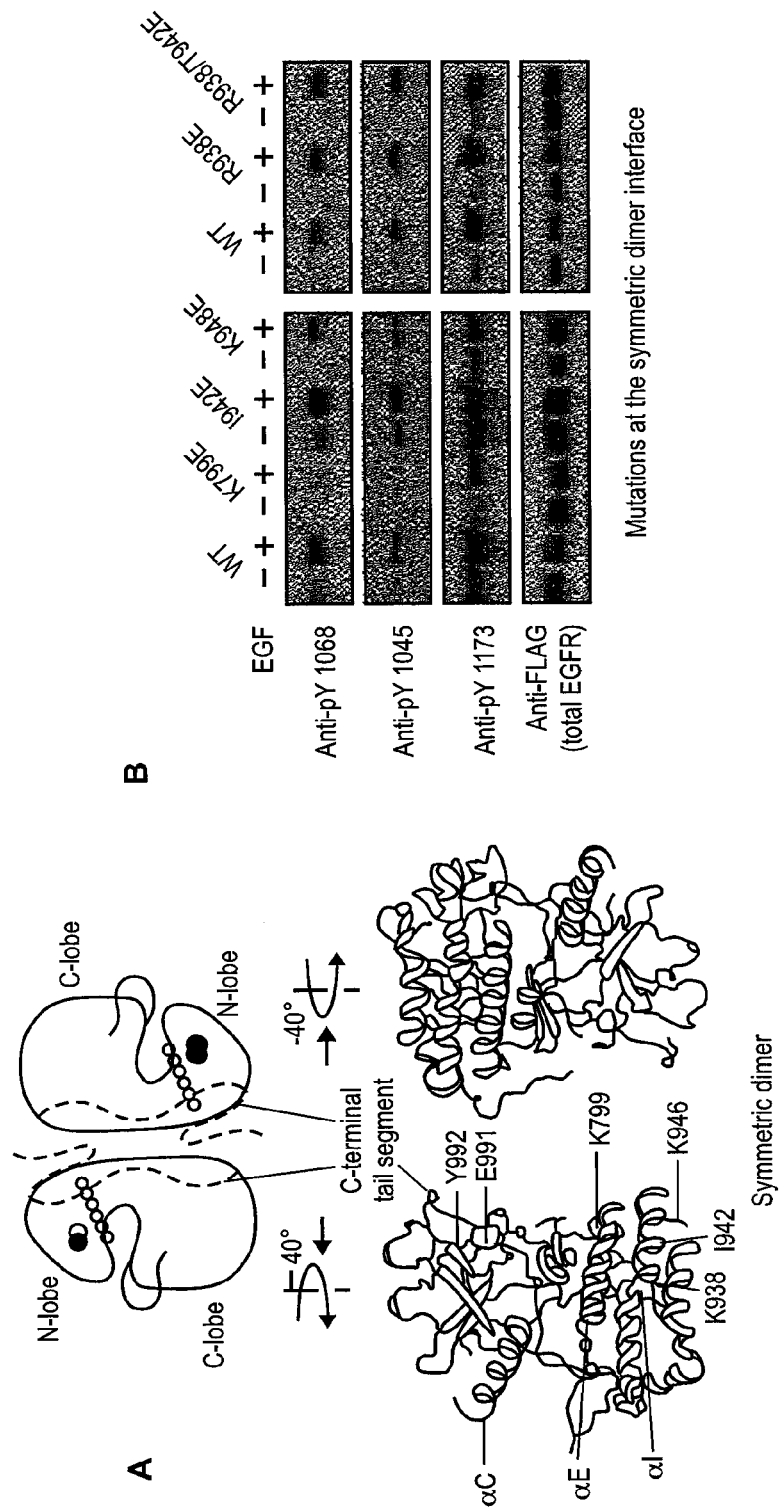
FIG. 9 displays information regarding the symmetric dimer interface.

The symmetric dimer interface seen in most crystal structures of the EGFR kinase domain does not play a significant role in the activation of EGFR. A cell transfection assay in which the levels of phosphorylation at three sites in the C-terminal tail of the full-length receptor (Tyr1045, Tyr1068, and Tyr1173) were monitored showed that mutations at the symmetric dimer interface have no effect on the ability of the dimer to activate. (FIG. 9). As described herein, a cell transfection assay includes the monitoring of phosphorylation at specific tyrosine residues using anti-EGFR antibodies. (see, Example V).

Figure 12:
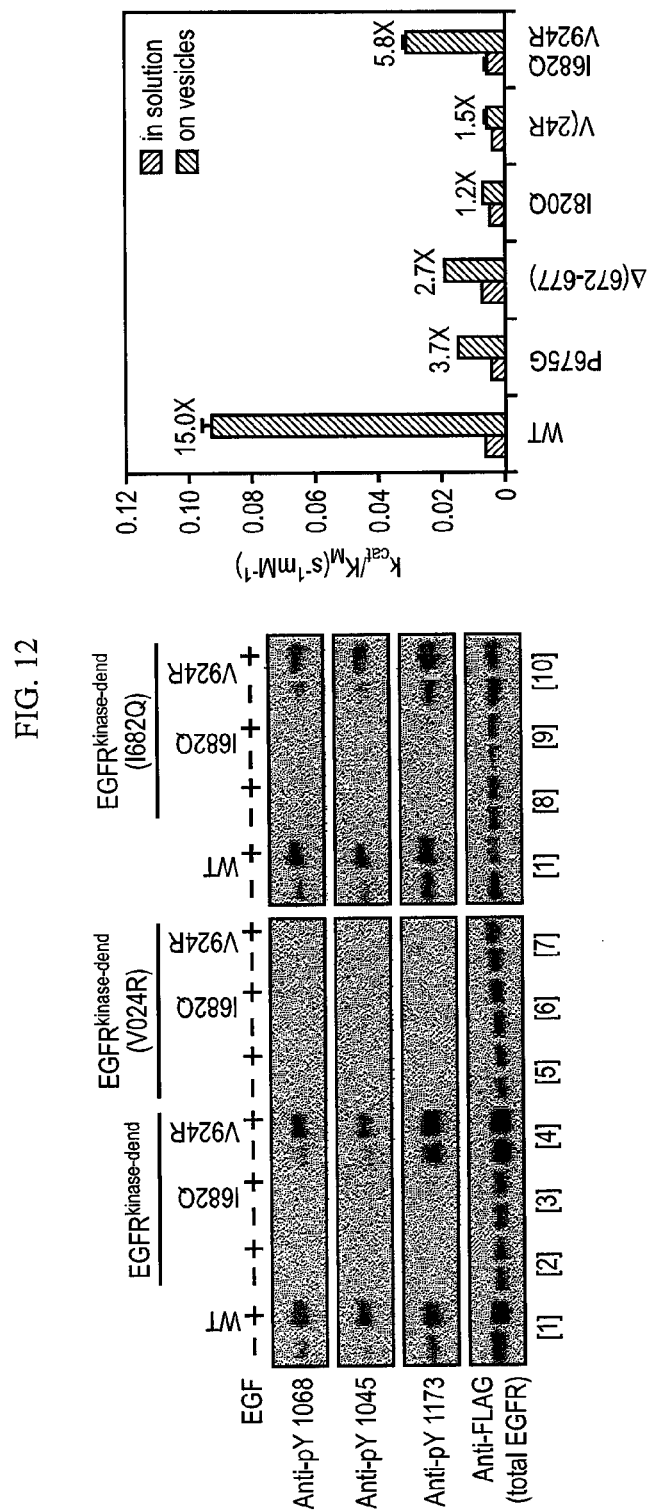
FIG. 12 shows the results of a phosphorylation assay of various transfection/cotransfection experiments (left panel) and the effects of mutations in the asymmetric dimer interface on the catalytic activity of the kinase domain in solution and attached to lipid vesicles (right panel).
Figure 13:
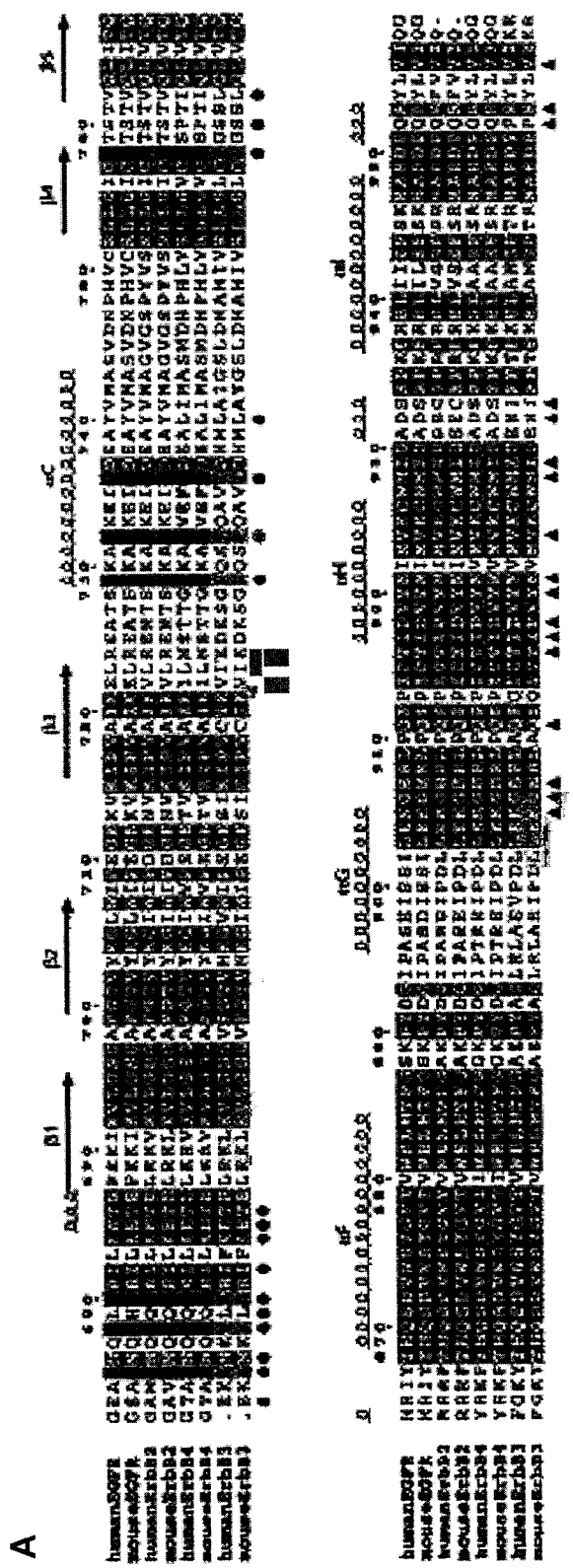
FIG. 13 is a sequence alignment of EGFR family members from human and mouse. Residues in the N-lobe faces are denoted by ovals, and residues in the C-lobe faces are denoted by triangles. SEQ ID NO: 10 and SEQ ID NOS. 14-21.
Figure 14:
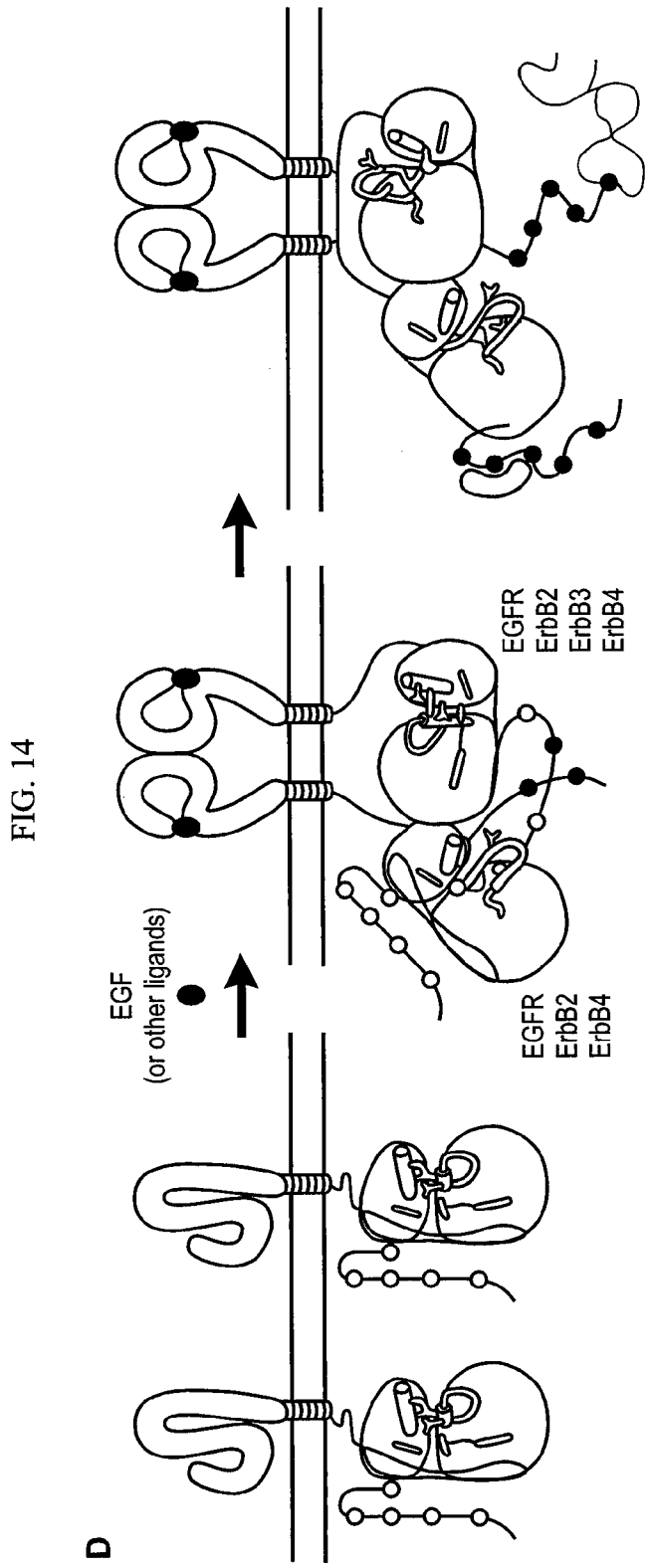
FIG. 14 is a general model of the activation mechanism for the EGFR family receptor tyrosine kinases.
Figure 19:
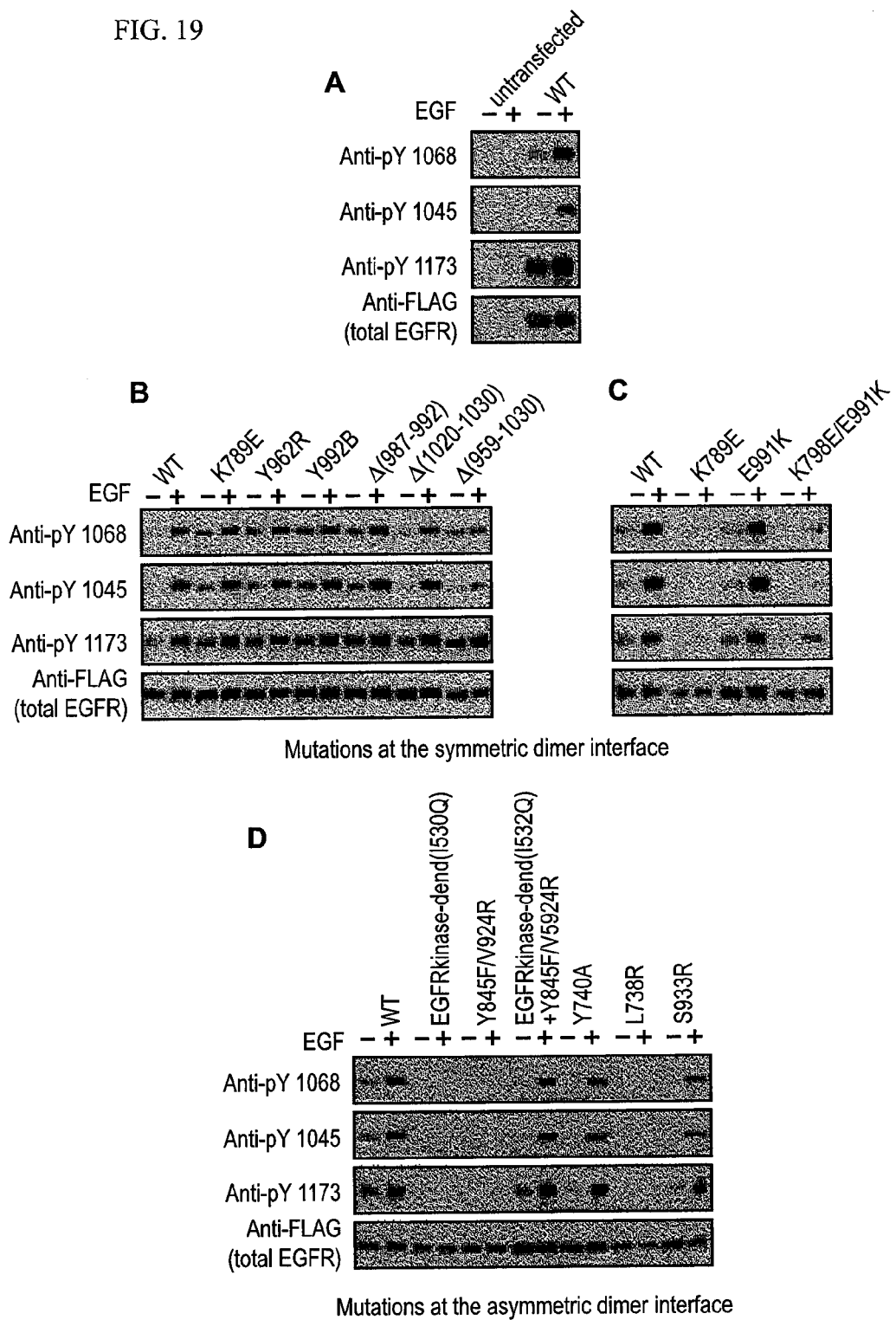
FIG. 19 A-D shows the results of a phosphorylation assay of wildtype and mutant EGFR kinase domains.
Figure 20:
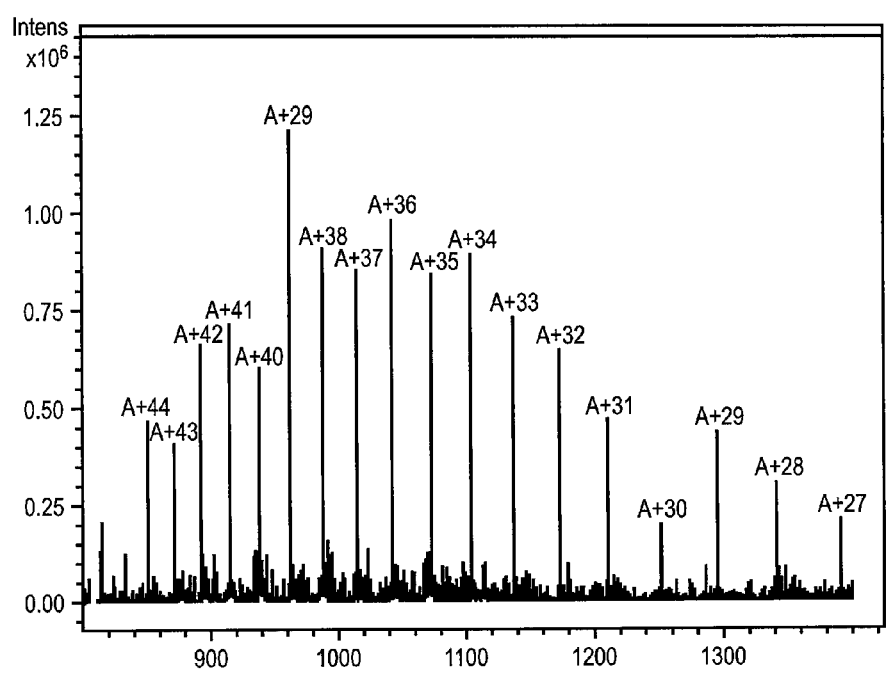
FIG. 20 shows data from a mass spectrum analysis of the Y845F mutant EGFR kinase domain.
Figure 21:
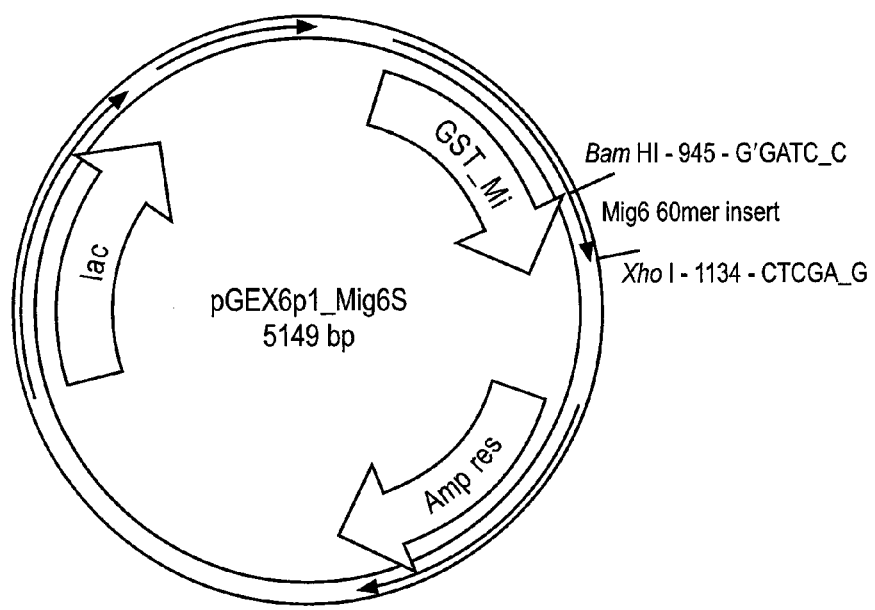
FIG. 21 shows the vector map for the Mig-6 expression vector construct.

In contrast to the symmetric dimer interface, the asymmetric EGFR dimer interface is vital to the activation of EGFR. Mutation of residues at the asymmetric dimer interface affects auto-phosphorylation of full-length EGFR. Such mutations include P675G, L680A, I682Q, and L736R, which involve residues which are contributed to the interface by monomer A (the activated kinase—see FIG. 8). Additional mutations include I917R, M921R, V924R, and M928R, which involve residues that are contributed to the interface by monomer B (the cyclin-like partner). These mutations diminished the ability of EGFR to phosphorylate three tested auto-phosphorylation sites, either before or after EGF stimulation (FIG. 12 and FIG. 19). A double mutant containing both a C-lobe face mutation and a mutation that replaces the activation loop tyrosine with phenylalanine (Y845F/V924R) showed no significant auto-phosphorylation in a cell transfection assay, but autophosphorylation was rescued by cotransfection with the EGFR$^{kinase-dead}$ (I1692Q) mutant. (FIG. 19). These data demonstrate that activation of the receptor is dependent on formation of the asymmetric dimer interface rather than on phosphorylation of the tyrosine residue in the activation loop. The present invention relates to the modulation and interference with this asymmetric dimer interface.

Allosteric Model

An allosteric model predicts that since the dimer interface is asymmetric, an EGFR molecule with a mutation in the C-lobe face of the dimer interface can be activated by another EGFR molecule that has an intact C-lobe interface. Conversely, an EGFR molecule with a mutation in the N-lobe face of the dimer interface (i.e., one that is predicted to be resistant to activation) can act as an activator for another EGFR molecule in which the N-lobe face is intact.

Figure 11:
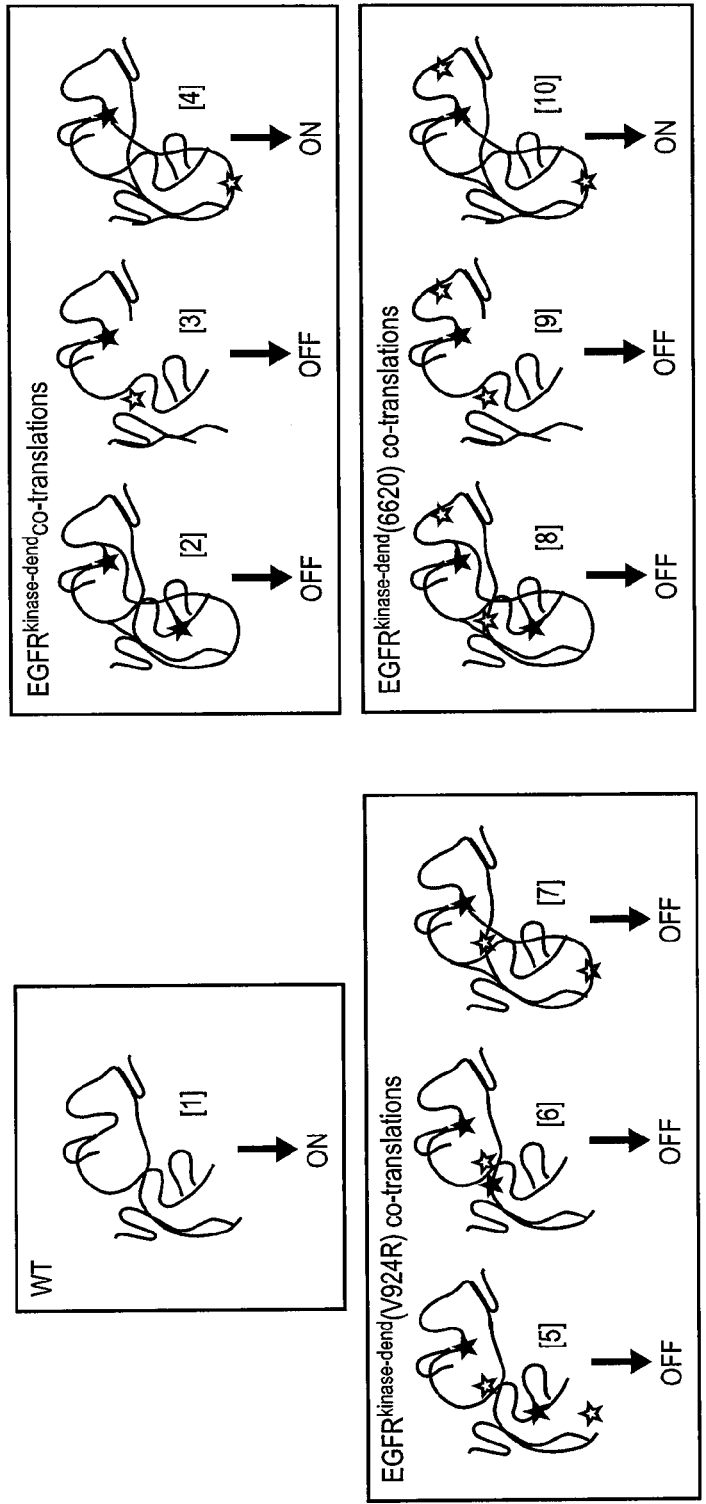
FIG. 11 is a schematic model of predicted outcomes of various transfection/cotransfection experiments.

One way to test such a theory is to construct a catalytically dead variant of EGFR in which Asp813 is replaced by asparagine. Asp813 is part of the catalytic base in the kinase domain. Transfection of cells with the "dead" kinase shows that it does not undergo auto-phosphorylation either before or after EGF stimulation (FIG. 11).

Figure 10:
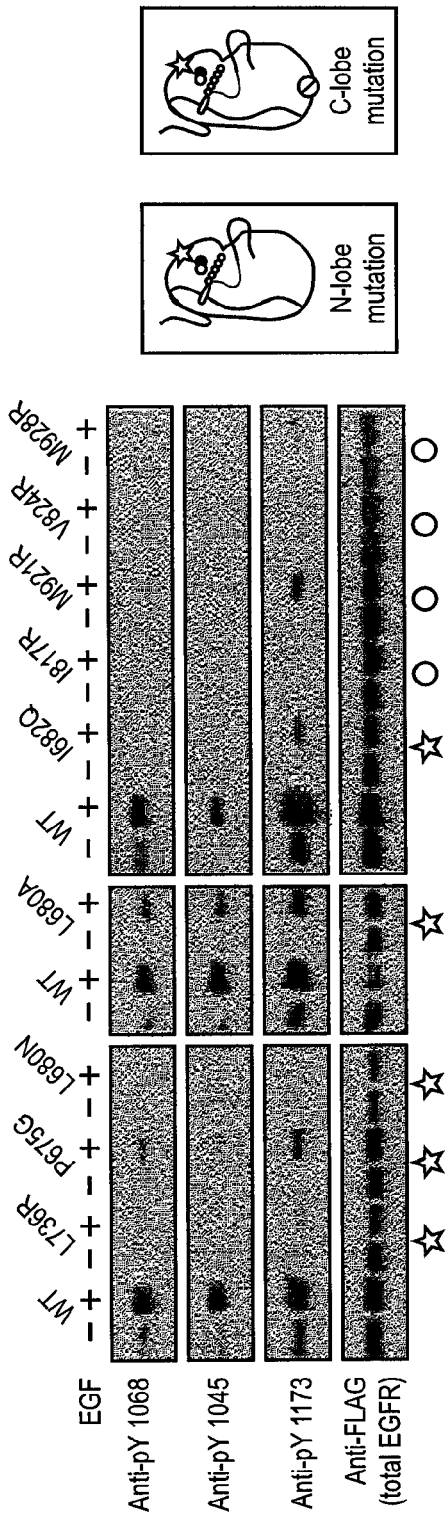
FIG. 10 shows results of a phosphorylation assay of the wildtype dimer and of mutant constructs with mutations in the N-lobe and C-lobe face of the dimer interface.

Co-transfection of the dead EGFR with EGFR(I682Q), an N-lobe mutant, does not result in detectable levels of auto-phosphorylation (FIG. 10). In contrast, co-transfection of the dead EGFR with EGFR(V924R) results in robust levels of auto-phosphorylation (FIG. 19). In this case, the EGFR (V924R), a catalytically active C-lobe mutant, has an intact N-lobe face. Although this mutant cannot stimulate itself because of the disrupted C-lobe face, it can be stimulated by the intact C-lobe of the dead EGFR (FIG. 19).

It can be shown that a double mutant, EGFR(Asp813Asx) (I682Q) rescues the auto-phosphorylation of EGFR(V924R) because it has an intact C-lobe that can interact with the intact N-lobe of EGFR(V924R) (FIG. 19). Also consistent with an allosteric model is the inability of EGFR(Asp813Asx) (I682Q) to rescue auto-phosphorylation of EGFR(I682Q) (FIG. 10). In this case, both transfected EGFR molecules have defective N-lobe faces (FIG. 10). Likewise, a double mutant EGFR(Asp813Asx) (V924R), which has a defective C-lobe face, fails to rescue the auto-phosphorylation of either EGFR (I682Q) or EGFR(V924R). (FIG. 10). These results support an allosteric model of activation for the EGFR protein in which the asymmetric dimer interface must form for activation to occur.

Thus, in a preferred aspect, the invention provides inhibitors of EGFR which act at a site other than the active site to allosterically prevent activation of the protein. In a preferred embodiment, this inhibition occurs by preventing the formation of an asymmetric dimer interface between EGFR monomers. Preventing the formation of the asymmetric dimer interface is able to inhibit EGFR, because the interface is vital to the allosteric mechanism of EGFR activation.

Vesicle Assay System

In one aspect, the invention provides methods for screening for inhibitors of EGFR activation. In a preferred embodiment, these screening methods are able to identify allosteric inhibitors of EGFR.

In a preferred aspect of the invention, a vesicle assay system is used to screen for inhibitors of EGFR activation.

The EGFR kinase domain is monomeric in solution at concentrations up to 50 µM (FIG. 15). The local concentration of kinase domains in a dimeric receptor is estimated to be in the millimolar range. In order to increase the local concentration of the kinase domain in a controlled fashion, one aspect of the invention provides a hexa-histidine tag for the kinase domain to localize it to the surface of vesicles, such as small unilamellar vesicles containing lipids with a nickel-nitrilotriacetate head group (1,2-Dioleoyl-sn-Glycero-3 {[N (5-Amino-1-Carboxypentyl)iminodiAcetic Acid]Succinyl} Nickel salt, DOGS-NTA-Ni). The density of the kinase domain on individual vesicles can be controlled, for example, by varying the mole ration of the DOGS-NTA-Ni lipids and the 1,2-Dioleoyl-sn-Glycero-3-Phosphocholine (DOPC) lipids that constituted the vesicles.

The density of DOGS-NTA-Ni lipids in the vesicles is in one embodiment varied from 0.5 to 5.0 mole percent. The dissociation constant for attachment of the His-tagged kinase domain to the vesicle is estimated to be ~2 µM and the total concentration of DOGS-NTA-Ni lipids is in a preferred embodiment maintained at 12.5 µM to ensure localization of His-tagged protein to the vesicles. The effective local concentration of kinase domains in such a system is in a preferred embodiment approximately in the range of ~0.4 mM (for 100 nm vesicles containing 0.5 mole % DOGS-NTA-Ni) to ~4 mM (for 5 mole % DOGS-NTA-Ni).

In one aspect of the invention, a method utilizing a vesicle assay system is provided for screening for potential inhibitors of EGFR activation. In this method, an isolated polypeptide corresponding to an EGFR kinase domain is attached to the surface of a vesicle, which is in an exemplary embodiment a lipid vesicle. This attachment forms a conjugated polypeptide. In an exemplary embodiment, the activity of the conjugated polypeptide is determined using techniques known in the art, such as Western blot analysis. The conjugated polypeptide is then contacted with a test compound, and the activity of the conjugated polypeptide is determined after contact with the test compound. If a comparison of the activity of the conjugated polypeptide before and after contact with the test compound shows a difference, namely that the activity decreases upon contact with the test compound, then the test compound is identified as an inhibitor of EGFR activation.

In one embodiment, the invention provides a test compound which comprises a polypeptide of about 75 or fewer amino acid residues in length. In a further embodiment, the invention provides a test compound which is at least about 85% homologous to an amino acid sequence selected from SEQ ID NOs: 1-9. In a still further embodiment, the invention provides a test compound which is at least about 90% homologous to SEQ ID NOs: 1-9. In a still further embodiment, the invention provides a test compound which is at least about 95% homologous to SEQ ID NO: 1-9s. In a still further embodiment, the invention provides a test compound which is at least about 98% homologous to SEQ ID NOs: 1-9. In a still further embodiment, the invention provides a test compound which is at least about 99% homologous to SEQ ID NOs: 1-9. In a still further embodiment, the invention provides a test compound which is at least about 100% homologous to SEQ ID NOs: 1-9.

An assay that measures the functional property of a molecule, such as the catalytic activity of a protein, is a functional assay. In one aspect, the invention provides a functional assay in which mutant EGFR kinase domain molecules are expressed in host cells and then purified from those host cells. These mutant EGFR kinase domain molecules are then localized to surfaces of vesicles, which are, in an exemplary embodiment, lipid vesicles. The catalytic activity of the EGFR kinase molecules can then measured in such a vesicle assay system. The catalytic activity of the mutant EGFR kinase domain molecules is compared to the catalytic activity of wildtype EGFR kinase domain molecules in the same vesicle system in order to determine the functional effects of the mutations present in the mutant EGFR kinase domain molecules.

In one embodiment, the invention provides a method for localizing the mutant EGFR kinase domain molecules to the surfaces of lipid vesicles which utilizes a tag molecule, and in a further embodiment, this tag molecule does not interfere with the catalytic activity of the attached mutant or wildtype EGFR kinase domain molecule. In a further embodiment of the invention, the tag molecule is a hexa-histidine tag.

Binding Assays

Binding assays can be used to determine whether there is an interaction between part of a molecule and a test compound, a ligand, another similar molecule, etc. In one aspect, the invention provides a method of screening for compounds which bind to the kinase domain of EGFR. This method involves determining the ability of a potential binding agent to compete with a polypeptide which has an amino acid sequence selected from SEQ ID NOs: 1-9.

In one embodiment, the polypeptide is radioactively or fluorescently labeled and mixed with EGFR kinase domain to form a protein/polypeptide complex. Any compounds can be added into the solution containing the complex, and the release of the labeled polypeptide from the complex can be monitored. Compounds causing the release are then identified as potential inhibitors that are able to bind to the same are on the kinase as the labeled polypeptide. These compounds can then in a further embodiment be assessed using the vesicle assay system of the present invention to distinguish traditional ATP-competitive inhibitors from novel inhibitors with allosteric mechanisms of action. Novel inhibitors will only inhibit the activation of the kinase activity in the vesicle assay, whereas traditional ATP-competitive inhibitors inhibit basal activity in solution as well as in the vesicle assay system.

Those skilled in the art will recognize a wide variety of fluorescent reporter molecules that can be used in the present invention, including, but not limited to, fluorescently labeled biomolecules such as proteins, phospholipids and DNA hybridizing probes. Similarly, fluorescent reagents specifically synthesized with particular chemical properties of binding or association can be used as fluorescent reporter molecules (Barak et al., (1997) *Journal of Biological Chemistry*, Vol. 272: 27497-27500; Southwick et al., (1990) *Cytometry*, Vol. 11: 418-30; Tsien, (1989) *Methods in Cell Biology*, Vol. 29 Taylor and Wang (eds.): 127-156). Fluorescently labeled antibodies are particularly useful reporter molecules due to their high degree of specificity for attaching to a single molecular target in a mixture of molecules as complex as a cell or tissue.

Luminescent probes can be synthesized within the living cell or can be transported into the cell via several non-mechanical modes including diffusion, facilitated or active transport, signal-sequence-mediated transport, and endocytotic or pinocytotic uptake. Mechanical bulk loading methods, which are well known in the art, can also be used to load luminescent probes into living cells (Barber et al., (1996) *Neuroscience Letter*, Vol. 207, pages 17-20; Bright et al., (1996) *Cytometry*, Vol. 24: 226-33). These methods include electroporation and other mechanical methods such as scrape-loading, bead-loading, impact-loading, syringe-loading, hypertonic and hypotonic loading. Additionally, cells can be genetically engineered to express reporter molecules, such as GFP, coupled to a protein of interest (Chalfie et al., U.S. Pat. No. 5,491,084; Cubitt et al., (1995) *Trends in Biochemical Science*, Vol. 20: 448-55).

Those skilled in the art will recognize a wide variety of ways to measure fluorescence. For example, some fluorescent reporter molecules exhibit a change in excitation or emission spectra, some exhibit resonance energy transfer where one fluorescent reporter loses fluorescence, while a second gains in fluorescence, some exhibit a loss (quenching) or appearance of fluorescence, while some report rotational movements (Giuliano et al., (1995) *Annual Review of Biophysics and Biomolecular Structure*, Vol. 24: 405-3434; Giuliano et al., (1995) *Methods in Neuroscience*, Vol. 27: 1-16).

Targeted Drug Discovery

In order to identify compounds which can serve as potential therapeutics for EGFR-activation related diseases, methods of targeted drug discovery utilizing structural information of the protein are provided the present invention.

In one aspect, the invention provides a method in which cells expressing EGFR are contacted with a compound of this invention (or its salt), and these cells are then monitored for any effect that the compound has on them. The effect may be any observable, either to the naked eye or through the use of instrumentation, change or absence of change in a cell phenotype. The change or absence of change in the cell phenotype monitored may be, for example, without limitation, a change or absence of change in the catalytic activity of EGFR in the cells or a change or absence of change in the interaction of the protein with a natural binding partner.

In one aspect, the invention provides a method for identifying compounds which modulate activation of EGFR. In a preferred aspect of the invention, the ability of a compound to modulate activation of EGFR is predicted based on a theoretically predicted interaction between the compound and an X-ray crystal structure of an EGFR kinase domain, or an X-ray crystal structure of an EGFR kinase domain co-crystallized with a control compound. In one embodiment of the invention, the control compound co-crystallized with the EGFR kinase domain has an amino acid sequence selected from SEQ ID NOs: 1-9. In a further embodiment, the invention provides a method whereby a plurality of atomic coordinates is obtained from structural analysis of the co-crystallized molecules.

In another aspect, the invention provides a method of targeted drug discovery in which the structural information is obtained of an EGFR kinase domain co-crystallized with a control molecule, and residues of the EGFR kinase domain which interact with the control molecule are identified. The structural information from the crystal structure along with the residues of interaction between the kinase domain and the control molecule are compared to a database of potential therapeutics. Potential therapeutics are selected from the database using the structural information to narrow the search parameters and identify the therapeutics most likely to interact with the EGFR kinase domain in the same manner as the control molecule.

In one embodiment, the control molecule used in the above method of targeted drug discovery is an isolated polypeptide. In a further embodiment, the isolated polypeptide comprises an amino acid sequence selected from SEQ ID NOs: 1-9.

In another aspect of the invention, a method is provided for identifying effective therapeutics using a vesicle assay system, in which a decrease in EGFR dimer formation identifies an effective therapeutic. In one embodiment of the invention, the inhibition of dimer formation occurs by binding of the therapeutic to a site on the C-terminal lobe of a kinase domain of an EGFR polypeptide, wherein the site is distal to the ATP binding site.

Purification of Expressed Proteins

One aspect of the present invention utilizes proteins and polypeptides corresponding to the EGFR kinase domain or to the Mig-6 protein. These proteins and polypeptides are used in assays, as inhibitors, or as starting material for crystallization in accordance with various aspects of the present invention. These proteins and polypeptides can be expressed in host cells and purified using techniques described herein and known in the art.

In one embodiment, protein and fragments thereof can be isolated and purified from a reaction mixture by means of peptide separation, for example, by extraction, precipitation, electrophoresis and various forms of chromatography. The proteins of this invention can be obtained in varying degrees of purity depending upon the desired use. Purification can be accomplished by use of protein purification techniques or known in the art.

Crystallization Techniques

Crystal structures described herein are derived using standard techniques known in the art. In a preferred embodiment, crystal structures are generated using X-ray crystallography to generate electron density maps. (see Example IV).

Protein for crystals and assays described herein can be produced using expression and purification techniques described herein and known in the art. For example, high level expression of EGFR or Mig-6 can be obtained in suitable expression hosts such as *E. coli*. Yeast and other eukaryotic expression systems can also be used.

Crystals may be grown or formed by any suitable method, including drop vapor diffusion, batch, liquid bridge, and dialysis, and under any suitable conditions. Crystallization by drop vapor diffusion is often preferable. In addition, those of skill in the art will appreciate that crystallization conditions may be varied. Various methods of crystallizing polypeptides are generally known in the art. See, for example, WO 95/35367, WO 97/15588, EP 646 599 A2, GB 2 306 961 A, and WO 97/08300.

In one embodiment of the invention, a DNA construct comprising EGFR residues 672-998 is provided. In an exemplary embodiment, the DNA construct comprising EGFR residues 672-998 also includes an N-terminal 6-His tag, a linker and a cleavage site for Tobacco Etch Virus protease. In a further embodiment, the DNA construct is expressed in Sf9, CHO or *E. coli* cells. The expressed protein is then purified using techniques known in the art.

After purification, the expressed protein can be stored in a crystallization buffer. Suitable crystallization buffers, for example, include: 0.1 M Na Acetate pH 5.3, 0.2 M $CaCl_2$, 30% v/v Ethanol; 0.1 M Na Citrate pH 5.0, 40% v/v Ethanol; 0.1 M Na Citrate pH 8.7, 20% w/v PEG 4000, 20% v/v Isopropanol; and 0.1 M Na Citrate pH 5.4, 20% w/v PEG 4000, 20% v/v Isopropanol. The sample can be incubated at a temperature ranging from about 4 to 20 degrees Celsius until a crystalline precipitate is formed. Seeds from the crystalline precipitate obtained, as whole crystals or as crushed crystal suspensions, are transferred, along with a suitable crystallization promoter, such as hair of rabbit, to a solution of concentrated substrate in a crystallization buffer in order to allow crystals suitable for X-ray data collection to form.

X-Ray Diffraction

Another aspect of the invention relates to the structure of EGFR, particularly the structure of the EGFR kinase domain. The structure of the kinase domain can be determined utilizing a crystal comprising a polypeptide as described above. According to a preferred embodiment of the present invention, the structure of EGFR, and particularly the EGFR kinase domain, is determined using X-ray crystallography. Any suitable X-ray diffraction method for obtaining three-dimensional structural coordinates of a polypeptide may be used.

Methods of Using X-Ray Diffraction Coordinates

The invention also relates to use of the structural coordinates obtained from the above described X-ray diffraction studies of the EGFR kinase domain. The coordinates may be used, with the aid of computer analysis, to determine the structure of the protein, which can include the secondary and tertiary structure. The EGFR kinase domain structural coordinates can also be used to develop, design, and/or screen compounds that associate with EGFR. As used herein, "associate" means that the compound may bind to or interact with EGFR ionically, covalently, by hydrogen bond, van der Waals interaction, salt bridges, steric interaction, hydrophilic interactions and hydrophobic interaction. The term "associate" also encompasses associations with any portion of the EGFR kinase domain. For example, compounds that associate with EGFR may be compounds that act as competitive inhibitors, un-competitive inhibitors, and non-competitive inhibitors. Compounds that associate with EGFR also may be compounds that act as mediators or other regulatory compounds. In a preferred embodiment, compounds designed to associate with EGFR may be used therapeutically as inhibitors of EGFR activity.

The use of X-ray coordinates for structure determination, molecular design and selection and synthesis of compounds that associate with transmembrane proteins such as EGFR is known in the art. Published PCT application WO 95/35367 describes the use of X-ray structure coordinates to design, evaluate, synthesize and use compounds that associate with the active site of an enzyme. UK Patent Application 2306961A describes the use of X-ray coordinates in rational drug design. Published PCT application, WO 97/15588 describes the structural determination of a polypeptide using x-ray diffraction patterns as well as use of the coordinates and three-dimensional structure in finding compounds that associate with the polypeptide of interest.

In one aspect of the invention, the structural coordinates and structure may be compared to, or superimposed over, other similar molecules. Comparison of EGFR and other molecules for which a graphical structure or three-dimensional structural coordinates are available may be accomplished using available software applications, such as the Molecular Similarity application of QUANTA (Molecular Simulations, Inc., Waltham, Mass.).

Compounds that associate with EGFR also may be computationally evaluated and designed by screening and selecting chemical entities or fragments for their ability to associate with EGFR, and in a preferred embodiment, the EGFR kinase domain. Several methods may be used to accomplish this aspect of the invention. In one embodiment, one may visually inspect a computer-generated model of EGFR, and specifically the kinase domain, based on structural coordinates obtained as described herein. Computer generated models of chemical entities or specific chemical moieties can then be positioned in or around the catalytic domain and evaluated based on energy minimization and molecular dynamics, using, for example, available programs such as CHARMM or AMBER. Positioning of the chemical entity or fragment can be accomplished, for example with docking software such as Quanta and Sybyl. Additionally, known and commercially available computer programs may be used in selecting chemical entities or fragments. Once suitable chemical entities or fragments are selected, they may be assembled into a single compound, such as an inhibitor, mediator, or other regulatory compound. Known and commercially available model building software may assist in assembly.

In one aspect of the invention, compounds that associate with EGFR and specifically the EGFR kinase domain may be designed as a whole, rather than by assembly of specific chemical moieties or chemical entities. This embodiment may be carried out using computer programs such as LUDI (Biosym Technologies, San Diego, Calif.), LEGEND (Molecular Simulations, Burlington, Mass.), and Leap Frog (Tripos Associates, St. Louis, Mo.).

In an exemplary embodiment, a candidate compound is chosen based upon the desired sites of interaction with EGFR and the candidate compound in light of the sites of interaction identified previously from a study of EGFR kinase domain co-crystallized with a control compound. Once the specific interactions are determined, docking studies, using commercially available docking software, are performed to provide preliminary "modeled" complexes of selected candidate compound with EGFR.

Constrained conformational analysis can be performed using, for example, molecular dynamics (MD) to check the integrity of the modeled EGFR-inhibitor complex. Once the complex reaches its most favorable conformational state, the structure as proposed by the MD study is analyzed visually to ensure that the modeled complex complies with known experimental SAR/QSAR (structure-activity relationship/quantitative structure-activity relationship) based on measured binding affinities.

Other modeling techniques may also be used in accordance with the invention. Examples of these techniques are disclosed in Cohen et al., ((1990) *Molecular Modeling Software and Methods of Medicinal Chemistry: Journal of Medical Chemistry*, Vol. 33: 883-94) and Navia et al., ((1992) *The Use of Structural Information in Drug Design: Current Opinions in Structural Biology*, Vol. 2: 202-10), herein incorporated by reference in the entirety.

Kits

This invention also contemplates use of EGFR proteins, fragments thereof, peptides, and their fusion products in a variety of diagnostic kits and methods for detecting the presence of EGFR. Typically the kit will have a compartment containing either a defined EGFR peptide or gene segment or a reagent which recognizes one or the other, e.g., inhibitor fragments or antibodies.

A kit for determining the binding affinity of a test compound to EGFR or a particular domain of EGFR (such as the kinase domain) will typically comprise a test compound, a labeled compound, e.g., a receptor or antibody having known binding affinity for EGFR, a source of EGFR (naturally occurring or recombinant), and a means for separating bound from free labeled compound, such as a solid phase for immobilizing EGFR. Once compounds are screened, those having suitable binding affinity to the EGFR can be evaluated using assays known in the art, to determine whether they act as agonists or antagonists to the receptor.

One embodiment of the invention provides a kit for determining the concentration of EGFR protein in a sample. Such a kit typically comprises a labeled compound, e.g., ligand, inhibitor or antibody, having known binding affinity for EGFR, a source of EGFR (naturally occurring or recombinant), and a means for separating the bound from free labeled compound, for example, a solid phase for immobilizing the EGFR. Reagents and instructions will also normally be provided.

Antibodies, including antigen binding fragments, specific for the EGFR or ligand fragments are useful in diagnostic applications to detect the presence of elevated levels of EGFR and/or its fragments. Such antibodies may allow diagnosis of the amounts of differently processed forms of the EGFR. Such diagnostic assays can employ lysates, live cells, fixed cells, immunofluorescence, cell cultures, body fluids, and further can involve the detection of antigens related to the ligand in serum, or the like. Various commercial assays exist, such as radioimmunoassay (RIA), enzyme-linked immunosorbentassay (ELISA), enzyme immunoassay (EIA), enzyme-multiplied immunoassay technique (EMIT), substrate-labeled fluorescent immunoassay (SLFIA), etc. For example, unlabeled antibodies can be employed by using a second antibody which is labeled and which recognizes the antibody to an EGFR protein or to a particular fragment thereof. Similar assays have also been extensively discussed in the literature. See, e.g., Harlow and Lane ((1988) *Antibodies: A Laboratory Manual*, CSH Press, NY; Chan (ed.)).

Anti-idiotypic antibodies may have a similar use in detecting the presence of antibodies against an EGFR, as such may be diagnostic of various abnormal states. For example, overproduction of EGFR may result in production of various immunological or other medical reactions which may be diagnostic of abnormal physiological states, e.g., in cell growth, activation, or differentiation. Anti-idiotypic antibodies can be used to detect such abnormal physiological states that are a downstream effect of EGFR overexpression.

Frequently, the reagents for diagnostic assays are supplied in kits, so as to optimize the sensitivity of the assay. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. The reagents may be provided as a dry lyophilized powder; such reagents may be reconstituted in an aqueous medium, thus providing appropriate concentrations of reagents for performing the assay.

Many of the aforementioned constituents of the drug screening and the diagnostic assays may be used without modification, or may be modified in a variety of ways. For example, labeling may be achieved by covalently or non-covalently joining a moiety which directly or indirectly provides a detectable signal. In any of these assays, the protein, test compound, EGFR, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free ligand, or alternatively the bound from the free test compound. The EGFR can be immobilized on various matrices followed by washing. Suitable matrices include plastic such as an ELISA plate, filters, and beads. Methods of immobilizing the EGFR to a matrix include, without limitation, direct adhesion to plastic, use of a capture antibody, chemical coupling, and biotin-avidin. The last step in this approach involves the precipitation of ligand/receptor or ligand/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. ((1984) *Clinical Chemistry*, Vol. 30(9): 1457-61), and the double antibody magnetic particle separation as described in U.S. Pat. No. 4,659,678.

SUMMARY OF PREFERRED EMBODIMENTS

In a preferred aspect, the invention provides an isolated polypeptide that interacts with an EGFR peptide and allosterically inhibits activation of said EGFR polypeptide. In one embodiment, the isolated polypeptide allosterically inhibits EGFR activation by preventing formation of an asymmetric dimer interface between EGFR molecules. In such an embodiment, the asymmetric dimer interface is an interface between kinase domains of the EGFR molecules.

In a preferred embodiment and in accordance with the above, the isolated polypeptide comprises an amino acid sequence selected from SEQ ID NOs: 1-9.

In another embodiment in accordance with the above, the isolated polypeptide is at least about 95% homologous to a sequence which is selected from SEQ ID NOs: 1-9.

In one aspect, the invention provides a method for inhibiting EGFR activation. This method includes the step of contacting an EGFR kinase domain with a test molecule that interacts with said EGFR kinase domain. This contacting between the EGFR kinase domain and the test molecule can prevent formation of an asymmetric dimer interface between the EGFR molecule and a kinase domain of a second EGFR molecule. In a preferred embodiment, the test molecule includes an isolated polypeptide with an amino acid sequence selected from: SEQ ID NOs: 1-9.

In one embodiment in accordance with any of the above, the asymmetric dimer interface occurs at a site distal to an ATP binding site of an EGFR molecule.

In another aspect, the invention provides a method for screening for potential inhibitors of EGFR activation. This method includes the steps of: (a) attaching an isolated polypeptide corresponding to an EGFR kinase domain to a lipid vesicle surface to form a conjugated polypeptide; (b) determining activity of the conjugated polypeptide; and (c) contacting the conjugated polypeptide with a test compound; (d) comparing the activity of step (b) with the activity of (c). In a preferred embodiment, following step (c), the invention provides a step in which the activity of the conjugated polypeptide is determined In a still further preferred embodiment, if the activity determined in (c) is less than the activity determined in (b), the comparing step in (d) identifies the test compound as an inhibitor of EGFR activation.

In yet another aspect, the invention provides a method of identifying an effective therapeutic. This method includes using a vesicle assay system, and in a preferred embodiment, a decrease in EGFR dimer formation identifies an effective therapeutic.

In accordance with any of the above, in one embodiment of the invention, the decrease in dimer formation occurs by binding of the therapeutic to a site on the C-terminal lobe of a kinase domain of an EGFR polypeptide, where that site is distal to the ATP binding site.

In accordance with any of the above, in one embodiment of the invention, the therapeutic includes an isolated polypeptide having an amino acid sequence selected from SEQ ID NOs: 1-9.

In one aspect, the invention provides a method of screening for compounds which bind to kinase domain of EGFR, and this method includes a step of determining whether a potential binding agent can compete with a polypeptide comprising an amino acid sequence selected from SEQ ID NOs: 1-9.

In another aspect, the invention provides a method of targeted drug discovery which includes the following steps: (a) determining structural information of an EGFR kinase domain co-crystallized with a control molecule; (b) identifying residues of the EGFR kinase domain which interact with said the molecule; (c) comparing information from (a) and (b) to a database of potential therapeutics; and (d) selecting potential therapeutics from the database that are most likely to interact with the EGFR kinase domain in a manner similar to the control molecule. In a preferred embodiment, the information from (a) and (b) is used to narrow search parameters based on amino acid sequence and predicted structure.

In accordance with any of the above, in one embodiment, the control molecule is an isolated polypeptide.

In accordance with any of the above, in a further embodiment, the isolated polypeptide comprises an amino acid sequence selected from SEQ ID NOs: 1-9.

In one aspect, the invention provides a pharmaceutical composition which includes one or more isolated polypeptides with amino acid sequence selected from SEQ ID NOs: 1-9. In a preferred aspect, the one or more polypeptides are combined with at least one pharmaceutically acceptable carrier.

In accordance with the composition above, in one embodiment of the invention, the one or more isolated polypeptides bind to a kinase domain of an EGFR molecule.

In accordance with any of the above compositions, the one or more isolated polypeptides prevent formation of an asymmetric dimer interface between EGFR molecules.

In accordance with any of the above compositions, in a preferred embodiment the composition is a treatment for cancer.

In another aspect, the invention provides a vesicle assay system that includes a polypeptide conjugated to a lipid vesicle surface, where that polypeptide includes an EGFR kinase domain; and a means of detecting if the polypeptide forms dimers in the presence of a test compound. In a preferred aspect, an inhibition of dimer formation identifies said polypeptide as an inhibitor of EGFR kinase activity.

In accordance with the system above, in one embodiment of the invention, the inhibition of dimer formation occurs by binding of the polypeptide to a site on an EGFR molecule, where that site is located distal to the ATP binding site in the C-terminal lobe of the kinase domain of said EGFR molecule.

In accordance with any of the systems above, in a preferred embodiment of the invention, the polypeptide comprises an isolated polypeptide having amino acid sequence selected from SEQ ID NOs: 1-9.

In one aspect, the invention provides a functional assay which includes the following steps: (a) expressing and purifying mutant EGFR kinase domain molecules; (b) localizing the mutant EGFR kinase domain molecules to surfaces of lipid vesicles; and (c) measuring the catalytic activity of the EGFR kinase molecules. In a preferred aspect, the catalytic activity measured in (c) can be compared to the catalytic activity of wildtype EGFR kinase domain molecules in order to determine functional effects of mutations present in the mutant EGFR kinase domain molecules.

In accordance with the assay above, in one embodiment of the invention, localizing the mutant EGFR kinase domain molecules is accomplished using a tag molecule which does not interfere with catalytic activity of said mutant EGFR kinase domain molecules.

In accordance with any of the functional assays above, in one embodiment of the invention the tag molecule is a hexahistidine tag.

The present invention may be better understood by reference to the following non-limiting Examples, which are provided as exemplary of the invention. The following examples are presented in order to more fully illustrate preferred embodiments of the invention, but should in no way be construed as limiting the broad scope of the invention.

EXAMPLES

Example I

Expression and Purification of the Kinase Domain

DNA encoding residues 672-998 of human EGFR was cloned into pFAST BAC HT (Invitrogen) using the NcoI and HindIII restriction sites (FIG. 2). The construct contains an N-terminal 6-His tag, a linker, and a cleavage site for the Tobacco Etch Virus protease (TEV). (MSYHHHHHHDY-DIPTTENLYFQGAM) SEQ ID NO: 12. All mutations were introduced using the Quik-change site-directed mutagenesis kit (Stratagene). Sequences of all plasmids were confirmed by DNA sequencing.

Recombinant bacmid (Bac-to-Bac expression system, Gibco BRL) were transfected into SD cells grown in suspension. Cells were harvested 2-3 days after infection by centrifugation at 4000×g and resuspended in a buffer containing 50 mM Tris, 5% glycerol, 1 mM DTT, and protease inhibitor cocktail (Roche), pH 8.0.

Cells were homogenized by French press in resuspension buffer and the lysate was centrifuged at 40000×g for 45 minutes. The supernatant was then loaded onto a 60 ml Q-Sepharose Fastflow column (Amersham) equilibrated in buffer A (50 mM Tris, 5% glycerol, and 15 mM β-mercaptolethanol, pH 8.0). Proteins were eluted using buffer A plus 1 M NaCl. The eluted protein was loaded onto a 1 ml Histrap column (Amersham) pre-equilibrated with buffer B (20 mM Tris, 500 mM NaCl, 5% glycerol, 20 mM imidazole, pH 8.0) and eluted using a gradient of imidazole (20-250 mM) after extensive wash with buffer B. The eluted proteins were either purified immediately using a 6 ml Uno-Q column (Bio-rad) to produce His-tagged kinase domains, or treated with the TEV protease overnight at 4° C. to remove the N-terminal His-tag before being subjected to Uno-Q purification for crystallization (see Example IV), analytical ultracentrifugation (see Example VI), and static light scattering (see Example VII).

Proteins were diluted 10-fold using buffer C (20 mM Tris, 20 mM NaCl, 5% Glycerol, and 2 mM DTT, pH 8.0) and loaded onto the Uno-Q column pre-equilibrated with buffer C. Proteins were eluted using a gradient of NaCl (20-500 mM). Fractions containing the EGFR protein were pooled, concentrated, and buffer exchanged into 20 mM Tris, 50 mM NaCl, 2 mM TCEP, pH 8.0. Proteins were concentrated to 10-30 mg/ml and flash-frozen in liquid nitrogen and stored at −80° C. Mass spectrometric analysis was used to confirm the identity of the proteins.

Example II

Preparation of Small Unilamellar Vesicles

DOPC and DOGS-NTA-Ni lipids in chloroform (Avanti Polar Lipids, Inc) were mixed in a glass tube. A lipid film was formed upon removing chloroform under a stream of argon gas, followed by putting the tube under vacuum for at least 3 hours.

Rehydration buffer (10 mM $MgCl_2$, 20 mM Tris, pH 7.5) was added to the lipid film and incubated for at least three hours. Intermittent vigorous vortexing during the incubation was applied to convert the lipid film into large, multilamellar vesicles.

The multilamellar vesicles were then forced through a polycarbonate filter (pore size: 100 nm) 21-41 times using a mini extruder (Avanti Polar Lipids, Inc) to yield homogenous small unilamellar vesicles.

Figure 16:
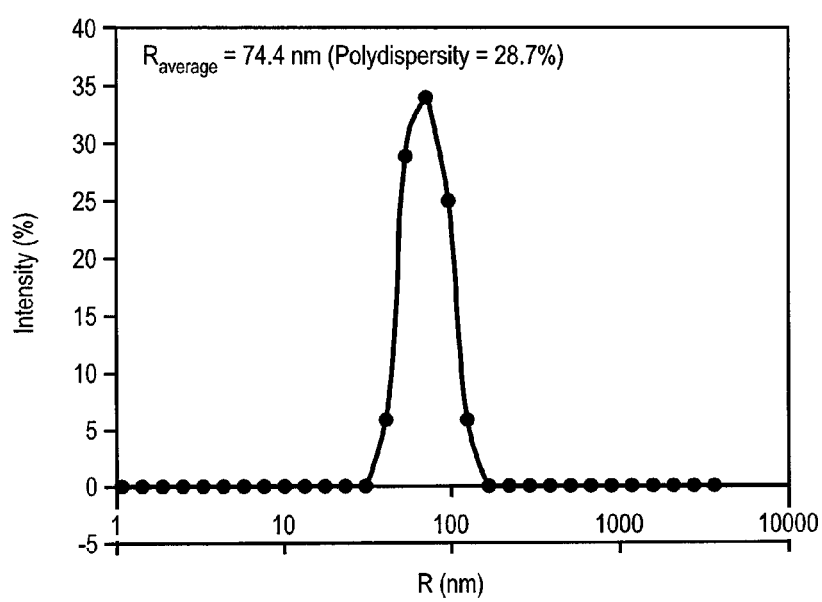
FIG. 16 shows a representative size distribution of lipid vesicles measured by dynamic light scattering.

The diameter of the vesicles was measured by static light scatting to be in a range from 100-200 nm (FIG. 16).

Example III

Kinase Assay in Solution and with Vesicles

A continuous enzyme-coupled kinase assay was performed to measure the kinase activity of the proteins as described in Barker et al., ((1995) *Biochemistry*, Vol. 34(54): 14843-51), with modifications, as described herein. The ATP concentration was kept to 0.5 mM.

The buffer used contained 10 mM $MgCl_2$, 20 mM Tris, and pH 7.5. Replacement of $MgCl_2$ by $MnCl_2$ in the assays resulted in a substantial increase of the catalytic activity of the kinase domain, as noted previously (Mohammadi et al., (1993) *Biochemistry* (34):8742-8.; Wedergaertner and Gill, (1989) *Journal of Biological Chemistry* 264(19):11346-53). The substrate peptide was derived from the region spanning Y1173 in EGFR (TAENAEYLRVAPQ) (SEQ ID NO: 7). All proteins used in this assay contained the N-terminal $(His)_6$ tag unless otherwise noted.

The protein concentrations of the EGFR kinase domain used in the assay ranged from 3.5 to 14 µM. The total concentration of the DOGS-NTA-Ni in the bulk solution was kept to 12.5 µM in all assays with DOG-NTA-Ni-containing vesicles. For assays of the kinase domain attached to vesicles, the protein and vesicles were preincubated at 4° C. for ~5 min.

The wildtype EGFR kinase domain was mixed with vesicles containing 0, 0.5, 1, 2 and 5 mole percent of DOGS-NTA-Ni prior to the start of the assay. The final concentration of the protein in the assay was 3.5 µM. The substrate peptide concentration used in these assays was 1 mM. A sample of the kinase domain in the absence of lipid vesicles was also assayed using the same setup as a control. (FIG. 6B).

For comparing the specific activity of the wildtype and various mutant forms of the EGFR kinase domain in the presence and absence of lipid vesicles, the density of DOGS-NTA-Ni on lipid vesicles was kept at 5 mole percent. Preliminary experiments using the substrate peptide at various concentrations showed that the value of KM for the wildtype kinase domain and this substrate peptide was greater than 4 mM. Due to this high value of $K_M$, the values of $K_M$ and $k_{cat}$ were not measured directly. Instead, the value of $k_{cat}/K_M$ was derived from a linear fit to the data obtained, using concentrations of the peptide that are much lower than the estimated value of $K_M$ ($V=[S]V_{max}/(K_M+[S])$, $V \sim (V_{max}/K_M)[S]$ when $[S]<<K_M$, $k_{cat}=V_{max}$/amount of the enzyme, where V and $V_{max}$ are the initial velocity and maximum initial velocity, respectively. (FIG. 6A).

Example IV

Crystallization and Structure Determination

Two ATP analog conjugates were synthesized as described (Parang et al., 2001). The peptide sequences were AEEE-IYGEFEAKK (SEQ ID NO: 9) (the Src substrate peptide, Levinson et al., 2006) and ENAEYLRVAPQK (SEQ ID NO: 8) (from a region that spans Tyr1173 in EGFR). The wildtype kinase domain with the His-tag removed (containing an N-terminal tri-peptide with sequence "GAM" from the vector and residues 682-998 from EGFR) at 6 mg/ml was co-crystallized with each of the synthesized peptides.

Diffraction data were collected at −170° C. at Beamlines 8.2.2, 8.3.1, and 12.3.1 at the ALS and processed using HKL2000 suite. The high $R_{sym}$ values of the data for the active structures at the highest resolution shell are partially due to the high redundancy of the data. The data are included for refinement since they contain valid information as judged by the I/σ values and the quality of electron densities. The data for the inactive structure may be compromised by multiple lattices and high mosaicity in the diffraction pattern, which underlies the high free R value of the final model of the inactive structure.

Figure 7:
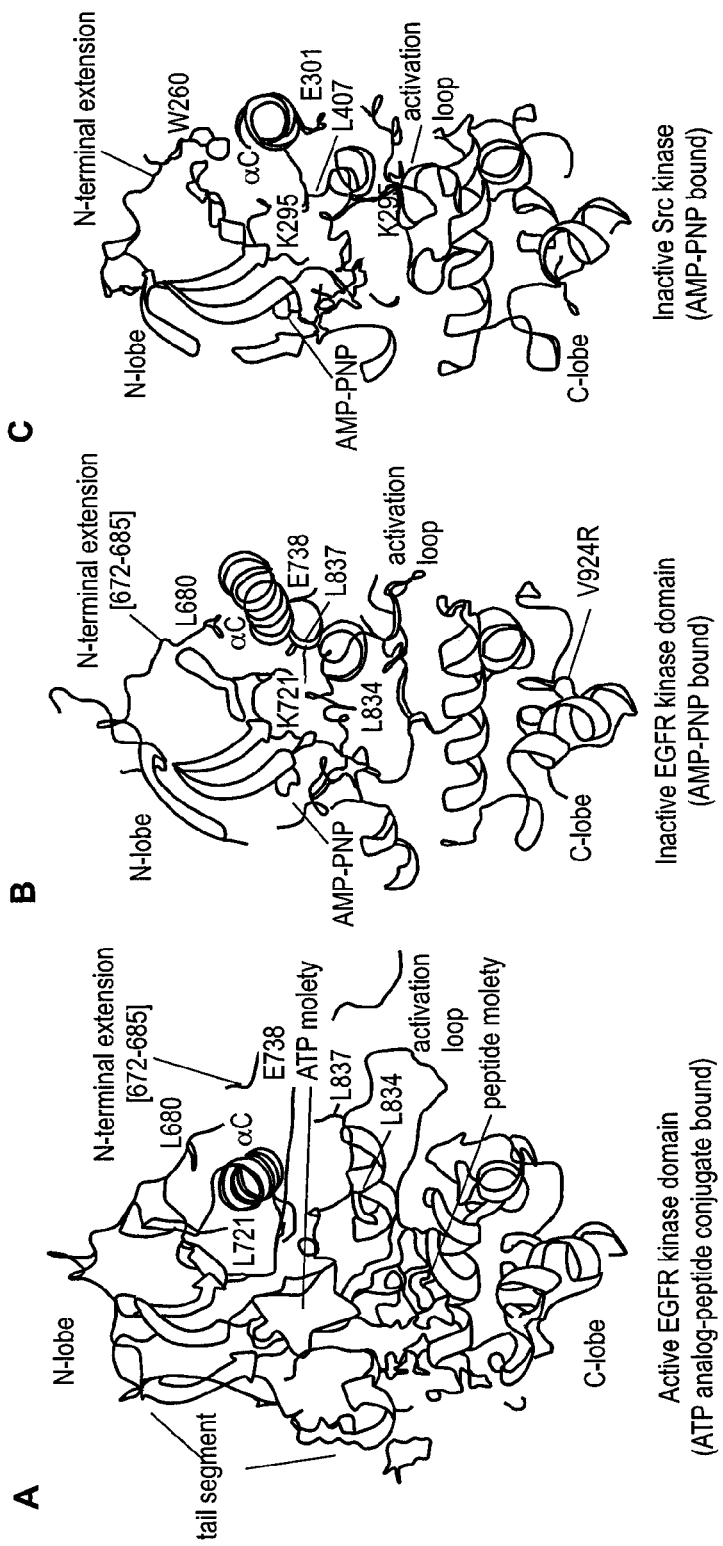
FIG. 7 shows the crystal structure of an EGFR kinase domain in complex with an ATP analog substrate peptide conjugate (A) and in complex with AMP-PNP (B).

The original structures of active (PDB ID: 1M14) (Stamos et al., (2002) *The Journal of Biological Chemistry*, Vol. 277 (48): 46265-72) and inactive (PDB ID: 1XKK) EGFR kinase domain was used as the starting model for solving the active and inactive structures. The structures were refined by iterative structural refinement using the program CNS and manual model building using the program O. (Brunger et al. (1998) Acta Crystallographica, Section D Biological Crystallography, Vol. 54(Pt. 5): page 905-21). The ATP analog-peptide conjugate and the AMP-PNP molecules were built after the free R-value dropped below 32%. (See FIG. 7).

Example V

Cell-Based Signaling Analysis

The EGFR full-length gene with a fragment encoding an N-terminal FLAG antibody recognition sequence (DYKD-DDDK) SEQ ID NO: 13 inserted between the 24-residue signal peptide and the mature protein was amplified by PCR and cloned into the pcDNA3.1 vector (BD Biosciences) using XhoI and XbaI restriction enzymes.

Mutations were generated by using the Quickchange site-directed mutagenesis kit. All plasmids used for transfection were prepared using the HiSpeed Plasmid Midi kit (Qiagen) and the sequences were confirmed by DNA sequencing prior to use.

NIH3T3 cells (which express low levels of endogenous EGFR that are undetectable by Western blot; Bishayee et al., 1999) were cultured in Dulbecco's modified Eagle's medium supplemented with 10% fetal bovine serum, streptomycin/penicillin, sodium pyruvate, and nonessential amino acids (all from Gibco) at 37° C. with 5% $CO_2$.

Cells were plated and cultured overnight in 6-well plates in the same medium without antibiotics for transfection. Cells were transfected using Fugene 6 (Roche) according to the manufacturer's instructions with a DNA:Fugene 6 ratio of 1.5 μg:4.5 μl when cells reacted ~50% confluency.

Cells were cultured for ~36 hours after transfection and serum-starved for ~12 hours before ligand stimulation and harvesting. Ligand stimulation of cells was performed using 50 ng/ml EGF (PeproTech, Inc.) at 37° C. for 5 minutes. Cells were lysed in a buffer containing 50 mM Tris, 150 mM NaCl, 1 mM EDTA, 1 mM $Na_3VO_4$, 1 mM NaF, 1% Triton X-100, and a protease inhibitor cocktail (Roche), pH 7.5.

The lysates were centrifuged at 14,000×g for 10 minutes to remove insoluble material. The supernatants were collected and the protein concentrations were determined using the Bradford protein assay (Bio-Rad) for normalizing the total amount of proteins loaded onto the gels. Samples were run on SDS gels and subjected to Western blot analysis. The total amount of EGFR was monitored using an anti-FLAG antibody (Sigma). The levels of phosphorylation of EGFR at three sites were monitored using anti-EGFR antibodies specific for phosphorylation at Tyr1045 (Cell Signaling), Tyr1068 (Cell Signaling), and Tyr1173 (Santa Cruz). (FIG. 9B and FIG. 19).

Example VI

Analytical Ultracentrifugation

Sedimentation equilibrium experiments were performed using wildtype EGFR kinase domain protein (with the N-terminal His-tag removed) in 100 mM NaCl, 1 mM TCEP, 10 mM Tris, pH 8.0 at protein concentrations of 13.3 μM, 26.6 μM, and 53 μM in a Beckman XL-I ultracentrifuge using an AN-60 Ti rotor at 20° C., 20000 rpm.

Scans at 280 nm and 300 nm were taken every three hours and equilibrium was assumed to have been reached if two consecutive scans were identical. Data were collected at both wavelengths in a radial step mode with 0.001 cm step-size and 20-point averages. Data analysis and Monte Carlo analysis were performed using the software Ultrascan. The partial specific volume and buffer density of the protein were calculated to be 0.74 ml/g and 1.003 g/ml respectively using the same software.

Five of the six data sets taken at the three protein concentration and two wavelengths were fitted globally to multiple models. The data set taken at 300 nm for the sample at 13.3 μM was excluded from the fitting because the signals were too weak to be fit reliably. A one-species ideal model with a molecular weight of 37890 Da was found to be most appropriate, very close to the molecular weight calculated from the protein sequence (37516 Da). Consequent Monte Carlo analysis suggested that the molecular weight was within the range of 37476-38296 Da with 99% confidence. (FIG. 15A).

Example VII

Multi-Angle Static Light Scattering

The wildtype EGFR kinase domain with the N-terminal His-tag removed at 1-2 mg/ml (27-53 μM) concentration was loaded on to a KW-803 size exclusion column pre-equilibrated in 10 mM $NaHPO_4$—$NaH_2PO_4$, 100 mM NaCl, pH 7.5 at a flow rate of 0.4 ml/min The protein eluted from the chromatography system was detected by a coupled 18-angle light scattering detector and refractive index detector with a data collection interval of 0.5 seconds. Data analysis was performed using the program ASTRA, which yielded a molecular weight for the EGFR kinase domain of 39500 Da. (FIG. 15B).

Example VIII

Western Blot

The levels of phosphorylation of EGFR at three sites were monitored using anti-EGFR antibodies specific for phosphorylation at Tyr1045 (Cell Signaling), Tyr1068 (Cell Signaling) and Tyr1173 (Santa Cruz). The total amount of EGFR in the samples was monitored using an anti-FLAG antibody (Sigma). All Western blots, except those from (FIG. 19), were performed as follows: Anti-EGFR (phospho-Tyr1068) and the FLAG epitope were analyzed separately by transferring protein bands from 8% SDS gels to PVDF membranes. Subsequently, the membranes were stripped in a buffer containing 2% SDS, 100 mM β-mercaptoethanol, 50 mM Tris, pH 6.8. (See FIG. 9, FIG. 10, and FIG. 12). The membranes used for the phospho-Tyr1068 Western blot was reblotted with anti-EGFR (phospho-Tyr1045), and that originally used for the anti-FLAG blot was reblotted with anti-EGFR (phospho-Tyr1173). Western blots shown in (FIG. 19) were done using four separate gels.

What is claimed is:

1. An isolated polypeptide which is at least about 95% homologous to a sequence which is selected from SEQ ID NOs: 1-5.

2. A pharmaceutical composition comprising one or more isolated polypeptides with amino acid sequence selected from SEQ ID NOs: 1-5, wherein said one or more polypeptides are combined with at least one pharmaceutically acceptable carrier.

* * * * *

```
                         SEQUENCE LISTING

<160> NUMBER OF SEQ ID NOS: 21

<210> SEQ ID NO 1
<211> LENGTH: 55
<212> TYPE: PRT
<213> ORGANISM: Homo sapiens

<400> SEQUENCE: 1

Glu Asp Arg Pro Pro Lys Val Pro Pro Arg Glu Pro Leu Ser Pro Ser
1               5                   10                  15

Asn Ser Arg Thr Pro Ser Pro Lys Ser Leu Pro Ser Tyr Leu Asn Gly
            20                  25                  30

Val Met Pro Pro Thr Gln Ser Phe Ala Pro Asp Pro Lys Tyr Val Ser
        35                  40                  45

Ser Lys Ala Leu Gln Arg Gln
    50                  55

<210> SEQ ID NO 2
<211> LENGTH: 26
<212> TYPE: PRT
<213> ORGANISM: Homo sapiens

<400> SEQUENCE: 2

Lys Ser Leu Pro Ser Tyr Leu Asn Gly Val Met Pro Pro Thr Gln Ser
1               5                   10                  15

Phe Ala Pro Asp Pro Lys Tyr Val Ser Ser
            20                  25

<210> SEQ ID NO 3
<211> LENGTH: 26
<212> TYPE: PRT
<213> ORGANISM: Homo sapiens

<400> SEQUENCE: 3

Lys Ser Leu Pro Ser Tyr Leu Asn Gly Val Met Pro Pro Thr Gln Ser
1               5                   10                  15

Phe Ala Pro Asp Pro Lys Tyr Val Ser Ser
            20                  25

<210> SEQ ID NO 4
<211> LENGTH: 25
<212> TYPE: PRT
<213> ORGANISM: Homo sapiens

<400> SEQUENCE: 4

Ser Tyr Leu Asn Gly Val Met Pro Pro Thr Gln Ser Phe Ala Pro Asp
1               5                   10                  15

Pro Lys Tyr Val Ser Ser Lys Ala Leu
            20                  25
```

<210> SEQ ID NO 5
<211> LENGTH: 16
<212> TYPE: PRT
<213> ORGANISM: Homo sapiens

<400> SEQUENCE: 5

Met Pro Pro Thr Gln Ser Phe Ala Pro Asp Pro Lys Tyr Val Ser Ser
1               5                   10                  15

<210> SEQ ID NO 6
<211> LENGTH: 327
<212> TYPE: PRT
<213> ORGANISM: Homo sapiens

<400> SEQUENCE: 6

Gly Glu Ala Pro Asn Gln Ala Leu Leu Arg Ile Leu Lys Glu Thr Glu
1               5                   10                  15

Phe Lys Lys Ile Lys Val Leu Gly Ser Gly Ala Phe Gly Thr Val Tyr
                20                  25                  30

Lys Gly Leu Trp Ile Pro Glu Gly Glu Lys Val Lys Ile Pro Val Ala
            35                  40                  45

Ile Lys Glu Leu Arg Glu Ala Thr Ser Pro Lys Ala Asn Lys Glu Ile
        50                  55                  60

Leu Asp Glu Ala Tyr Val Met Ala Ser Val Asp Asn Pro His Val Cys
65                  70                  75                  80

Arg Leu Leu Gly Ile Cys Leu Thr Ser Thr Val Gln Leu Ile Thr Gln
                85                  90                  95

Leu Met Pro Phe Gly Cys Leu Leu Asp Tyr Val Arg Glu His Lys Asp
                100                 105                 110

Asn Ile Gly Ser Gln Tyr Leu Leu Asn Trp Cys Val Gln Ile Ala Lys
            115                 120                 125

Gly Met Asn Tyr Leu Glu Asp Arg Arg Leu Val His Arg Asp Leu Ala
        130                 135                 140

Ala Arg Asn Val Leu Val Lys Thr Pro Gln His Val Lys Ile Thr Asp
145                 150                 155                 160

Phe Gly Leu Ala Lys Leu Leu Gly Ala Glu Glu Lys Glu Tyr His Ala
                165                 170                 175

Glu Gly Gly Lys Val Pro Ile Lys Trp Met Ala Leu Glu Ser Ile Leu
                180                 185                 190

His Arg Ile Tyr Thr His Gln Ser Asp Val Trp Ser Tyr Gly Val Thr
            195                 200                 205

Val Trp Glu Leu Met Thr Phe Gly Ser Lys Pro Tyr Asp Gly Ile Pro
210                 215                 220

Ala Ser Glu Ile Ser Ser Ile Leu Glu Lys Gly Glu Arg Leu Pro Gln
225                 230                 235                 240

Pro Pro Ile Cys Thr Ile Asp Val Tyr Met Ile Met Val Lys Cys Trp
                245                 250                 255

Met Ile Asp Ala Asp Ser Arg Pro Lys Phe Arg Glu Leu Ile Ile Glu
            260                 265                 270

Phe Ser Lys Met Ala Arg Asp Pro Gln Arg Tyr Leu Val Ile Gln Gly
        275                 280                 285

Asp Glu Arg Met His Leu Pro Ser Pro Thr Asp Ser Asn Phe Tyr Arg
290                 295                 300

Ala Leu Met Asp Glu Glu Asp Met Asp Val Val Asp Ala Asp Glu
305                 310                 315                 320

Tyr Leu Ile Pro Gln Gln Gly

<210> SEQ ID NO 7
<211> LENGTH: 13
<212> TYPE: PRT
<213> ORGANISM: Homo sapiens

<400> SEQUENCE: 7

Thr Ala Glu Asn Ala Glu Tyr Leu Arg Val Ala Pro Gln
1               5                   10

<210> SEQ ID NO 8
<211> LENGTH: 12
<212> TYPE: PRT
<213> ORGANISM: Homo sapiens

<400> SEQUENCE: 8

Glu Asn Ala Glu Tyr Leu Arg Val Ala Pro Gln Lys
1               5                   10

<210> SEQ ID NO 9
<211> LENGTH: 13
<212> TYPE: PRT
<213> ORGANISM: Homo sapiens

<400> SEQUENCE: 9

Ala Glu Glu Glu Ile Tyr Gly Glu Phe Glu Ala Lys Lys
1               5                   10

<210> SEQ ID NO 10
<211> LENGTH: 5751
<212> TYPE: DNA
<213> ORGANISM: Homo sapiens

<400> SEQUENCE: 10

| | |
|---|---:|
| gacgcgccct gtagcggcgc attaagcgcg gcgggtgtgg tggttacgcg cagcgtgacc | 60 |
| gctacacttg ccagcgccct agcgcccgct cctttcgctt tcttcccttc ctttctcgcc | 120 |
| acgttcgccg gctttccccg tcaagctcta atcggggggc tccctttagg gttccgattt | 180 |
| agtgctttac ggcacctcga ccccaaaaaa cttgattagg gtgatggttc acgtagtggg | 240 |
| ccatcgccct gatagacggt ttttcgccct ttgacgttgg agtccacgtt ctttaatagt | 300 |
| ggactcttgt tccaaactgg aacaacactc aaccctatct cggtctattc ttttgattta | 360 |
| taagggattt tgccgatttc ggcctattgg ttaaaaaatg agctgattta acaaaaattt | 420 |
| aacgcgaatt ttaacaaaat attaacgttt acaatttcag gtggcacttt tcggggaaat | 480 |
| gtgcgcggaa cccctatttg tttatttttc taaatacatt caaatatgta tccgctcatg | 540 |
| agacaataac cctgataaat gcttcaataa tattgaaaaa ggaagagtat gagtattcaa | 600 |
| catttccgtg tcgcccttat tcccttttt gcggcatttt gccttcctgt ttttgctcac | 660 |
| ccagaaacgc tggtgaaagt aaaagatgct gaagatcagt tgggtgcacg agtgggttac | 720 |
| atcgaactgg atctcaacag cggtaagatc cttgagagtt ttcgccccga gaacgttttt | 780 |
| ccaatgatga gcacttttaa agttctgcta tgtggcgcgg tattatcccg tattgacgcc | 840 |
| gggcaagagc aactcggtcg ccgcatacac tattctcaga atgacttggt tgagtactca | 900 |
| ccagtcacag aaaagcatct tacgatggc atgacagtaa gagaattatg cagtgctgcc | 960 |
| ataaccatga gtgataacac tgcggccaac ttacttctga caacgatcgg aggaccgaag | 1020 |
| gagctaaccg cttttttgca acatgggga gatcatgtaa ctcgccttga tcgttgggaa | 1080 |
| ccggagctga atgaagccat accaaacgac gagcgtgaca ccacgatgcc tgtagcaatg | 1140 |

```
gcaacaacgt tgcgcaaact attaactggc gaactactta ctctagcttc ccggcaacaa    1200
ttaatagact ggatggaggc ggataaagtt gcaggaccac ttctgcgctc ggcccttccg    1260
gctggctggt ttattgctga taaatctgga gccggtgagc gtgggtctcg cggtatcatt    1320
gcagcactgg ggccagatgg taagccctcc cgtatcgtag ttatctacac gacggggagt    1380
caggcaacta tggatgaacg aaatagacag atcgctgaga taggtgcctc actgattaag    1440
cattggtaac tgtcagacca agtttactca tatatacttt agattgattt aaaacttcat    1500
ttttaattta aaaggatcta ggtgaagatc cttttttgata atctcatgac caaaatccct    1560
taacgtgagt tttcgttcca ctgagcgtca gaccccgtag aaaagatcaa aggatcttct    1620
tgagatcctt ttttttctgcg cgtaatctgc tgcttgcaaa caaaaaaacc accgctacca    1680
gcggtggttt gtttgccgga tcaagagcta ccaactcttt ttccgaaggt aactggcttc    1740
agcagagcgc agataccaaa tactgtcctt ctagtgtagc cgtagttagg ccaccacttc    1800
aagaactctg tagcaccgcc tacatacctc gctctgctaa tcctgttacc agtggctgct    1860
gccagtggcg ataagtcgtg tcttaccggg ttggactcaa gacgatagtt accggataag    1920
gcgcagcggt cgggctgaac ggggggttcg tgcacacagc ccagcttgga gcgaacgacc    1980
tacaccgaac tgagatacct acagcgtgag cattgagaaa gcgccacgct tcccgaaggg    2040
agaaaggcgg acaggtatcc ggtaagcggc agggtcggaa caggagagcg cacgagggag    2100
cttccagggg gaaacgcctg gtatctttat agtcctgtcg ggtttcgcca cctctgactt    2160
gagcgtcgat ttttgtgatg ctcgtcaggg gggcggagcc tatggaaaaa cgccagcaac    2220
gcggcctttt tacggttcct ggccttttgc tggccttttg ctcacatgtt ctttcctgcg    2280 ttatccctg attctgtgga taaccgtatt accgcctttg agtgagctga taccgctcgc    2340
cgcagccgaa cgaccgagcg cagcgagtca gtgagcgagg aagcggaaga gcgcctgatg    2400
cggtattttc tccttacgca tctgtgcggt atttcacacc gcagaccagc cgcgtaacct    2460
ggcaaaatcg gttacggttg agtaataaat ggatgccctg cgtaagcggg tgtgggcgga    2520
caataaagtc ttaaactgaa caaaatagat ctaaactatg acaataaagt cttaaactag    2580
acagaatagt tgtaaactga atcagtccca gttatgctgt gaaaaagcat actggacttt    2640
tgttatggct aaagcaaact cttcattttc tgaagtgcaa attgcccgtc gtattaaaga    2700
ggggcgtggc caagggcatg gtaaagacta tattcgcggc gttgtgacaa tttaccgaac    2760
aactccgcgg ccgggaagcc gatctcggct tgaacgaatt gttaggtggc ggtacttggg    2820
tcgatatcaa agtgcatcac ttcttcccgt atgcccaact ttgtatagag agccactgcg    2880
ggatcgtcac cgtaatctgc ttgcacgtag atcacataag caccaagcgc gttggcctca    2940
tgcttgagga gattgatgag cgcggtggca atgccctgcc tccggtgctc gccggagact    3000
gcgagatcat agatatagat ctcactacgc ggctgctcaa acctgggcag aacgtaagcc    3060
gcgagagcgc caacaaccgc ttcttggtcg aaggcagcaa gcgcgatgaa tgtcttacta    3120
cggagcaagt tcccgaggta atcggagtcc ggctgatgtt gggagtaggt ggctacgtct    3180
ccgaactcac gaccgaaaag atcaagagca gcccgcatgg atttgacttg gtcagggccg    3240
agcctacatg tgcgaatgat gcccatactt gagccaccta actttgtttt agggcgactg    3300
ccctgctgcg taacatcgtt gctgctgcgt aacatcgttg ctgctccata acatcaaaca    3360
tcgacccacg cgctaacgcg cttgctgctt ggatgcccga ggcatagact gtacaaaaaa    3420
acagtcataa caagccatga aaaccgccac tgcgccgtta ccaccgctgc gttcggtcaa    3480
ggttctggac cagttgcgtg agcgcatacg ctacttgcat tacagtttac gaaccgaaca    3540
```

```
ggcttatgtc aactgggttc gtgccttcat ccgtttccac ggtgtgcgtc acccggcaac    3600
cttgggcagc agcgaagtcg aggcatttct gtcctggctg gcgaacgagc gcaaggtttc    3660
ggtctccacg catcgtcagg cattggcggc cttgctgttc ttctacggca aggtgctgtg    3720
cacggatctg ccctggcttc aggagatcgg aagacctcgg ccgtcgcggc gcttgccggt    3780
ggtgctgacc ccggatgaag tggttcgcat cctcggtttt ctggaaggcg agcatcgttt    3840
gttcgcccag gactctagct atagttctag tggttggcta cgtatactcc ggaatattaa    3900
tagatcatgg agataattaa aatgataacc atctcgcaaa taaataagta ttttactgtt    3960
ttcgtaacag ttttgtaata aaaaaaccta taaatattcc ggattattca taccgtccca    4020
ccatcgggcg cggatctcgg tccgaaacca tgtcgtacta ccatcaccat caccatcacg    4080
attacgatat cccaacgacc gaaaacctgt attttcaggg cgccatggga gaagctccca    4140
accaagctct cttgaggatc ttgaaggaaa ctgaattcaa aaagatcaaa gtgctgggct    4200
ccggtgcgtt cggcacggtg tataagggac tctggatccc agaaggtgag aaagttaaaa    4260
ttcccgtcgc tatcaaggaa ttaagagaag caacatctcc gaaagccaac aaggaaatcc    4320
tcgatgaagc ctacgtgatg gccagcgtgg acaacccccca cgtgtgccgc ctgctgggca    4380
tctgcctcac ctccaccgtg caactcatca cgcagctcat gcccttcggc tgcctcctgg    4440
actatgtccg ggaacacaaa gacaatattg ctcccagta cctgctcaac tggtgtgtgc    4500
agatcgcaaa gggcatgaac tacttggagg accgtcgctt ggtgcaccgc gacctggcag    4560
ccaggaacgt actggtgaaa acaccgcagc atgtcaagat cacagatttt gggctggcca    4620
aactgctggg tgcggaagag aaagaatacc atgcagaagg aggcaaagtg cctatcaagt    4680
ggatggcatt ggaatcaatt ttacacagaa tctataccca ccagagtgat gtctggagct    4740
acggggtgac cgtttgggag ttgatgacct ttggatccaa gccatatgac ggaatccctg    4800
ccagcgagat ctcctccatc ctggagaaag gagaacgcct ccctcagcca cccatatgta    4860
ccatcgatgt ctacatgatc atggtcaagt gctggatgat agacgcagat agtcgcccaa    4920
agttccgtga gttgatcatc gaattctcca aaatggcccg agaccccag cgctaccttg    4980 tcattcaggg ggatgaaaga atgcatttgc caagtcctac agactccaac ttctaccgtg    5040
ccctgatgga tgaagaagac atggacgacg tggtggatgc cgacgagtac ctcatcccac    5100
agcagggtta aagcttgtc gagaagtact agaggatcat aatcagccat accacatttg    5160
tagaggtttt acttgcttta aaaaacctcc cacacctccc cctgaacctg aaacataaaa    5220
tgaatgcaat tgttgttgtt aacttgttta ttgcagctta taatggttac aaataaagca    5280
atagcatcac aaatttcaca aataaagcat ttttttcact gcattctagt tgtggtttgt    5340
ccaaactcat caatgtatct tatcatgtct ggatctgatc actgcttgag cctaggagat    5400
ccgaaccaga taagtgaaat ctagttccaa actattttgt cattttttaat tttcgtatta    5460 gcttacgacg ctacacccag ttcccatcta ttttgtcact cttccctaaa taatccttaa    5520
aaactccatt tccaccccctc ccagttccca actattttgt ccgcccacag cggggcattt    5580
ttcttcctgt tatgttttta atcaaacatc ctgccaactc catgtgacaa accgtcatct    5640
tcggctactt tttctctgtc acagaatgaa aattttctg tcatctcttc gttattaatg    5700
tttgtaattg actgaatatc aacgcttatt tgcagcctga atggcgaatg g    5751
```

<210> SEQ ID NO 11
<211> LENGTH: 5148
<212> TYPE: DNA
<213> ORGANISM: Homo sapiens

```
<400> SEQUENCE: 11
acgttatcga ctgcacggtg caccaatgct tctggcgtca ggcagccatc ggaagctgtg      60
gtatggctgt gcaggtcgta aatcactgca taattcgtgt cgctcaaggc gcactcccgt     120
tctggataat gttttttgcg ccgacatcat aacggttctg gcaaatattc tgaaatgagc     180
tgttgacaat taatcatcgg ctcgtataat gtgtggaatt gtgagcggat aacaatttca     240
cacaggaaac agtattcatg tcccctatac taggttattg gaaaattaag ggccttgtgc     300
aacccactcg acttcttttg gaatatcttg aagaaaaata tgaagagcat ttgtatgagc     360
gcgatgaagg tgataaatgg cgaaacaaaa gtttgaatt gggtttggag tttcccaatc      420
ttccttatta tattgatggt gatgttaaat taacacagtc tatggccatc atacgttata     480
tagctgacaa gcacaacatg ttgggtggtt gtccaaaaga gcgtgcagag atttcaatgc     540
ttgaaggagc ggttttggat attagatacg gtgtttcgag aattgcatat agtaaagact     600
ttgaaactct caaagttgat tttcttagca agctacctga aatgctgaaa atgttcgaag     660
atcgtttatg tcataaaaca tatttaaatg gtgatcatgt aacccatcct gacttcatgt     720
tgtatgacgc tcttgatgtt gttttataca tggacccaat gtgcctggat gcgttcccaa     780
aattagtttg ttttaaaaaa cgtattgaag ctatcccaca aattgataag tacttgaaat     840
ccagcaagta tatagcatgg cctttgcagg gctggcaagc cacgtttggt ggtggcgacc     900
atcctccaaa atcggatctg gaagttctgt tccaggggcc cctgggatcc aggcctccca     960
aagtaccgcc aagagaacct tgtcaccga gtaactcgcg cacaccgagt cccaaaagcc     1020
ttccgtctta cctcaatggg gtcatgcccc cgacacagag ctttgcccct gatcccaagt     1080
atgtcagcag caaagcactg caaagacaga acagcgaagg atctgccagt tagctcgagc     1140
ggccgcatcg tgactgactg acgatctgcc tcgcgcgttt cggtgatgac ggtgaaaacc     1200
tctgacacat gcagctcccg gagacggtca cagcttgtct gtaagcggat gccgggagca     1260
gacaagcccg tcagggcgcg tcagcgggtg ttggcgggtg tcgggcgca gccatgaccc      1320 agtcacgtag cgatagcgga gtgtataatt cttgaagacg aaagggcctc gtgatacgcc     1380
tatttttata ggttaatgtc atgataataa tggtttctta gacgtcaggt ggcactttc      1440 ggggaaatgt gcgcggaacc cctatttgtt tatttttcta atacattca aatatgtatc      1500 cgctcatgag acaataaccc tgataaatgc ttcaataata ttgaaaaagg aagagtatga     1560
gtattcaaca tttccgtgtc gcccttattc cctttttgc ggcatttgc cttcctgttt       1620 ttgctcaccc agaaacgctg gtgaaagtaa aagatgctga agatcagttg ggtgcacgag     1680
tgggttacat cgaactggat ctcaacagcg gtaagatcct tgagagtttt cgccccgaag     1740
aacgttttcc aatgatgagc acttttaaag ttctgctatg tggcgcggta ttatcccgtg     1800
ttgacgccgg gcaagagcaa ctcggtcgcc gcatacacta ttctcagaat gacttggttg     1860
agtactcacc agtcacagaa aagcatctta cggatggcat gacagtaaga gaattatgca     1920
gtgctgccat aaccatgagt gataacactg cggccaactt acttctgaca acgatcggag     1980
gaccgaagga gctaaccgct ttttgcaca acatggggga tcatgtaact cgccttgatc      2040
gttgggaacc ggagctgaat gaagccatac caaacgacga gcgtgacacc acgatgcctg     2100
cagcaatggc aacaacgttg cgcaaactat taactggcga actacttact ctagcttccc     2160
ggcaacaatt aatagactgg atggaggcgg ataaagttgc aggaccactt ctgcgctcgg     2220
cccttccggc tggctggttt attgctgata aatctggagc cggtgagcgt gggtctcgcg     2280
gtatcattgc agcactgggg ccagatggta agccctcccg tatcgtagtt atctacacga     2340
```

```
cggggagtca ggcaactatg gatgaacgaa atagacagat cgctgagata ggtgcctcac   2400
tgattaagca ttggtaactg tcagaccaag tttactcata tatactttag attgatttaa   2460
aacttcattt ttaatttaaa aggatctagg tgaagatcct ttttgataat ctcatgacca   2520 aaatcccta acgtgagttt tcgttccact gagcgtcaga ccccgtagaa aagatcaaag   2580
gatcttcttg agatcctttt tttctgcgcg taatctgctg cttgcaaaca aaaaaaccac   2640
cgctaccagc ggtggtttgt ttgccggatc aagagctacc aactctttt ccgaaggtaa   2700 ctggcttcag cagagcgcag ataccaaata ctgtccttct agtgtagccg tagttaggcc   2760
accacttcaa gaactctgta gcaccgccta catacctcgc tctgctaatc ctgttaccag   2820
tggctgctgc cagtggcgat aagtcgtgtc ttaccgggtt ggactcaaga cgatagttac   2880
cggataaggc gcagcggtcg ggctgaacgg ggggttcgtg cacacagccc agcttggagc   2940
gaacgaccta caccgaactg agatacctac agcgtgagct atgagaaagc gccacgcttc   3000
ccgaagggag aaaggcggac aggtatccgg taagcggcag ggtcggaaca ggagagcgca   3060
cgagggagct tccaggggga aacgcctggt atctttatag tcctgtcggg tttcgccacc   3120
tctgacttga gcgtcgattt ttgtgatgct cgtcagggg gcggagccta tggaaaaacg   3180
ccagcaacgc ggccttttta cggttcctgg ccttttgctg gccttttgct cacatgttct   3240
ttcctgcgtt atcccctgat tctgtggata accgtattac cgcctttgag tgagctgata   3300
ccgctcgccg cagccgaacg accgagcgca gcgagtcagt gagcgaggaa gcggaagagc   3360
gcctgatgcg gtattttctc cttacgcatc tgtgcggtat ttcacaccgc ataaattccg   3420
acaccatcga atggtgcaaa acctttcgcg gtatggcatg atagcgcccg gaagagagtc   3480
aattcagggt ggtgaatgtg aaaccagtaa cgttatacga tgtcgcagag tatgccggtg   3540
tctcttatca gaccgtttcc cgcgtggtga accggccagc cacgtttctg cgaaaacgcg   3600
ggaaaaagtg gaagcggcga tggcggagct gaattacatt cccaaccgcg tggcacaaca   3660
actggcgggc aaacagtcgt tgctgattgg cgttgccacc tccagtctgg ccctgcacgc   3720
gccgtcgcaa attgtcgcgg cgattaaatc tcgcgccgat caactgggtg ccagcgtggt   3780
ggtgtcgatg gtagaacgaa gcggcgtcga agcctgtaaa gcggcggtgc acaatcttct   3840
cgcgcaacgc gtcagtgggc tgatcattaa ctatccgctg gatgaccagg atgccattgc   3900
tgtggaagct gcctgcacta atgttccggc gttatttctt gatgtctctg accagacacc   3960
catcaacagt attattttct cccatgaaga cggtacgcga ctgggcgtgg agcatctggt   4020
cgcattgggt caccagcaaa tcgcgctgtt agcgggccca ttaagttctg tctcggcgcg   4080
tctgcgtctg gctggctggc ataaatatct cactcgcaat caaattcagc cgatagcgga   4140
acgggaaggc gactggagtg ccatgtccgg ttttcaacaa accatgcaaa tgctgaatga   4200
gggcatcgtt cccactgcga tgctggttgc caacgatcag atggcgctgg gcgcaatgcg   4260
cgccattacc gagtccgggc tgcgcgttgg tgcggatatc tcggtagtgg gatacgacga   4320
taccgaagac agctcatgtt atatcccgcc gtcaaccacc atcaaacagg attttcgcct   4380
gctggggcaa accagcgtgg accgcttgct gcaactctct cagggccagg cggtgaaggg   4440
caatcagctg ttgcccgtct cactggtgaa aagaaaaacc accctggcgc ccaatacgca   4500
aaccgcctct ccccgcgcgt tggccgattc attaatgcag ctggcacgac aggtttcccg   4560
actggaaagc gggcagtgag cgcaacgcaa ttaatgtgag ttagctcact cattaggcac   4620
cccaggcttt acactttatg cttccggctc gtatgttgtg tggaattgtg agcggataac   4680
aatttcacac aggaaacagc tatgaccatg attacggatt cactggccgt cgttttacaa   4740
```

```
cgtcgtgact gggaaaaccc tggcgttacc caacttaatc gccttgcagc acatcccct    4800 ttcgccagct ggcgtaatag cgaagaggcc cgcaccgatc gcccttccca acagttgcgc   4860
agcctgaatg gcgaatggcg ctttgcctgg tttccggcac cagaagcggt gccggaaagc   4920
tggctggagt gcgatcttcc tgaggccgat actgtcgtcg tccccctcaaa ctggcagatg   4980 cacggttacg atgcgcccat ctacaccaac gtaacctatc ccattacggt caatccgccg   5040
tttgttccca cggagaatcc gacgggttgt tactcgctca catttaatgt tgatgaaagc   5100
tggctacagg aaggccagac gcgaattatt tttgatggcg ttggaatt                5148
```

<210> SEQ ID NO 12
<211> LENGTH: 25
<212> TYPE: PRT
<213> ORGANISM: Homo sapiens

<400> SEQUENCE: 12

Met Ser Tyr His His His His His His Asp Tyr Asp Ile Pro Thr Thr
1               5                   10                  15

Glu Asn Leu Tyr Phe Gln Gly Ala Met
            20                  25

<210> SEQ ID NO 13
<211> LENGTH: 8
<212> TYPE: PRT
<213> ORGANISM: Homo sapiens

<400> SEQUENCE: 13

Asp Tyr Lys Asp Asp Asp Asp Lys
1               5

<210> SEQ ID NO 14
<211> LENGTH: 191
<212> TYPE: PRT
<213> ORGANISM: Homo sapiens

<400> SEQUENCE: 14

Gly Glu Ala Pro Asn Gln Ala Leu Leu Arg Ile Leu Lys Glu Thr Glu
1               5                   10                  15

Phe Lys Lys Ile Lys Val Leu Gly Ser Gly Ala Phe Gly Thr Val Tyr
            20                  25                  30

Lys Gly Leu Trp Ile Pro Glu Gly Glu Lys Val Lys Ile Pro Val Ala
        35                  40                  45

Ile Lys Glu Leu Arg Glu Ala Thr Ser Pro Lys Ala Asn Lys Glu Ile
    50                  55                  60

Leu Asp Glu Ala Tyr Val Met Ala Ser Val Asp Asn Pro His Val Cys
65                  70                  75                  80

Arg Leu Leu Gly Ile Cys Leu Thr Ser Thr Val Gln Leu Ile Thr Gln
                85                  90                  95

His Arg Ile Tyr Thr His Gln Ser Asp Val Trp Ser Tyr Gly Val Thr
            100                 105                 110

Val Trp Glu Leu Met Thr Phe Gly Ser Lys Pro Tyr Asp Gly Ile Pro
        115                 120                 125

Ala Ser Glu Ile Ser Ser Ile Leu Glu Lys Gly Glu Arg Leu Pro Gln
    130                 135                 140

Phe Pro Ile Cys Thr Ile Asp Val Tyr Met Ile Met Lys Cys Trp Met
145                 150                 155                 160

Ile Asp Ala Asp Ser Arg Pro Lys Phe Arg Glu Leu Ile Leu Glu Phe
                165                 170                 175

```
Ser Lys Met Ala Arg Asp Pro Gln Arg Tyr Leu Val Ile Gln Gly
            180                 185                 190
```

<210> SEQ ID NO 15
<211> LENGTH: 191
<212> TYPE: PRT
<213> ORGANISM: Mus musculus

<400> SEQUENCE: 15

```
Gly Glu Ala Pro Asn Gln Ala His Leu Arg Ile Leu Lys Glu Thr Glu
1               5                   10                  15

Phe Lys Lys Ile Lys Val Leu Gly Ser Gly Ala Phe Gly Thr Val Tyr
            20                  25                  30

Lys Gly Leu Trp Ile Pro Glu Gly Glu Lys Val Lys Ile Pro Val Ala
        35                  40                  45

Ile Lys Glu Leu Arg Glu Ala Thr Ser Pro Lys Ala Asn Lys Glu Ile
    50                  55                  60

Leu Asp Glu Ala Tyr Val Met Ala Ser Val Asp Asn Pro His Val Cys
65                  70                  75                  80

Arg Leu Leu Gly Ile Cys Leu Thr Ser Thr Val Gln Leu Ile Thr Gln
                85                  90                  95

His Arg Ile Tyr Thr His Gln Ser Asp Val Trp Ser Tyr Gly Val Thr
            100                 105                 110

Val Trp Glu Leu Met Thr Phe Gly Ser Lys Pro Tyr Asp Gly Ile Pro
        115                 120                 125

Ala Ser Glu Ile Ser Ser Ile Leu Glu Lys Gly Glu Arg Leu Pro Gln
    130                 135                 140

Phe Pro Ile Cys Thr Ile Asp Val Tyr Met Ile Met Lys Cys Trp Met
145                 150                 155                 160

Ile Asp Ala Asp Ser Arg Pro Lys Phe Arg Glu Leu Ile Leu Glu Phe
                165                 170                 175

Ser Lys Met Ala Arg Asp Pro Gln Arg Tyr Leu Val Ile Gln Gly
            180                 185                 190
```

<210> SEQ ID NO 16
<211> LENGTH: 191
<212> TYPE: PRT
<213> ORGANISM: Homo sapiens

<400> SEQUENCE: 16

```
Gly Ala Met Pro Asn Gln Ala Gln Met Arg Ile Leu Lys Glu Thr Glu
1               5                   10                  15

Leu Arg Lys Val Lys Val Leu Gly Ser Gly Ala Phe Gly Thr Val Tyr
            20                  25                  30

Lys Gly Ile Trp Ile Pro Asp Gly Glu Asn Val Lys Ile Pro Val Ala
        35                  40                  45

Ile Lys Val Leu Arg Glu Asn Thr Ser Pro Lys Ala Asn Lys Glu Ile
    50                  55                  60

Leu Asp Glu Ala Tyr Val Met Ala Gly Val Gly Ser Pro Tyr Val Ser
65                  70                  75                  80

Arg Leu Leu Gly Ile Cys Leu Thr Ser Thr Val Gln Leu Val Thr Gln
                85                  90                  95

Arg Arg Arg Phe Thr His Gln Ser Asp Val Trp Ser Tyr Gly Val Thr
            100                 105                 110

Val Trp Glu Leu Met Thr Phe Gly Ala Lys Pro Tyr Asp Gly Ile Pro
        115                 120                 125
```

Ala Arg Glu Ile Pro Asp Leu Leu Glu Lys Gly Glu Arg Leu Pro Gln
    130                 135                 140

Pro Pro Ile Cys Thr Ile Asp Val Tyr Met Ile Met Val Lys Cys Trp
145                 150                 155                 160

Met Ile Asp Ser Glu Cys Arg Pro Arg Phe Arg Glu Leu Val Ser Glu
                165                 170                 175

Phe Ser Arg Met Ala Arg Asp Pro Gln Arg Phe Val Val Ile Gln
            180                 185                 190

<210> SEQ ID NO 17
<211> LENGTH: 191
<212> TYPE: PRT
<213> ORGANISM: Mus musculus

<400> SEQUENCE: 17

Gly Ala Val Pro Asn Gln Ala Gln Met Arg Ile Leu Lys Glu Thr Glu
1               5                   10                  15

Leu Arg Lys Leu Lys Val Leu Gly Ser Gly Ala Phe Gly Thr Val Tyr
            20                  25                  30

Lys Gly Ile Trp Ile Pro Asp Gly Glu Asn Val Lys Ile Pro Val Ala
        35                  40                  45

Ile Lys Val Leu Arg Glu Asn Thr Ser Pro Lys Ala Asn Lys Glu Ile
    50                  55                  60

Leu Asp Glu Ala Tyr Val Met Ala Gly Val Gly Ser Pro Tyr Val Ser
65                  70                  75                  80

Arg Leu Leu Gly Ile Cys Leu Thr Ser Thr Val Gln Leu Val Thr Gln
                85                  90                  95

Arg Arg Arg Phe Thr His Gln Ser Asp Val Trp Ser Tyr Gly Val Thr
            100                 105                 110

Val Trp Glu Leu Met Thr Phe Gly Ala Lys Pro Tyr Asp Gly Ile Pro
        115                 120                 125

Ala Arg Glu Ile Pro Asp Leu Leu Glu Lys Gly Glu Arg Leu Pro Gln
    130                 135                 140

Pro Pro Ile Cys Thr Ile Asp Val Tyr Met Ile Met Val Lys Cys Trp
145                 150                 155                 160

Met Ile Asp Ser Glu Cys Arg Pro Arg Phe Arg Glu Leu Val Ser Glu
                165                 170                 175

Phe Ser Arg Met Ala Arg Asp Pro Gln Arg Phe Val Val Ile Gln
            180                 185                 190

<210> SEQ ID NO 18
<211> LENGTH: 192
<212> TYPE: PRT
<213> ORGANISM: Homo sapiens

<400> SEQUENCE: 18

Gly Thr Ala Pro Asn Gln Ala Gln Leu Arg Ile Leu Lys Glu Thr Glu
1               5                   10                  15

Leu Lys Arg Val Lys Val Leu Gly Ser Gly Ala Phe Gly Thr Val Tyr
            20                  25                  30

Lys Gly Ile Trp Val Pro Glu Gly Glu Thr Val Lys Ile Pro Val Ala
        35                  40                  45

Ile Lys Ile Leu Asn Glu Thr Thr Gly Pro Lys Ala Asn Val Glu Phe
    50                  55                  60

Met Asp Glu Ala Leu Ile Met Ala Ser Met Asp His Pro His Leu Val
65                  70                  75                  80

Arg Leu Leu Gly Val Cys Leu Ser Pro Thr Ile Gln Leu Val Thr Gln

```
                    85                  90                  95
Tyr Arg Lys Phe Thr His Gln Ser Asp Val Trp Ser Tyr Gly Val Thr
                100                 105                 110

Ile Trp Glu Leu Met Thr Phe Gly Gly Lys Pro Tyr Asp Gly Ile Pro
            115                 120                 125

Thr Arg Glu Ile Pro Asp Leu Leu Glu Lys Gly Glu Arg Leu Pro Gln
        130                 135                 140

Pro Pro Ile Cys Thr Ile Asp Val Tyr Met Val Met Val Lys Cys Trp
145                 150                 155                 160

Met Ile Asp Ala Asp Ser Arg Pro Lys Phe Lys Glu Leu Ala Ala Glu
                165                 170                 175

Phe Ser Arg Met Ala Arg Asp Pro Gln Arg Tyr Leu Val Ile Gln Gly
            180                 185                 190
```

<210> SEQ ID NO 19
<211> LENGTH: 192
<212> TYPE: PRT
<213> ORGANISM: Mus musculus

<400> SEQUENCE: 19

```
Gly Thr Ala Pro Asn Gln Ala Gln Leu Arg Ile Leu Lys Glu Thr Glu
1               5                   10                  15

Leu Lys Arg Val Lys Val Leu Gly Ser Gly Ala Phe Gly Thr Val Tyr
            20                  25                  30

Lys Gly Ile Trp Val Pro Glu Gly Glu Thr Val Lys Ile Pro Val Ala
        35                  40                  45

Ile Lys Ile Leu Asn Glu Thr Thr Gly Pro Lys Ala Asn Val Glu Phe
    50                  55                  60

Met Asp Glu Ala Leu Ile Met Ala Ser Met Asp His Pro His Leu Val
65                  70                  75                  80

Arg Leu Leu Gly Val Cys Leu Ser Pro Thr Ile Gln Leu Val Thr Gln
                85                  90                  95

Tyr Arg Lys Phe Thr His Gln Ser Asp Val Trp Ser Tyr Gly Val Thr
                100                 105                 110

Ile Trp Glu Leu Met Thr Phe Gly Gly Lys Pro Tyr Asp Gly Ile Pro
            115                 120                 125

Thr Arg Glu Ile Pro Asp Leu Leu Glu Lys Gly Glu Arg Leu Pro Gln
        130                 135                 140

Pro Pro Ile Cys Thr Ile Asp Val Tyr Met Val Met Val Lys Cys Trp
145                 150                 155                 160

Met Ile Asp Ala Asp Ser Arg Pro Lys Phe Lys Glu Leu Ala Ala Glu
                165                 170                 175

Phe Ser Arg Met Ala Arg Asp Pro Gln Arg Tyr Leu Val Ile Gln Gly
            180                 185                 190
```

<210> SEQ ID NO 20
<211> LENGTH: 191
<212> TYPE: PRT
<213> ORGANISM: Homo sapiens

<400> SEQUENCE: 20

```
Glu Lys Ala Asn Lys Val Leu Ala Arg Ile Phe Lys Glu Thr Glu Leu
1               5                   10                  15

Arg Lys Leu Lys Val Leu Gly Ser Gly Val Phe Gly Thr Val His Lys
            20                  25                  30

Gly Val Trp Ile Pro Glu Gly Glu Ser Ile Lys Ile Pro Val Cys Ile
        35                  40                  45
```

```
Lys Val Ile Glu Asp Lys Ser Gly Arg Gln Ser Phe Gln Ala Val Thr
    50                  55                  60

Asp His Met Leu Ala Ile Gly Ser Leu Asp His Ala His Ile Val Arg
65                  70                  75                  80

Leu Leu Gly Leu Cys Pro Gly Ser Ser Leu Gln Leu Val Thr Gln Phe
                85                  90                  95

Gly Lys Tyr Thr His Gln Ser Asp Val Trp Ser Tyr Gly Val Thr Val
                100                 105                 110

Trp Glu Leu Met Thr Phe Gly Ala Glu Pro Tyr Ala Gly Leu Arg Leu
                115                 120                 125

Ala Glu Val Pro Asp Leu Leu Glu Lys Gly Glu Arg Leu Ala Gln Pro
            130                 135                 140

Gln Ile Cys Thr Ile Asp Val Tyr Met Val Met Val Lys Cys Trp Met
145                 150                 155                 160

Ile Asp Glu Asn Ile Arg Pro Thr Phe Lys Glu Leu Ala Asn Glu Phe
                165                 170                 175

Thr Arg Met Ala Arg Asp Pro Pro Arg Tyr Leu Val Ile Lys Arg
                180                 185                 190

<210> SEQ ID NO 21
<211> LENGTH: 191
<212> TYPE: PRT
<213> ORGANISM: Mus musculus

<400> SEQUENCE: 21

Glu Lys Ala Asn Lys Val Leu Ala Arg Ile Phe Lys Glu Thr Glu Leu
1               5                   10                  15

Arg Lys Leu Lys Val Leu Gly Ser Gly Val Phe Gly Thr Val His Lys
                20                  25                  30

Gly Ile Trp Ile Pro Glu Gly Glu Ser Ile Lys Ile Pro Val Cys Ile
            35                  40                  45

Lys Val Ile Glu Asp Lys Ser Gly Arg Gln Ser Phe Gln Ala Val Thr
    50                  55                  60

Asp His Met Leu Ala Ile Gly Ser Leu Asp His Ala His Ile Val Arg
65                  70                  75                  80

Leu Leu Gly Leu Cys Pro Gly Ser Ser Leu Gln Leu Val Thr Gln Phe
                85                  90                  95

Gly Lys Tyr Thr His Gln Ser Asp Val Trp Ser Tyr Gly Val Thr Val
                100                 105                 110

Trp Glu Leu Met Thr Phe Gly Ala Glu Pro Tyr Ala Gly Leu Arg Leu
                115                 120                 125

Ala Glu Ile Pro Asp Leu Leu Glu Lys Gly Glu Arg Leu Ala Gln Pro
            130                 135                 140

Gln Ile Cys Thr Ile Asp Val Tyr Met Val Met Val Lys Cys Trp Met
145                 150                 155                 160

Ile Asp Glu Asn Ile Arg Pro Thr Phe Lys Glu Leu Ala Asn Glu Phe
                165                 170                 175

Thr Arg Met Ala Arg Asp Pro Pro Arg Tyr Leu Val Ile Lys Arg
                180                 185                 190
```